United States Patent
Ishii et al.

(10) Patent No.: US 10,175,169 B2
(45) Date of Patent: Jan. 8, 2019

(54) OPTICAL SENSOR, OPTICAL TESTING APPARATUS, AND OPTICAL CHARACTERISTICS DETECTION METHOD

(71) Applicants: Toshihiro Ishii, Miyagi (JP); Yoichiro Takahashi, Miyagi (JP)

(72) Inventors: Toshihiro Ishii, Miyagi (JP); Yoichiro Takahashi, Miyagi (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 15/513,806

(22) PCT Filed: Oct. 29, 2015

(86) PCT No.: PCT/JP2015/005454
§ 371 (c)(1),
(2) Date: Mar. 23, 2017

(87) PCT Pub. No.: WO2016/075886
PCT Pub. Date: May 19, 2016

(65) Prior Publication Data
US 2018/0011015 A1    Jan. 11, 2018

(30) Foreign Application Priority Data
Nov. 13, 2014 (JP) .................. 2014-230745

(51) Int. Cl.
*G01N 21/00* (2006.01)
*G01N 21/47* (2006.01)
(Continued)

(52) U.S. Cl.
CPC ....... *G01N 21/4795* (2013.01); *A61B 5/0075* (2013.01); *A61B 5/0261* (2013.01);
(Continued)

(58) Field of Classification Search
CPC .......... G01N 21/49; G01N 2201/0612; G01N 21/03; G01N 21/55; G01J 1/0411; A61B 5/0261; A61B 5/0042
(Continued)

(56) References Cited

U.S. PATENT DOCUMENTS

| 5,032,024 A * | 7/1991 | Cope .................. A61B 5/14553 |
| | | 356/41 |
| 6,353,226 B1 * | 3/2002 | Khalil ................ A61B 5/14532 |
| | | 250/339.11 |

(Continued)

FOREIGN PATENT DOCUMENTS

| JP | 09-173323 | 7/1997 |
| JP | 11-169361 | 6/1999 |

(Continued)

OTHER PUBLICATIONS

European search report dated Oct. 16, 2017 in connection with corresponding European patent application No. 15858589.3.
(Continued)

*Primary Examiner* — Hoa Pham
(74) *Attorney, Agent, or Firm* — Cooper & Dunham LLP

(57) ABSTRACT

An optical sensor is provided. The optical sensor has an emitting system including at least one light emitting device which emits light onto an object; and a detecting system detecting the light which has been emitted by the emitting system and which has propagated through the object. The light emitting device is capable of emitting a plurality of light beams with different wavelengths onto substantially the same position of the object.

12 Claims, 38 Drawing Sheets

(51) Int. Cl.
*A61B 5/00* (2006.01)
*A61B 5/1455* (2006.01)
*A61B 5/026* (2006.01)

(52) U.S. Cl.
CPC .................. *A61B 5/14553* (2013.01); *G01N 2201/06113* (2013.01)

(58) Field of Classification Search
USPC ................................ 356/335–343, 432–440
See application file for complete search history.

(56) References Cited

U.S. PATENT DOCUMENTS

| | | | |
|---|---|---|---|
| 6,850,656 B1 * | 2/2005 | Bevilacqua | G01N 21/49 356/12 |
| 6,995,841 B2 * | 2/2006 | Scott | G01J 3/10 250/459.1 |
| 7,142,304 B1 * | 11/2006 | Barbour | G01N 21/4795 356/432 |
| 7,962,187 B2 * | 6/2011 | Fantini | A61B 5/4312 600/310 |
| 9,267,886 B2 | 2/2016 | Ohba et al. | |
| 10,039,452 B2 * | 8/2018 | Ishii | A61B 5/1455 |
| 2001/0038454 A1 * | 11/2001 | Tsuchiya | A61B 5/0059 356/432 |
| 2003/0058440 A1 | 3/2003 | Scott et al. | |
| 2006/0139634 A1 | 6/2006 | Scott et al. | |
| 2007/0232911 A1 | 10/2007 | Urano | |
| 2009/0156429 A1 | 6/2009 | Scott et al. | |
| 2011/0210270 A1 | 9/2011 | Tojo | |
| 2012/0219029 A1 | 8/2012 | Scott et al. | |
| 2013/0057868 A1 | 3/2013 | Oba et al. | |
| 2013/0100449 A1 * | 4/2013 | Yamaki | G01N 21/49 356/432 |
| 2014/0320859 A1 * | 10/2014 | Thennadil | G01N 21/0303 356/432 |
| 2016/0091496 A1 * | 3/2016 | Xu | G02B 6/3624 356/436 |
| 2016/0195473 A1 * | 7/2016 | Fujiwara | G01N 21/49 250/553 |
| 2016/0242647 A1 * | 8/2016 | Ishii | A61B 5/1455 |
| 2017/0179682 A1 * | 6/2017 | Ishii | A61B 5/0042 |

FOREIGN PATENT DOCUMENTS

| | | |
|---|---|---|
| JP | 2002-250893 | 9/2002 |
| JP | 2004-290544 | 10/2004 |
| JP | 3779134 | 5/2006 |
| JP | 2011-114228 | 6/2011 |
| JP | 2011-179903 | 9/2011 |
| JP | 2012-080975 | 4/2012 |
| JP | 2012-127937 | 7/2012 |
| JP | 2012-132740 | 7/2012 |
| JP | 2012-187358 | 10/2012 |
| JP | 5565774 | 8/2014 |
| JP | 2015-092151 | 5/2015 |
| WO | 03/021212 A1 | 3/2003 |
| WO | 2015/046624 A1 | 4/2015 |

OTHER PUBLICATIONS

Matthew E. Eames and Hamid Dehghani, "Wavelength dependence of sensitivity in spectral diffuse optical imaging: effect of normalization on image reconstruction," Opt. Express 16, 17780-17791 (2008).
Kris Olinger et al. "Photonic crystals with defect structures fabricated through a combination of holographic lithography and two-photon lithography," J. Applied Physics, vol. 108, No. 7, 073113-1 through 073113-4 (2010).
T. Shimokawa et al., "Hierarchical Bayesian Estimation Improves Depth Accuracy and Spatial Resolution of Diffuse Optical Tomography", Optics Express, vol. 20, No. 18, pp. 20427-20446 (2012).
International Search Report dated Jan. 26, 2016 in PCT/JP2015/005454 filed on Oct. 29, 2015.

* cited by examiner

[Fig. 1]
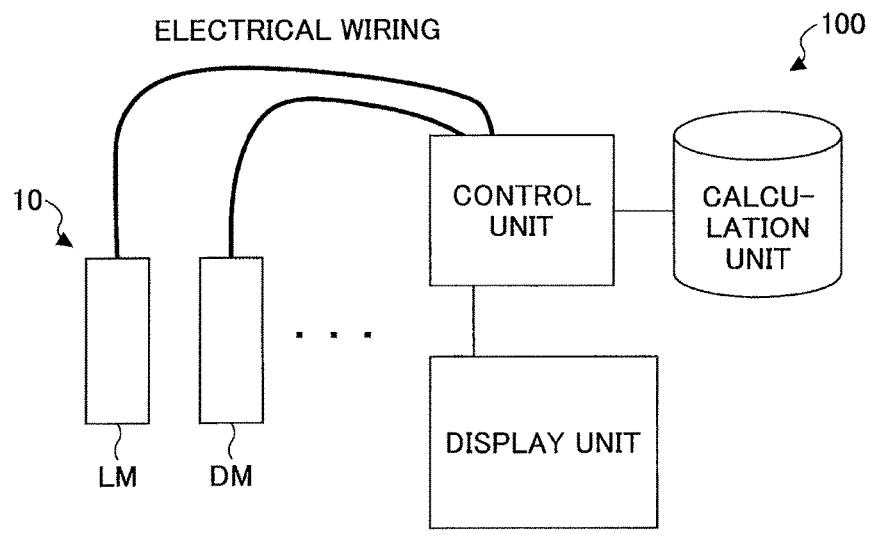
[Fig. 2]
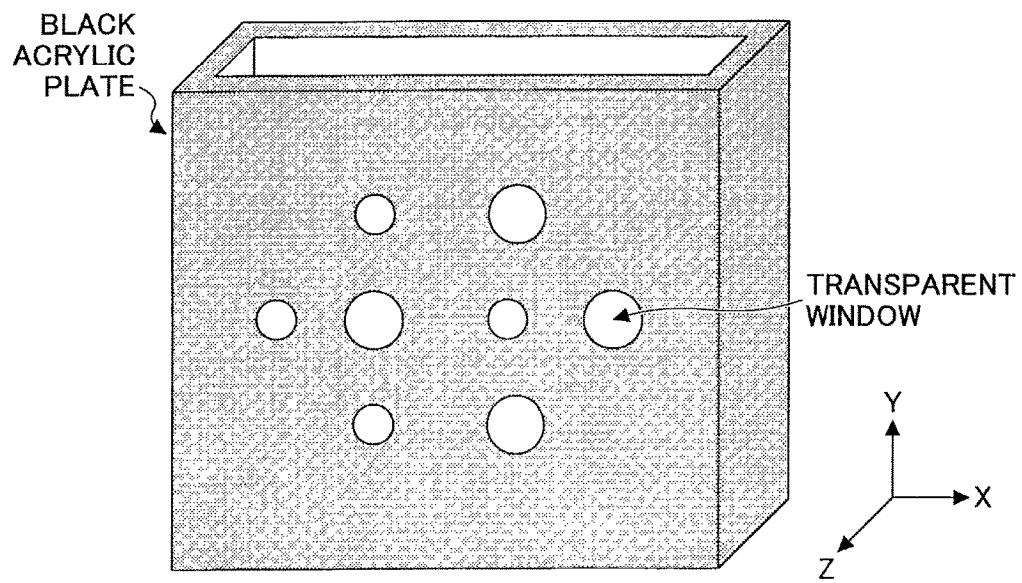

[Fig. 3]
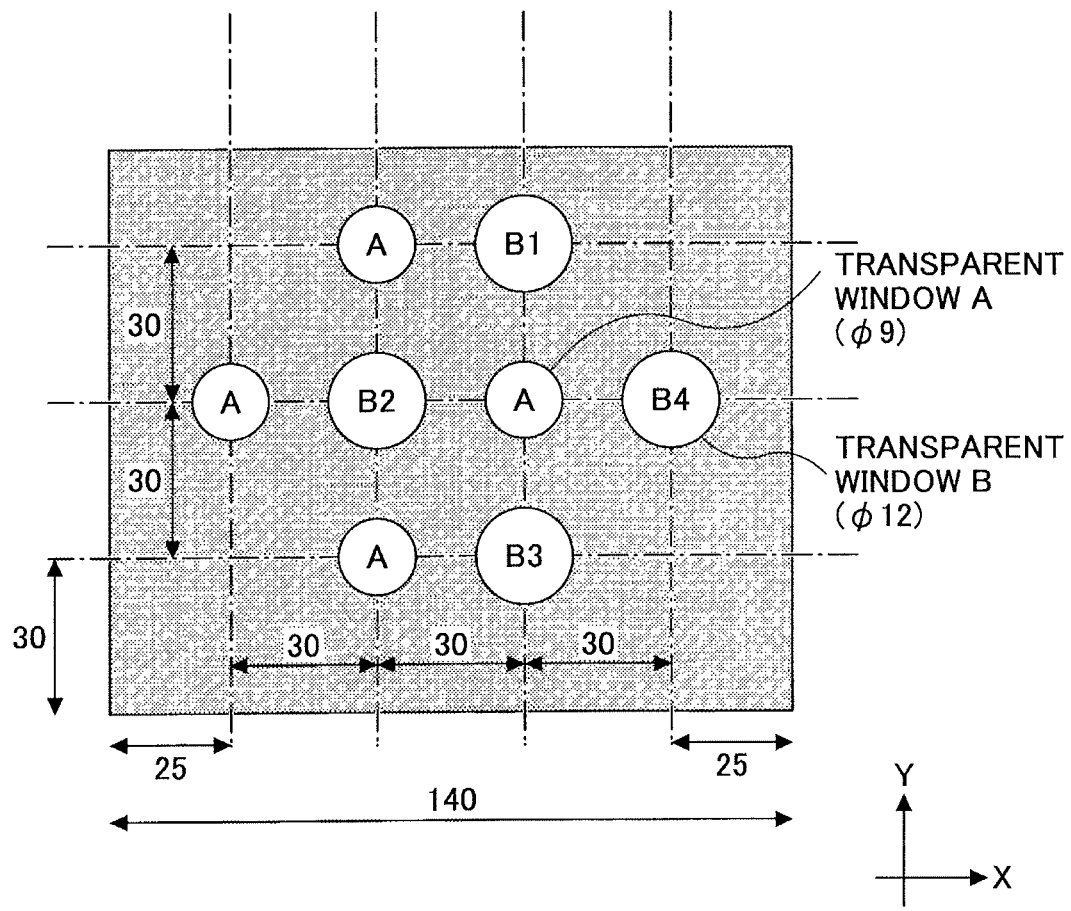

[Fig. 4]
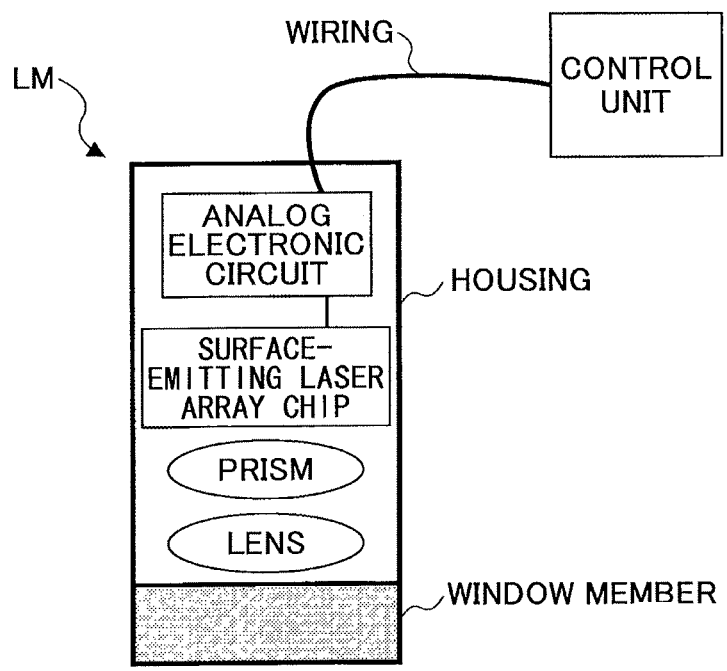
[Fig. 5]
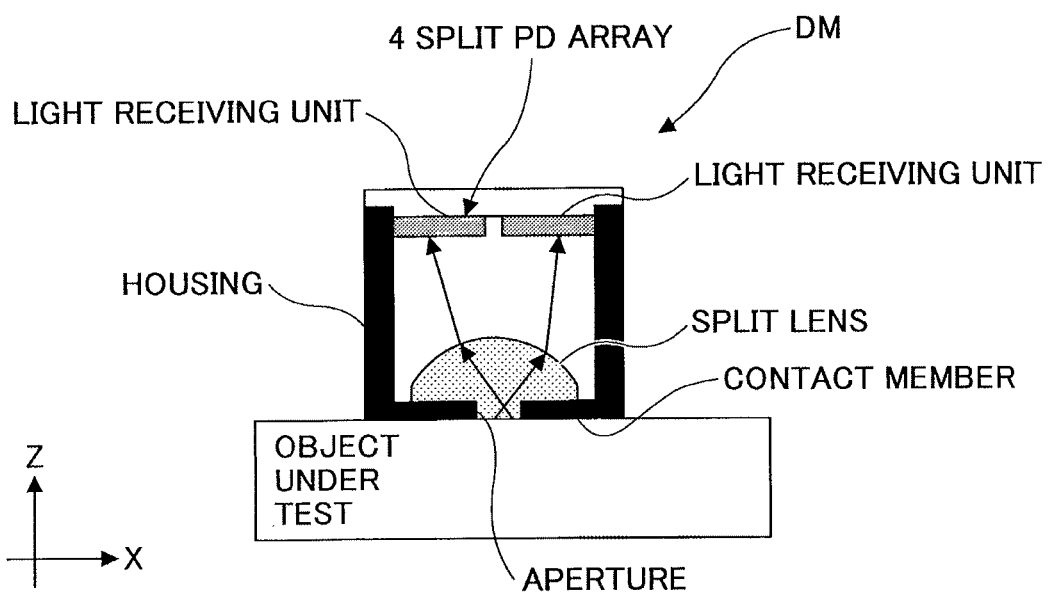

[Fig. 6]
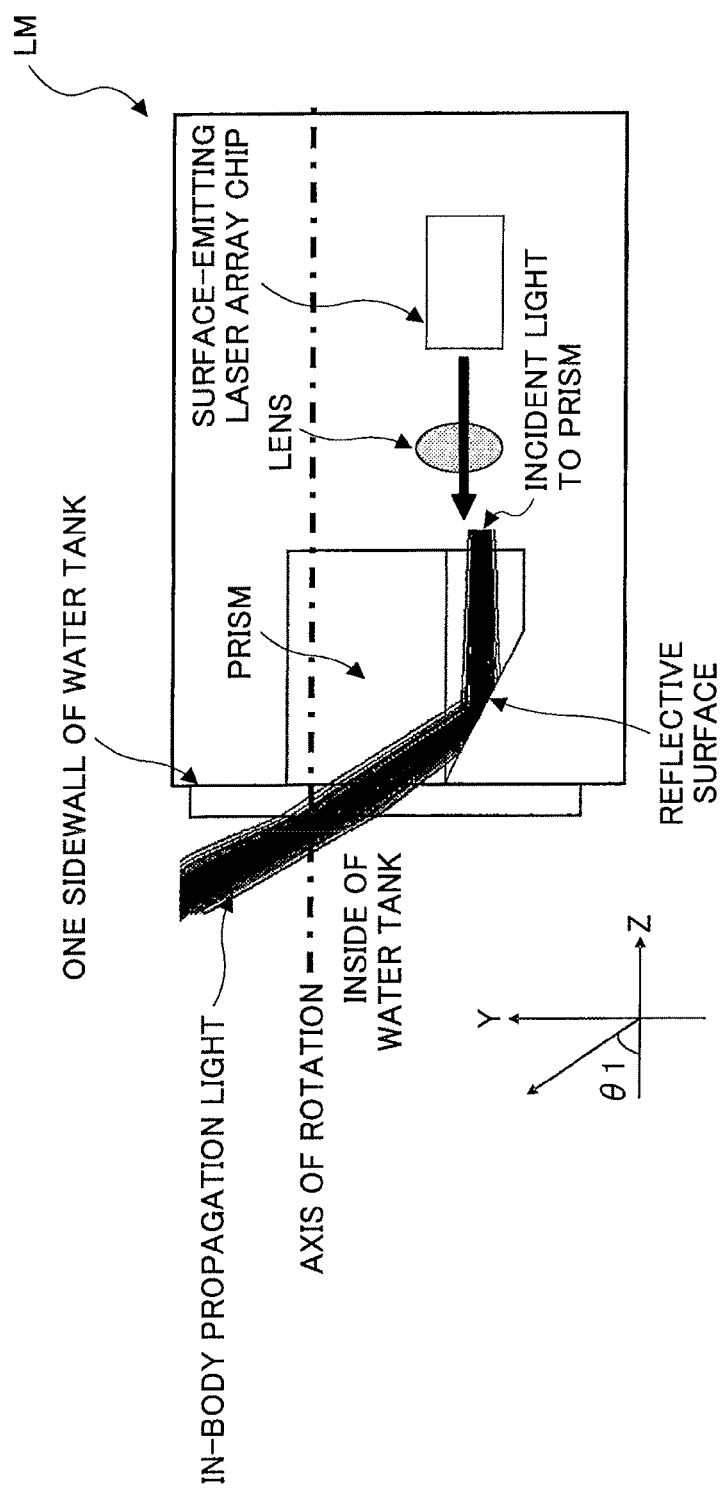

[Fig. 7]
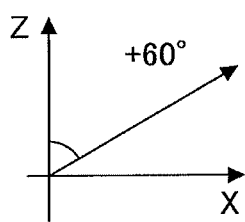
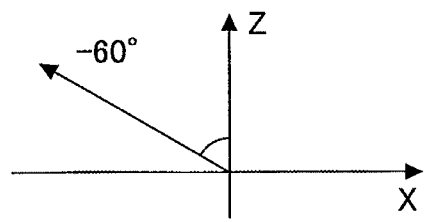
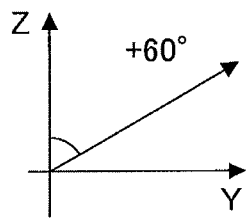
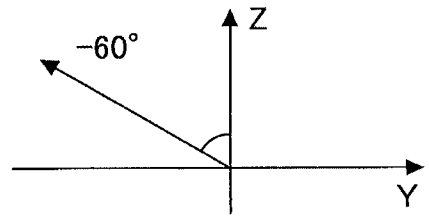

[Fig. 8]
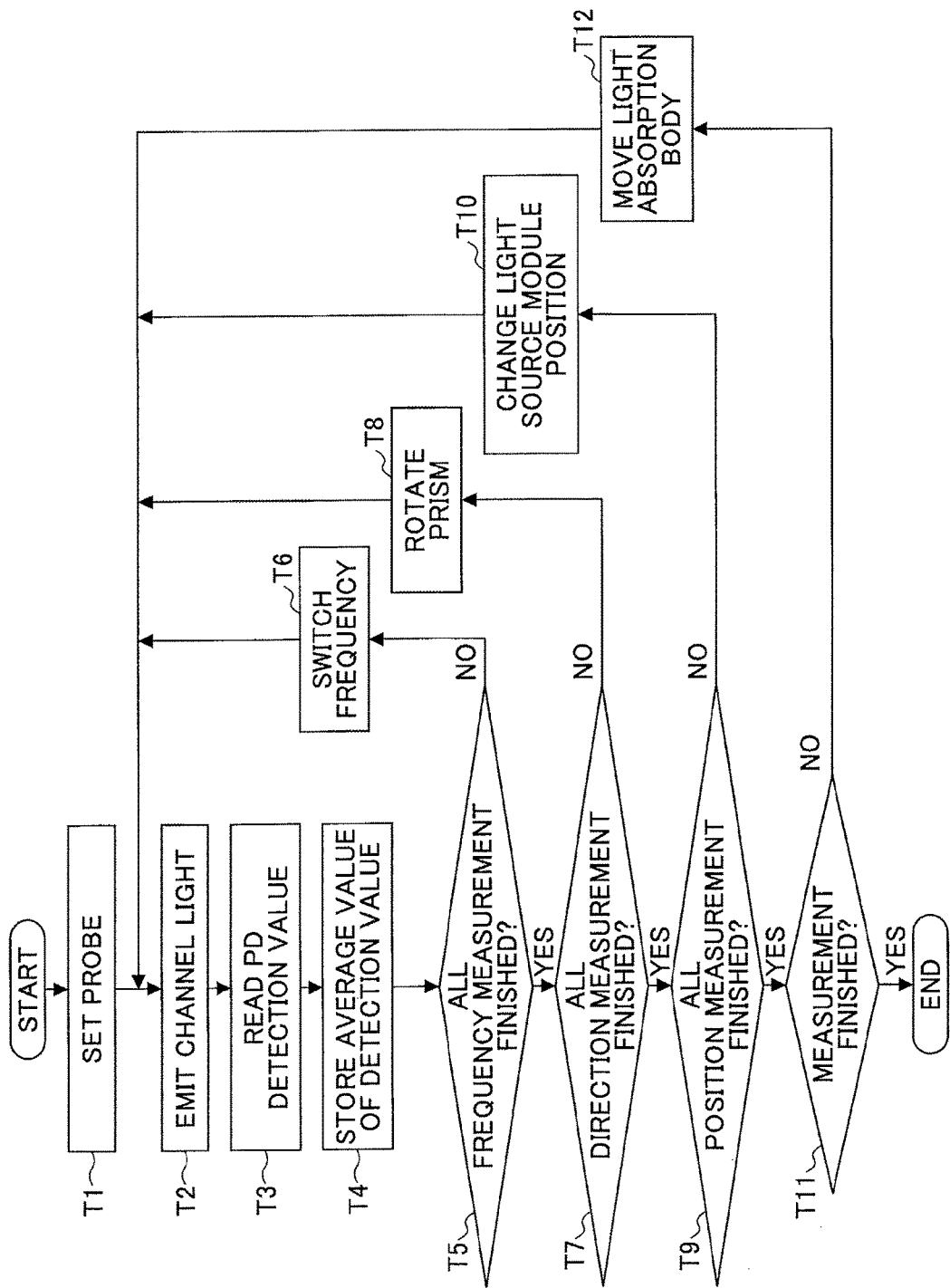

[Fig. 9]
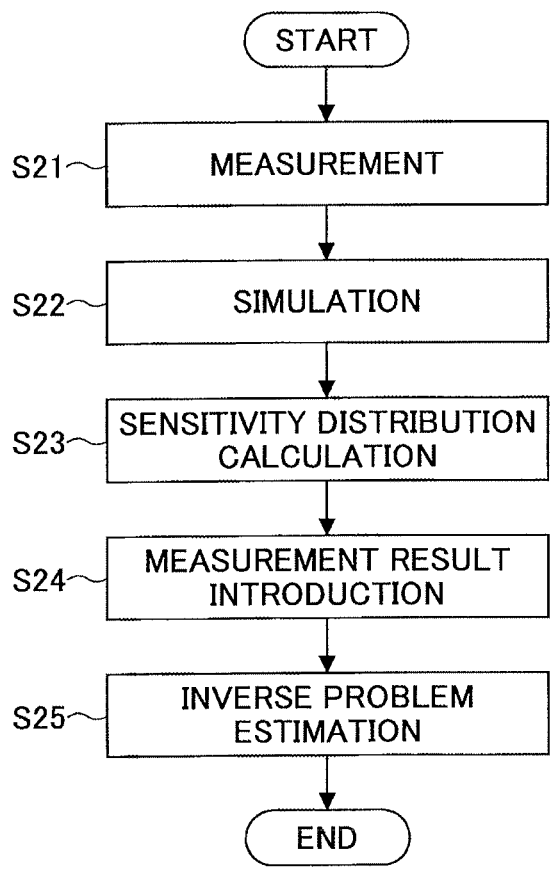

[Fig. 10]
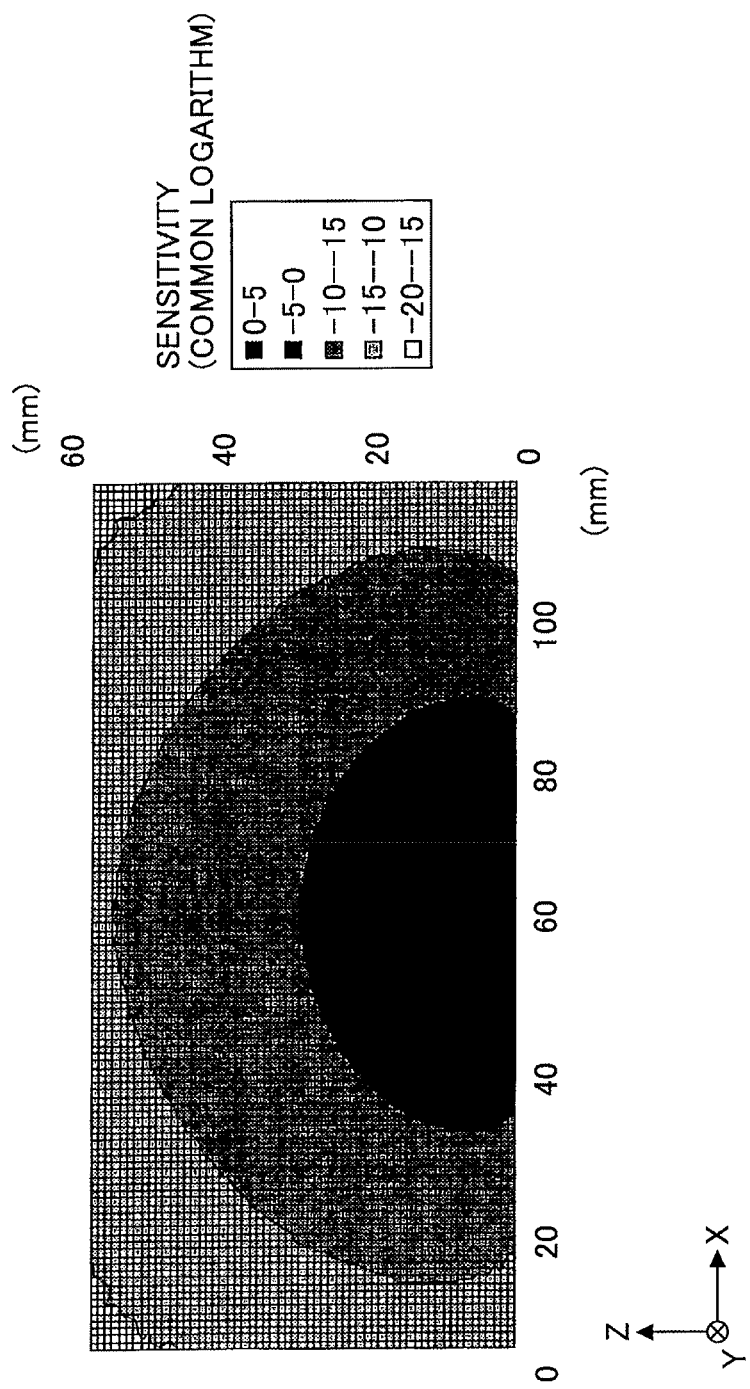

[Fig. 11]
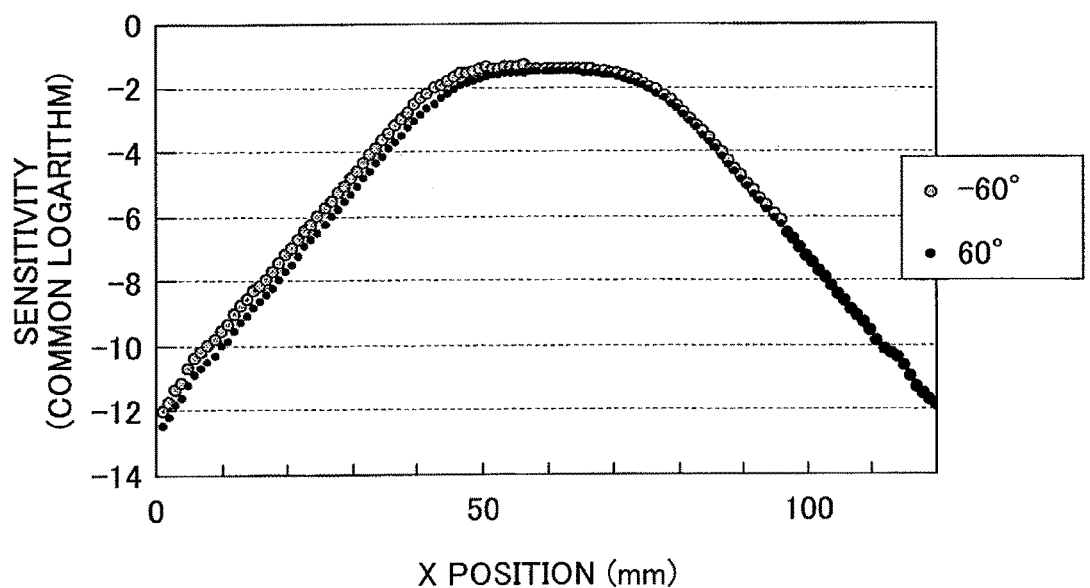
[Fig. 12]
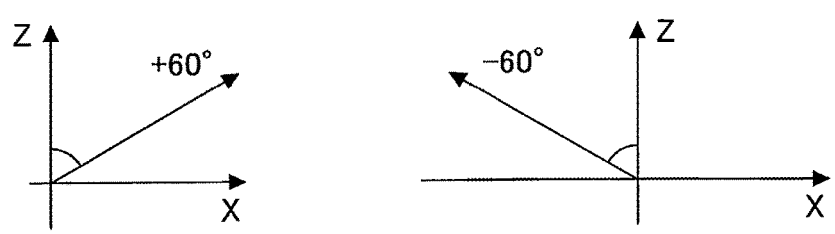

[Fig. 13A]
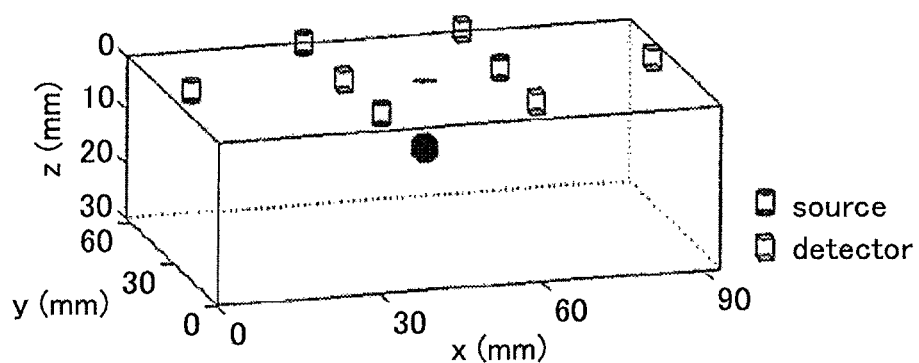
[Fig. 13B]
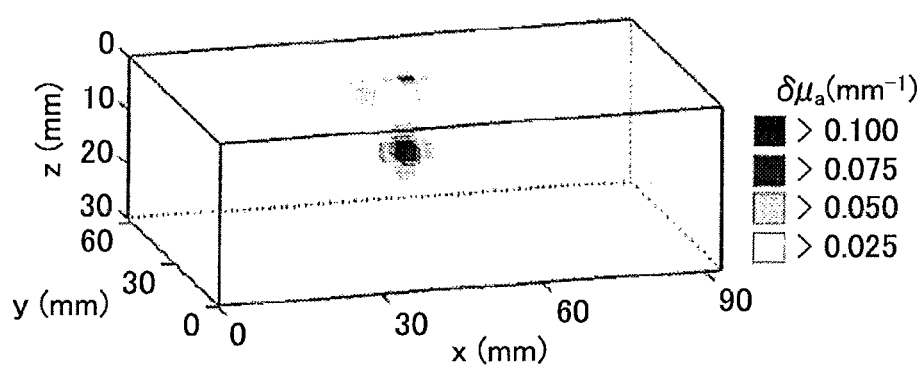

[Fig. 13C]
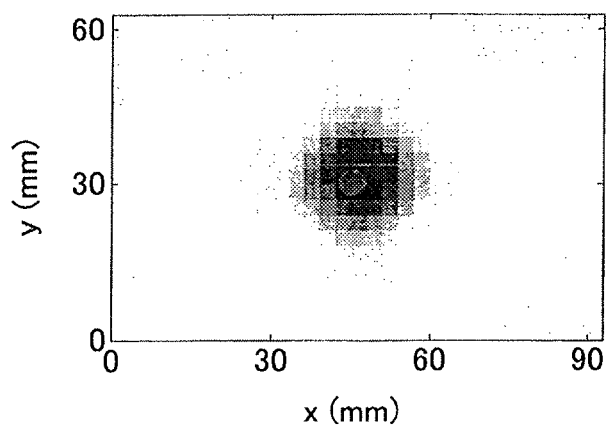
[Fig. 14A]
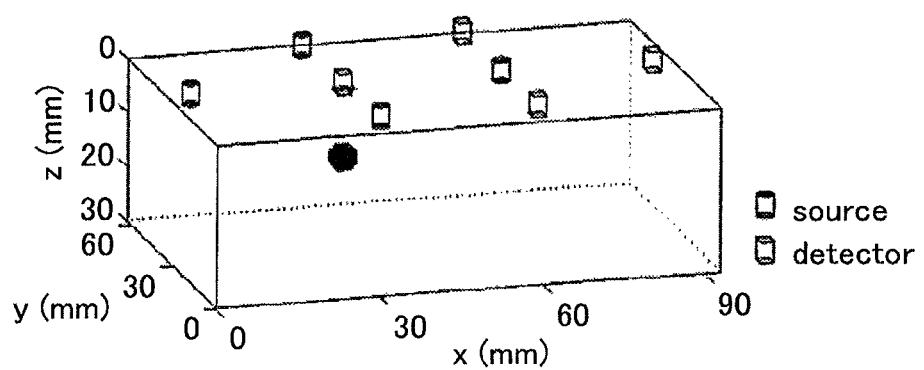

[Fig. 14B]
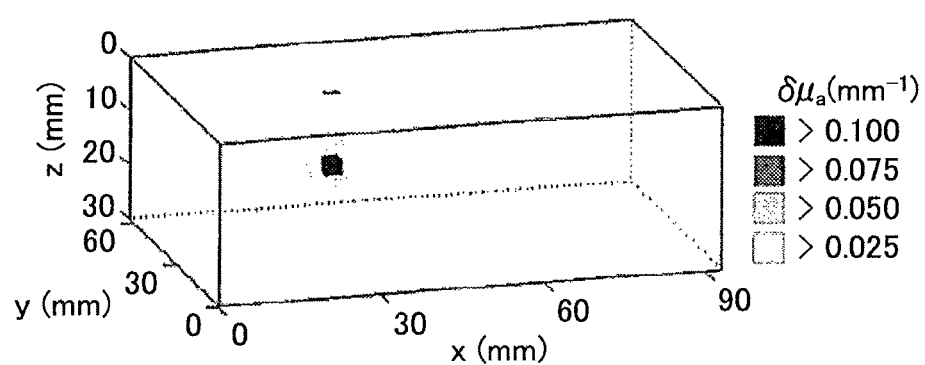
[Fig. 14C]
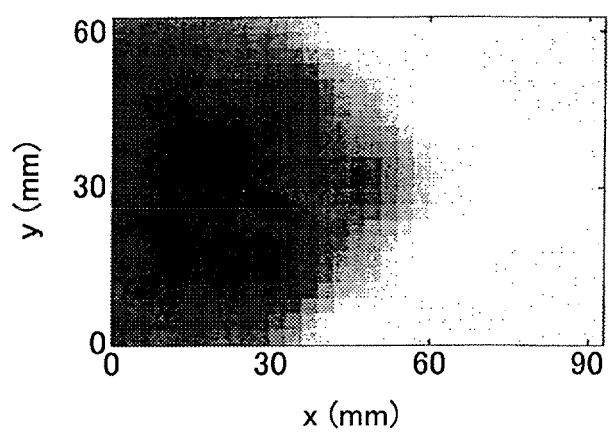

[Fig. 15]
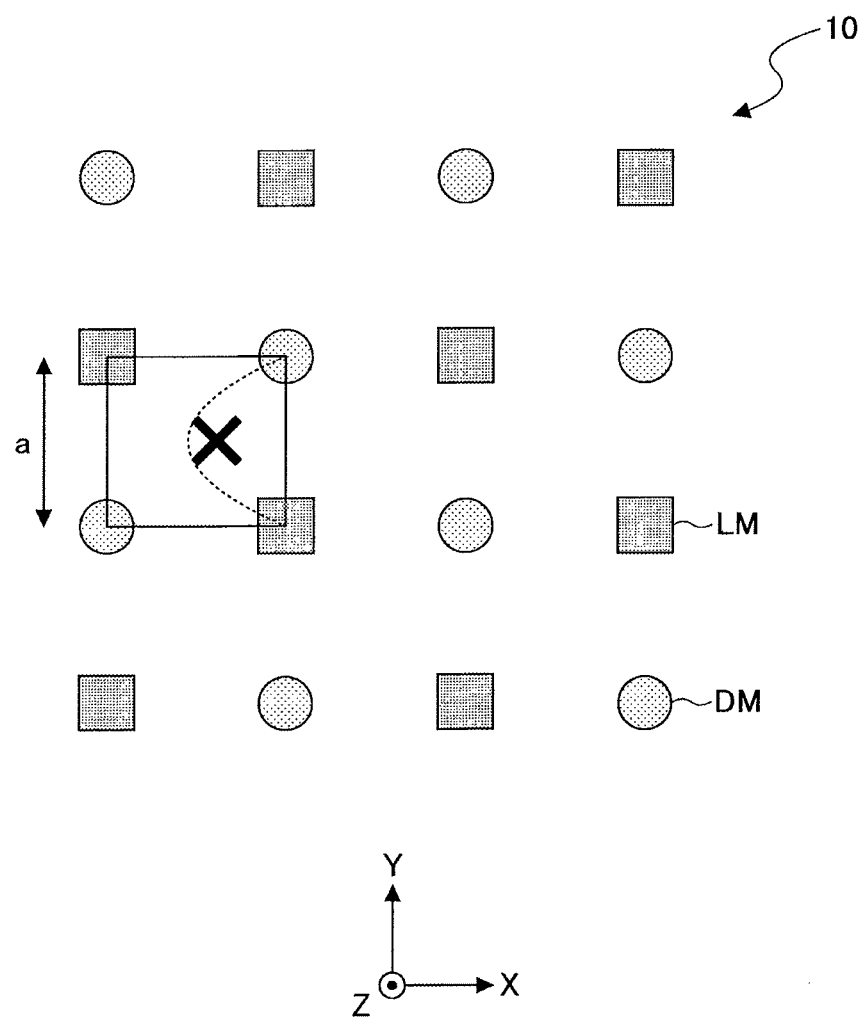

[Fig. 16]
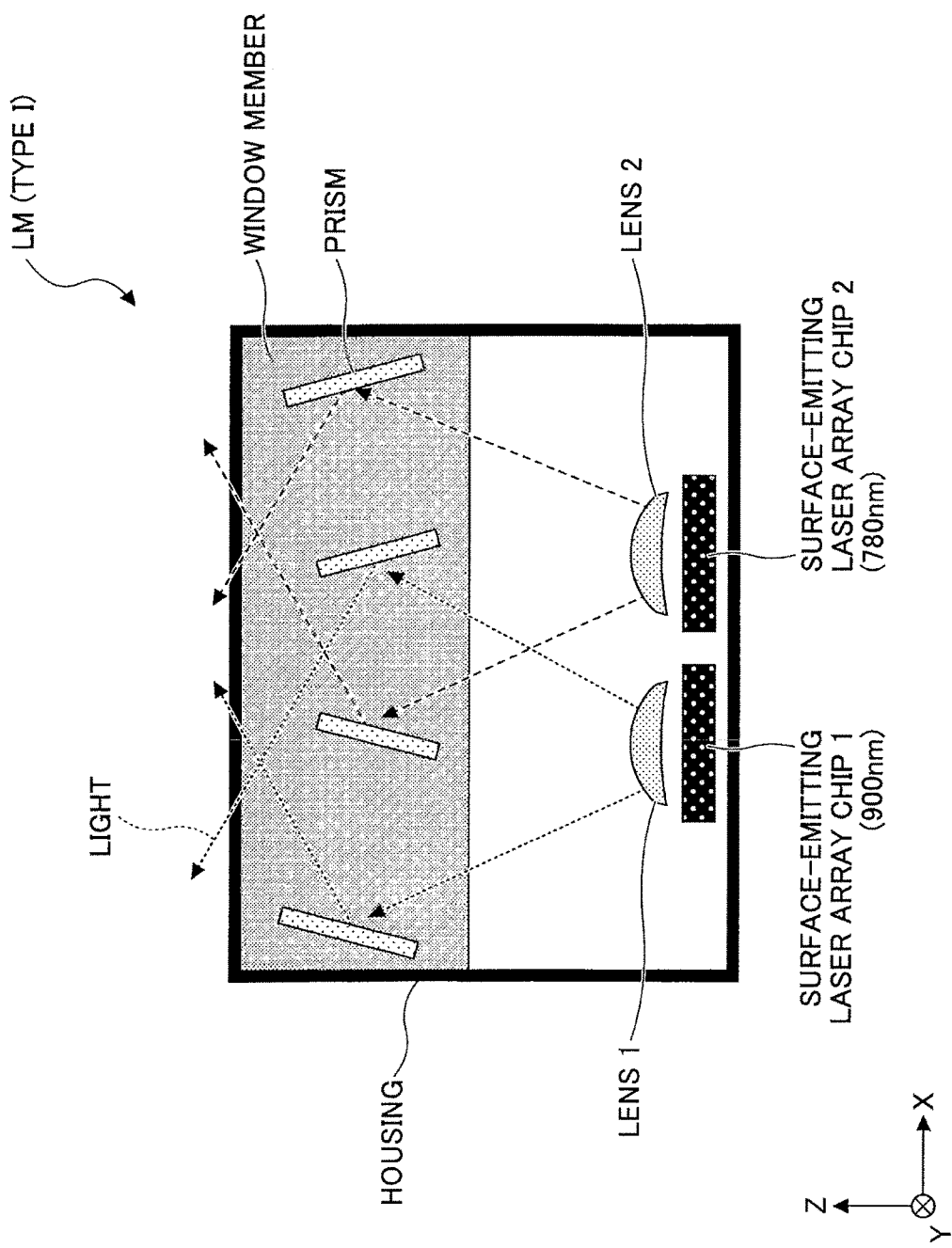

[Fig. 17]
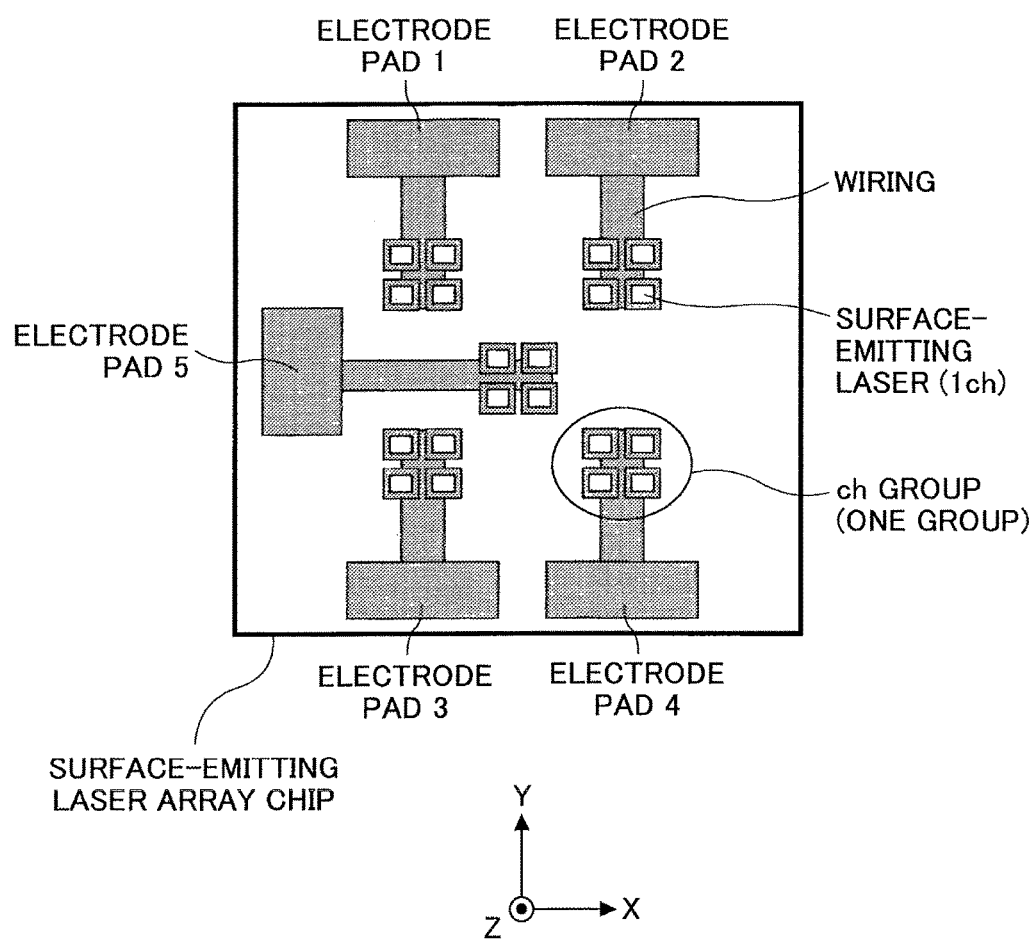

[Fig. 18A]
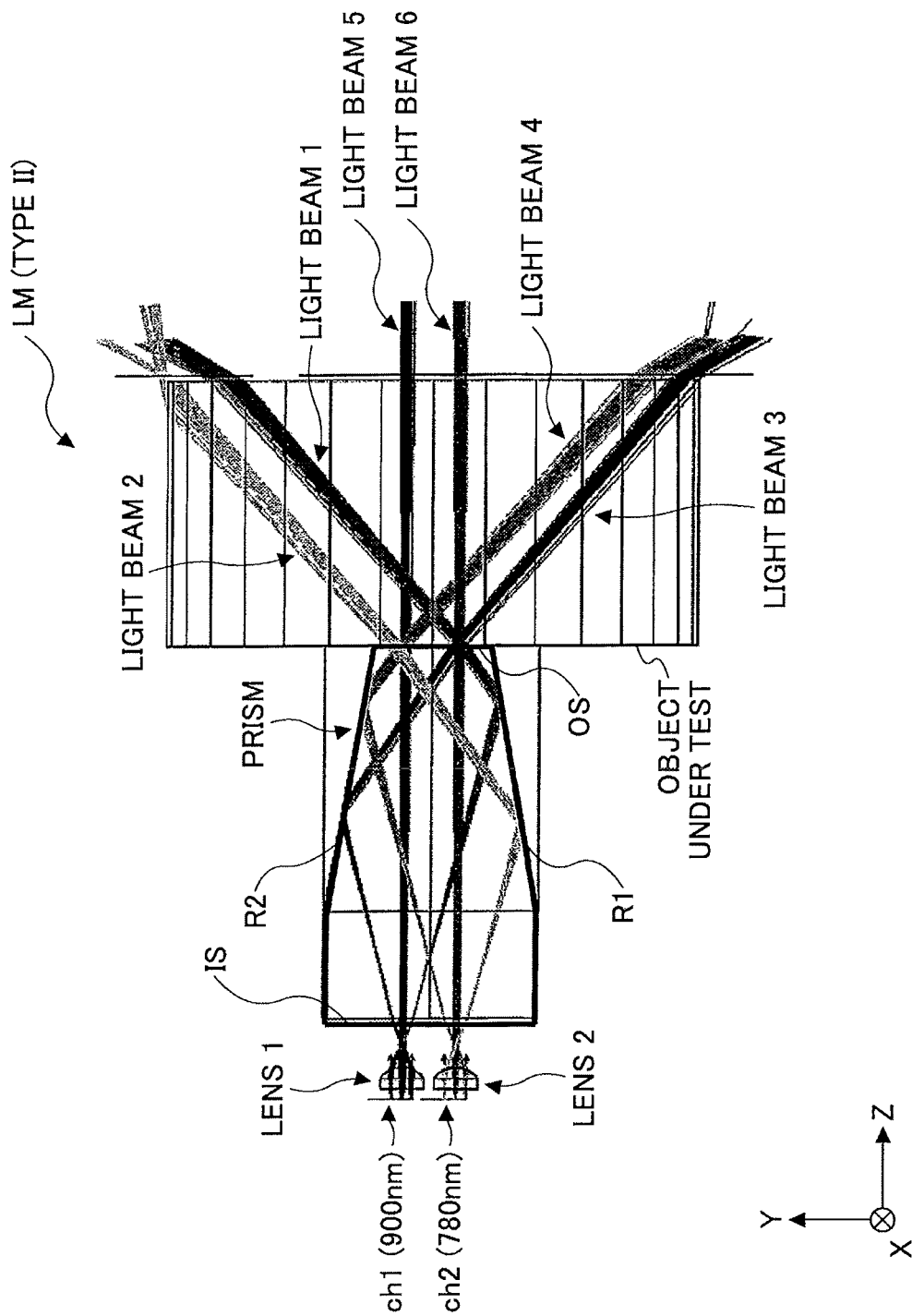

[Fig. 18B]
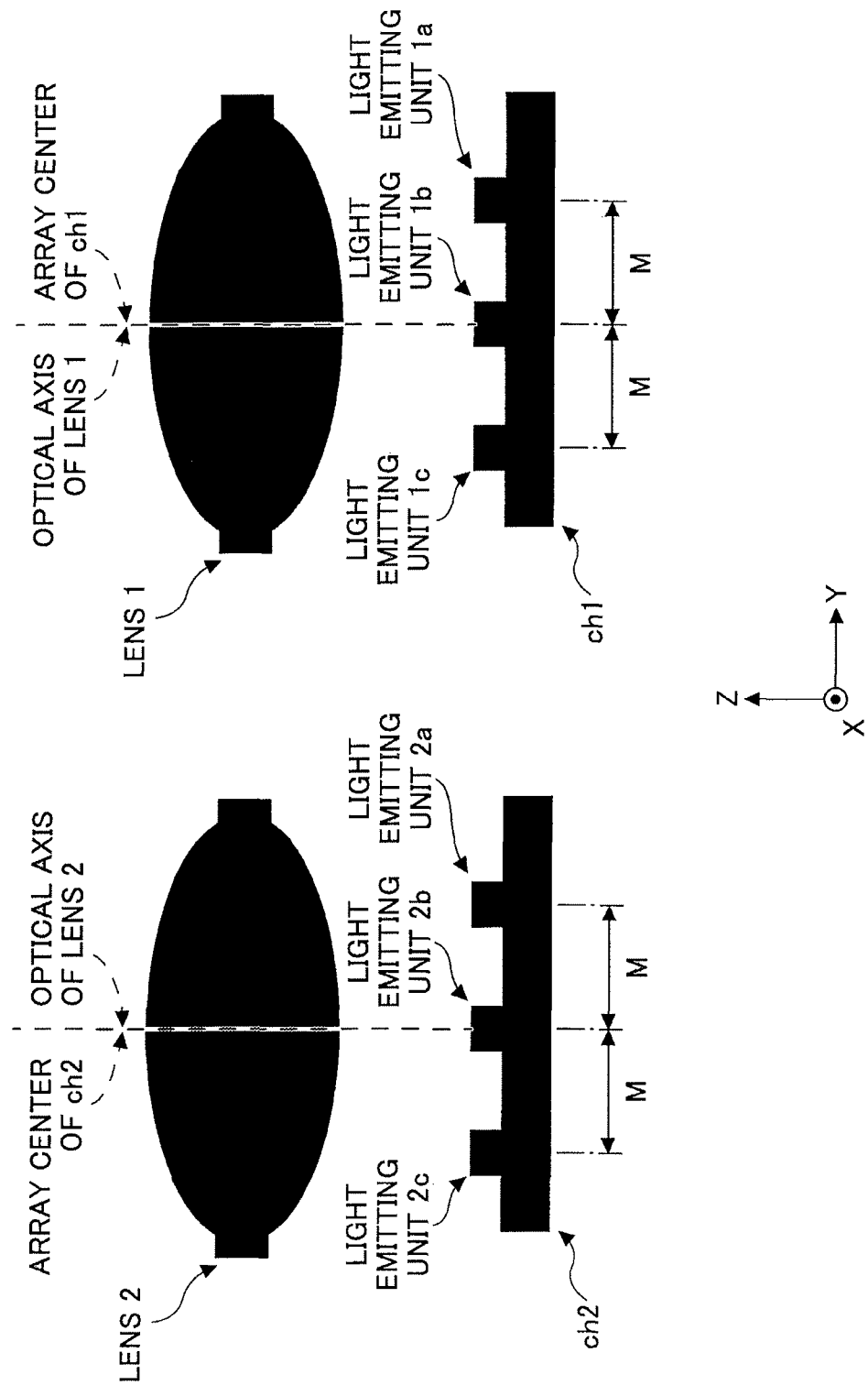

[Fig. 19]
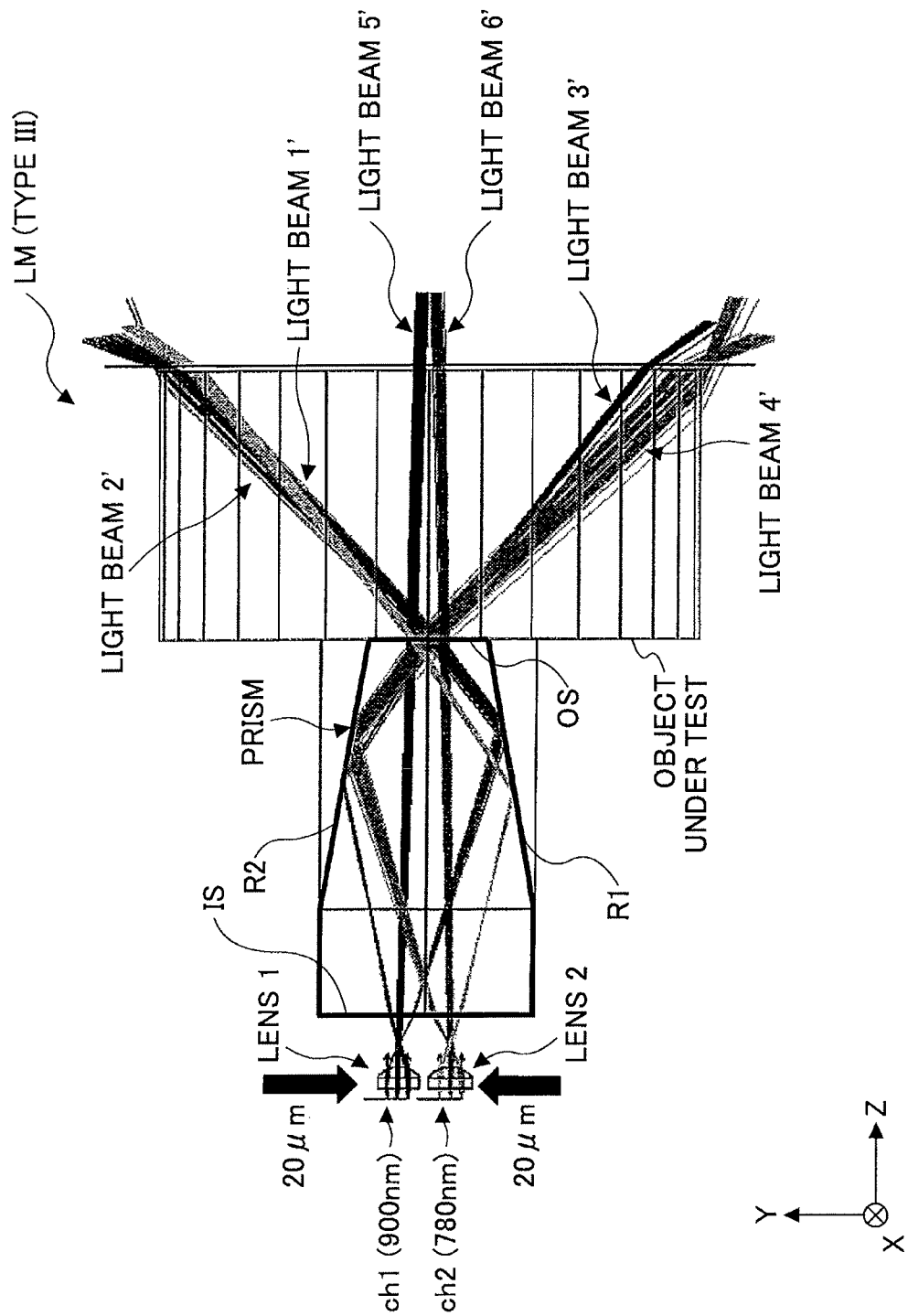

[Fig. 20]
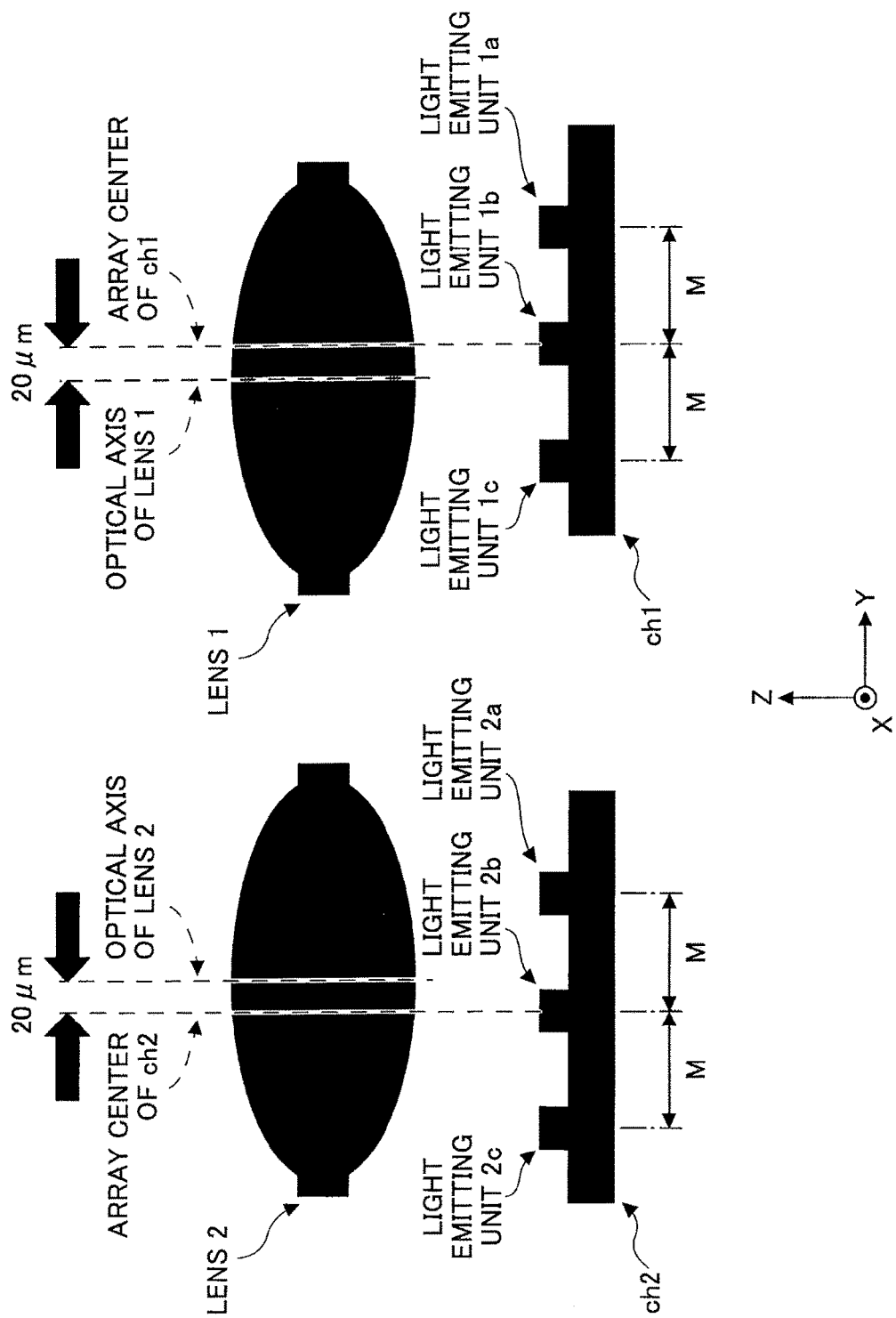

[Fig. 21]
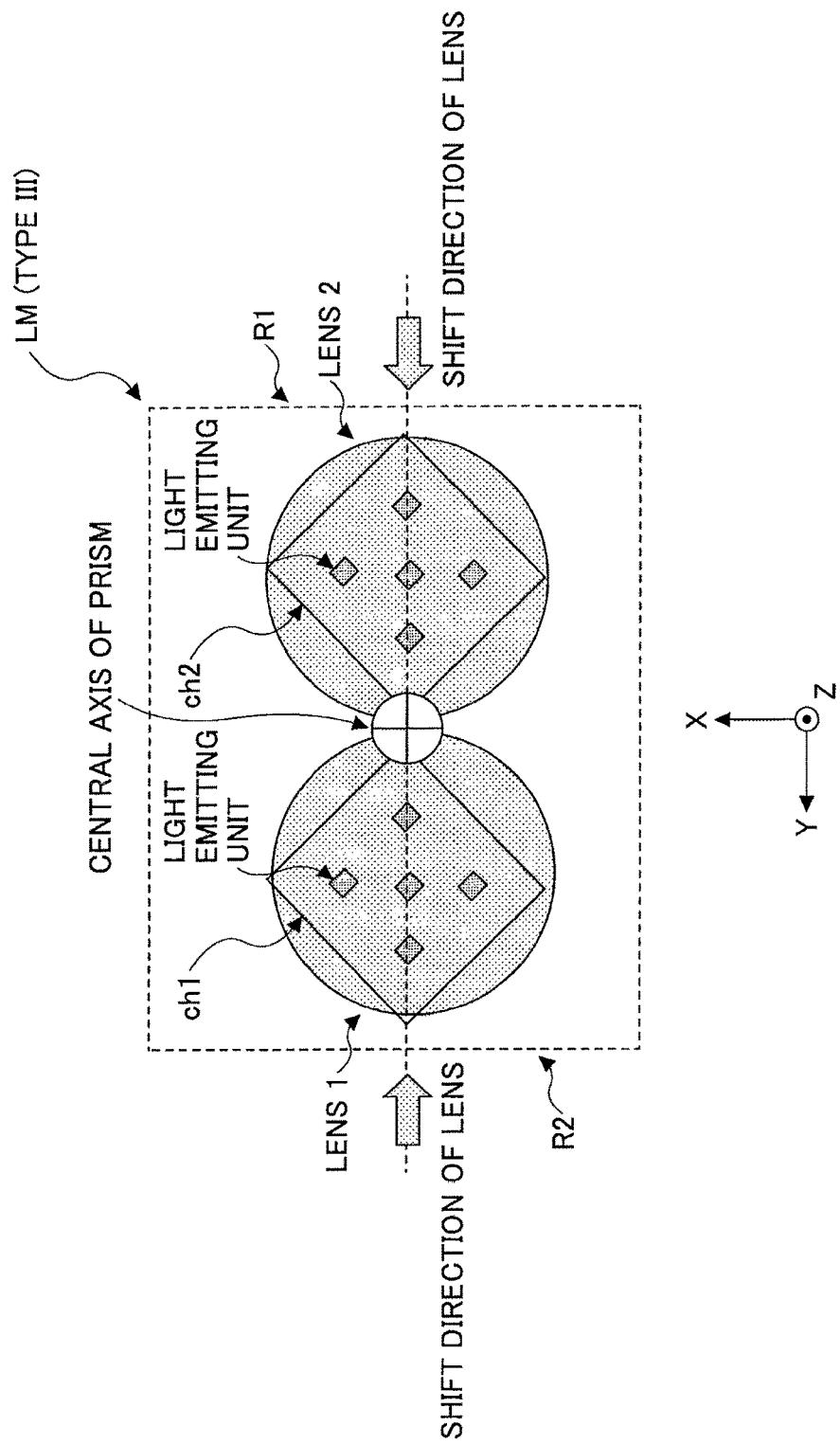

[Fig. 22]
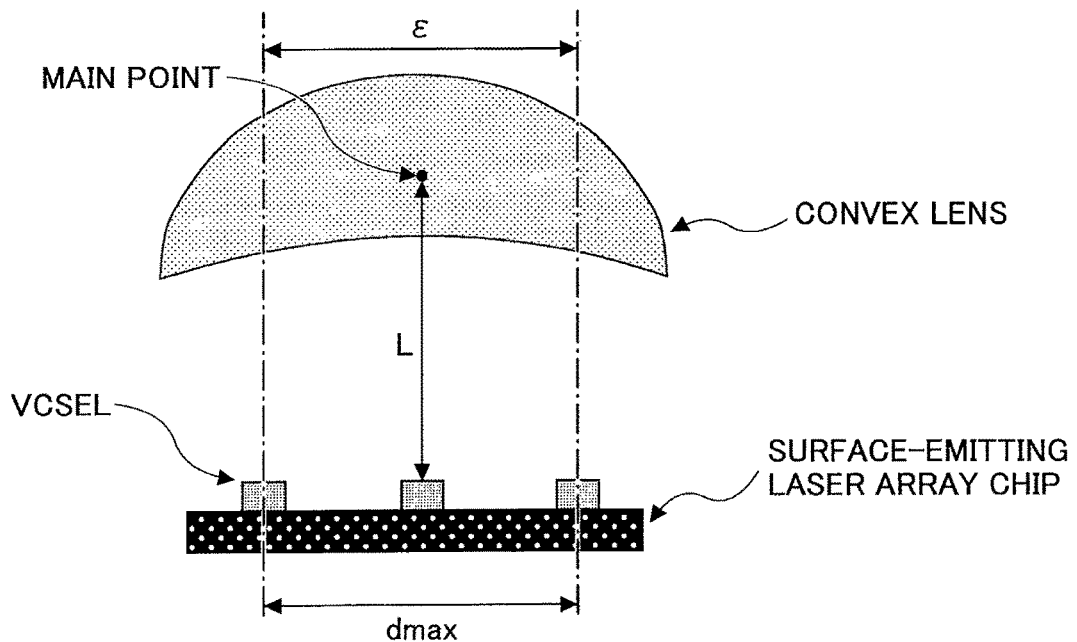
[Fig. 23]
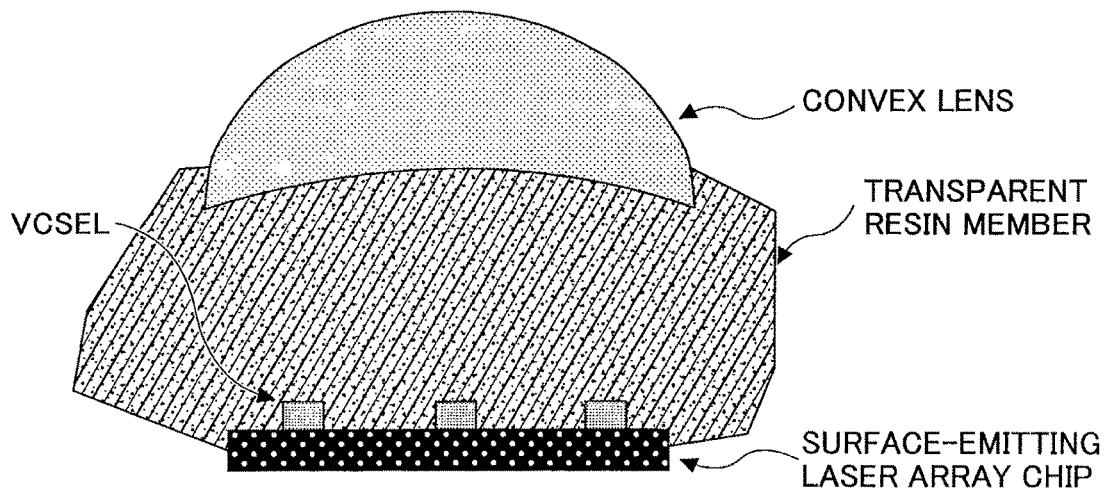

[Fig. 24]
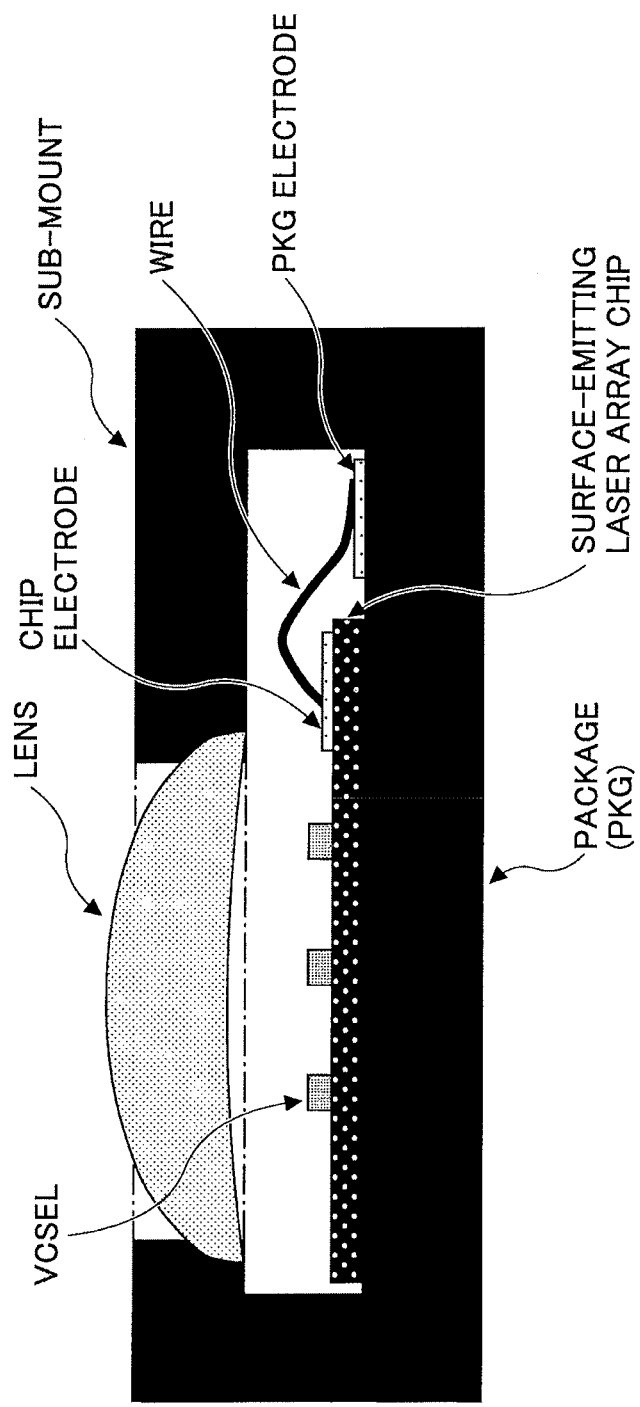

[Fig. 25]
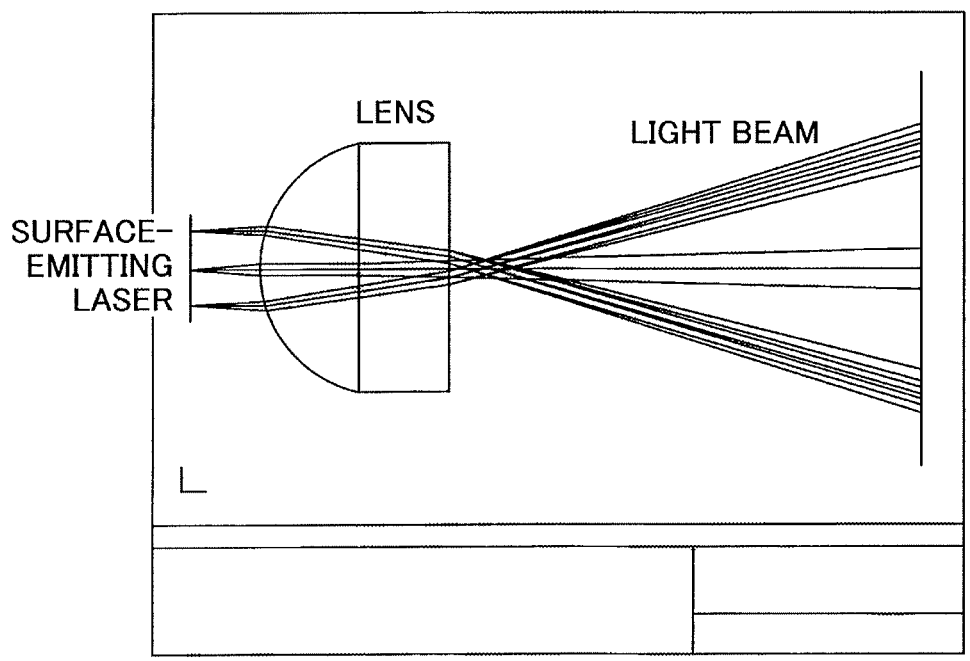

[Fig. 26]
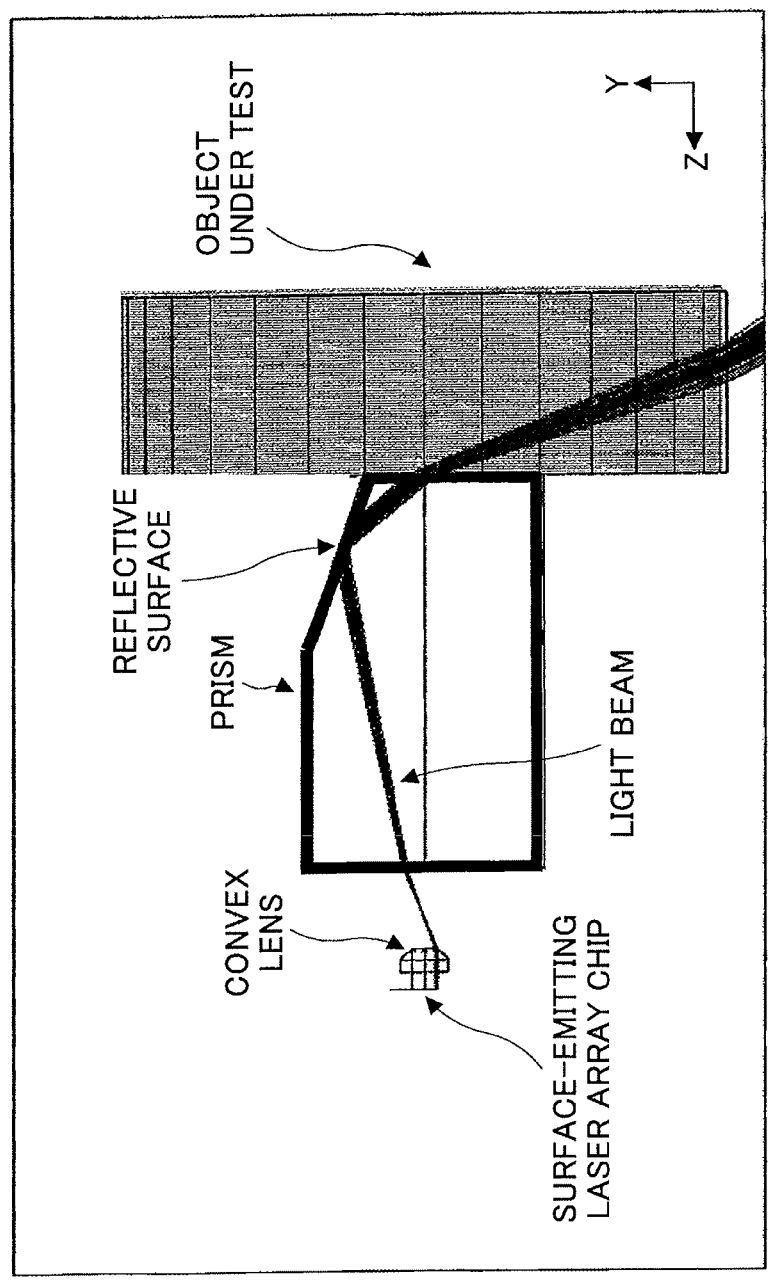

[Fig. 27]
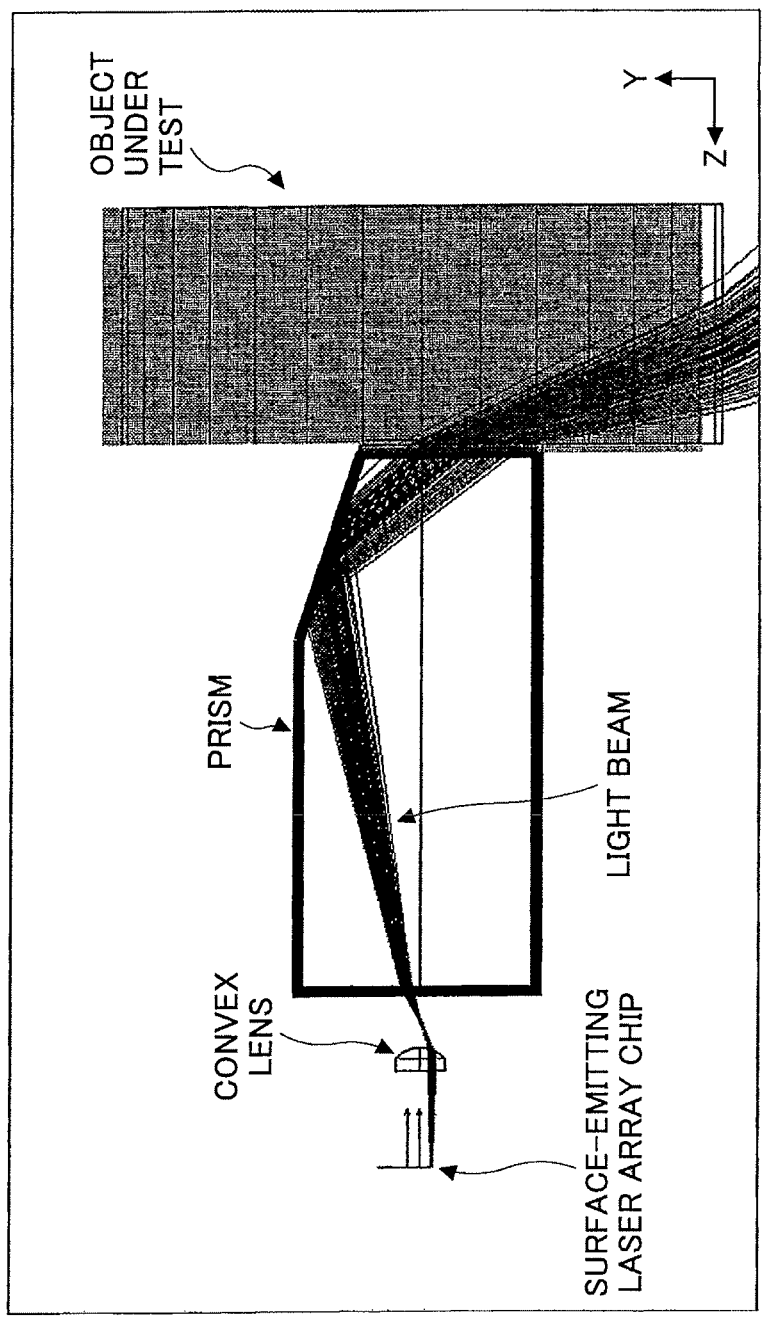

[Fig. 28A]
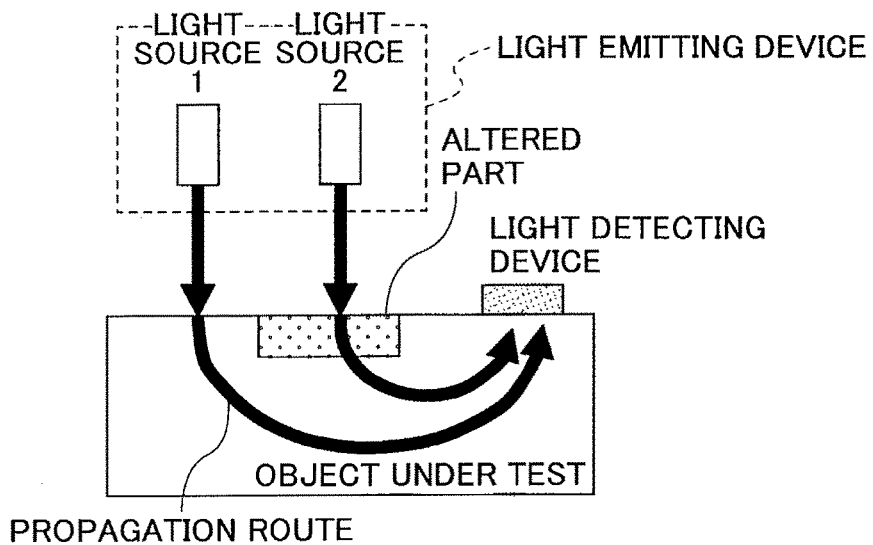
[Fig. 28B]
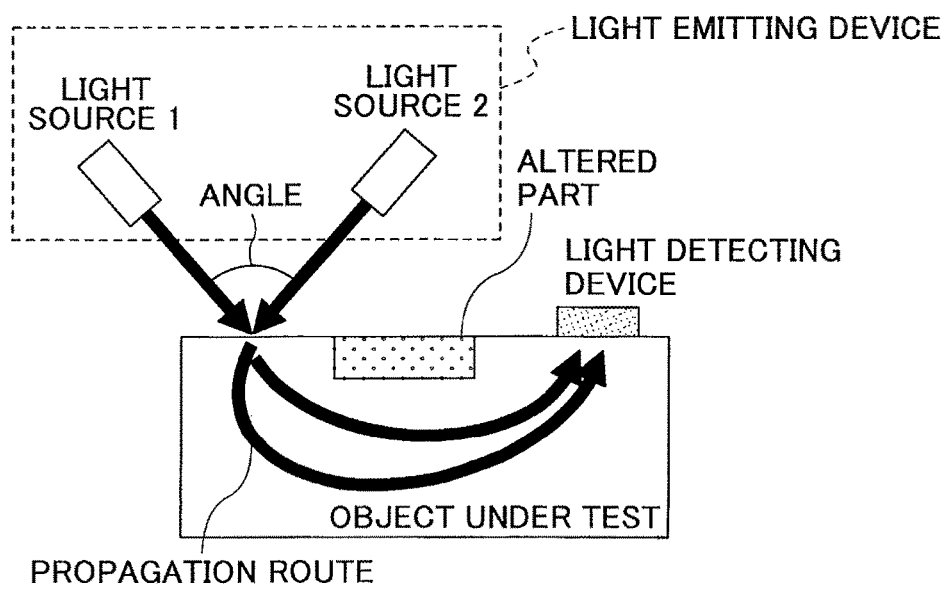

[Fig. 29]
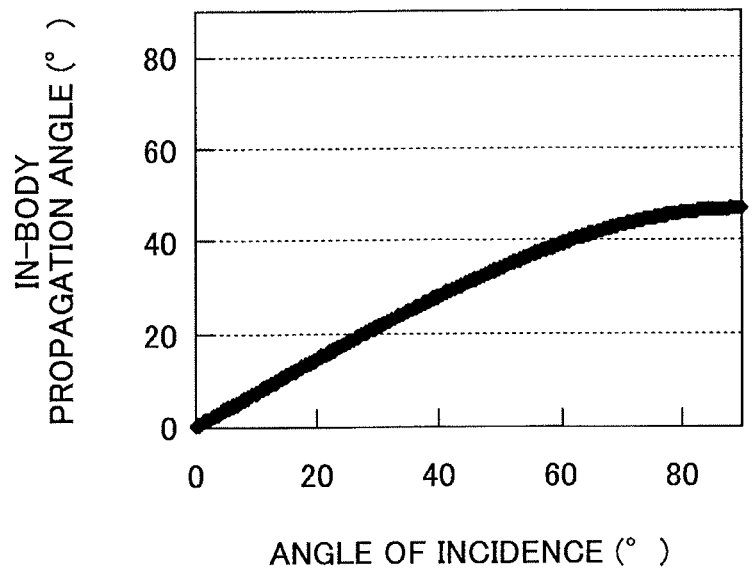
[Fig. 30]

[Fig. 31]
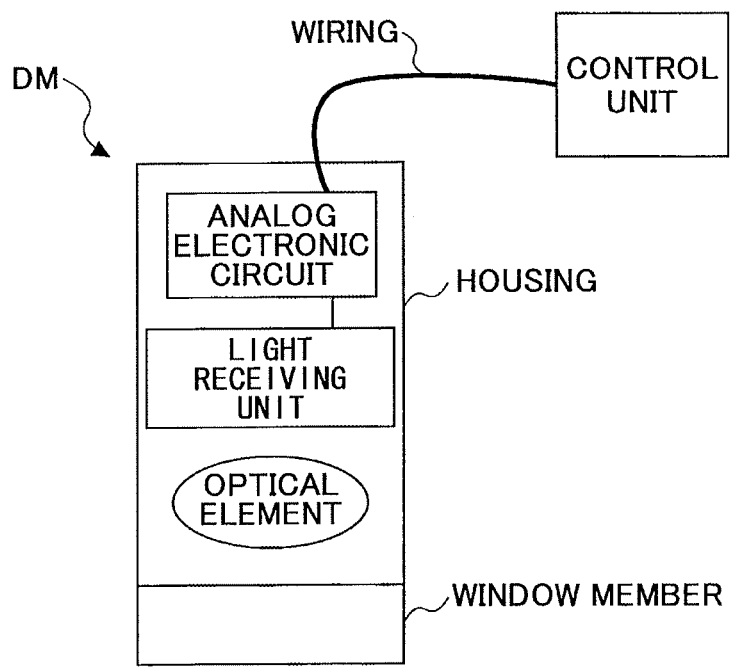
[Fig. 32]
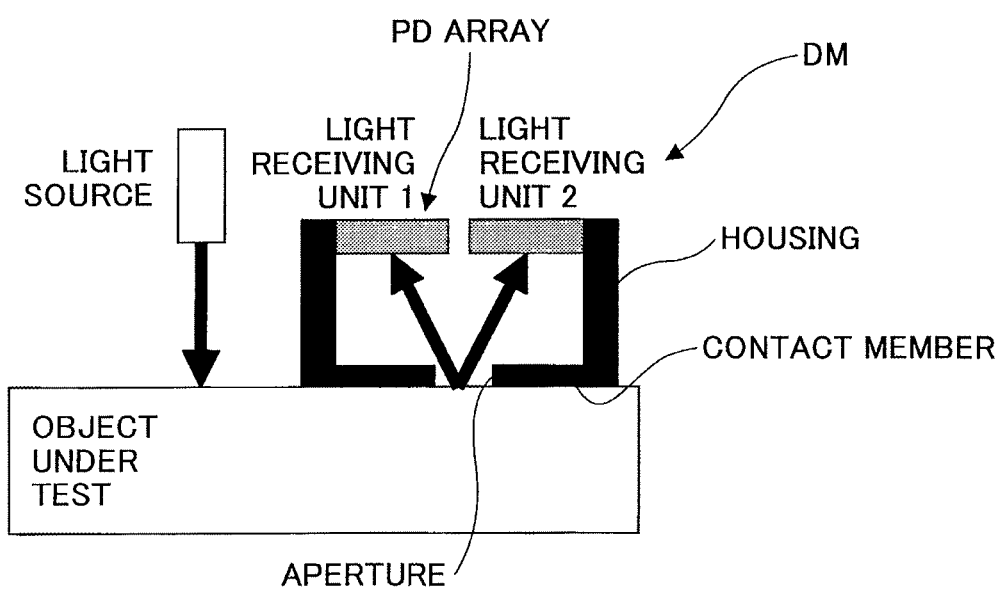

[Fig. 33]
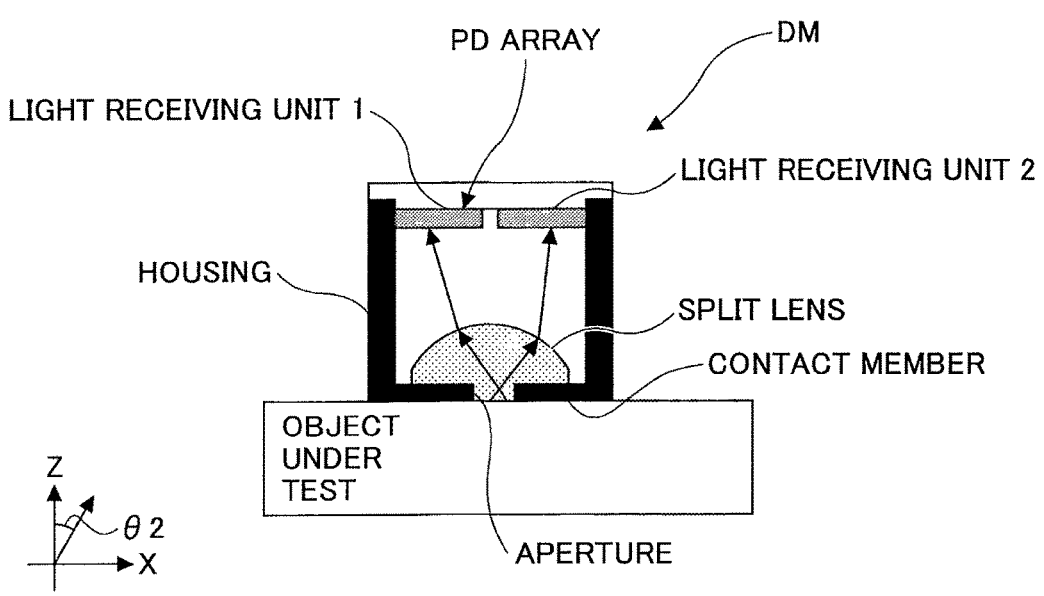

[Fig. 34]
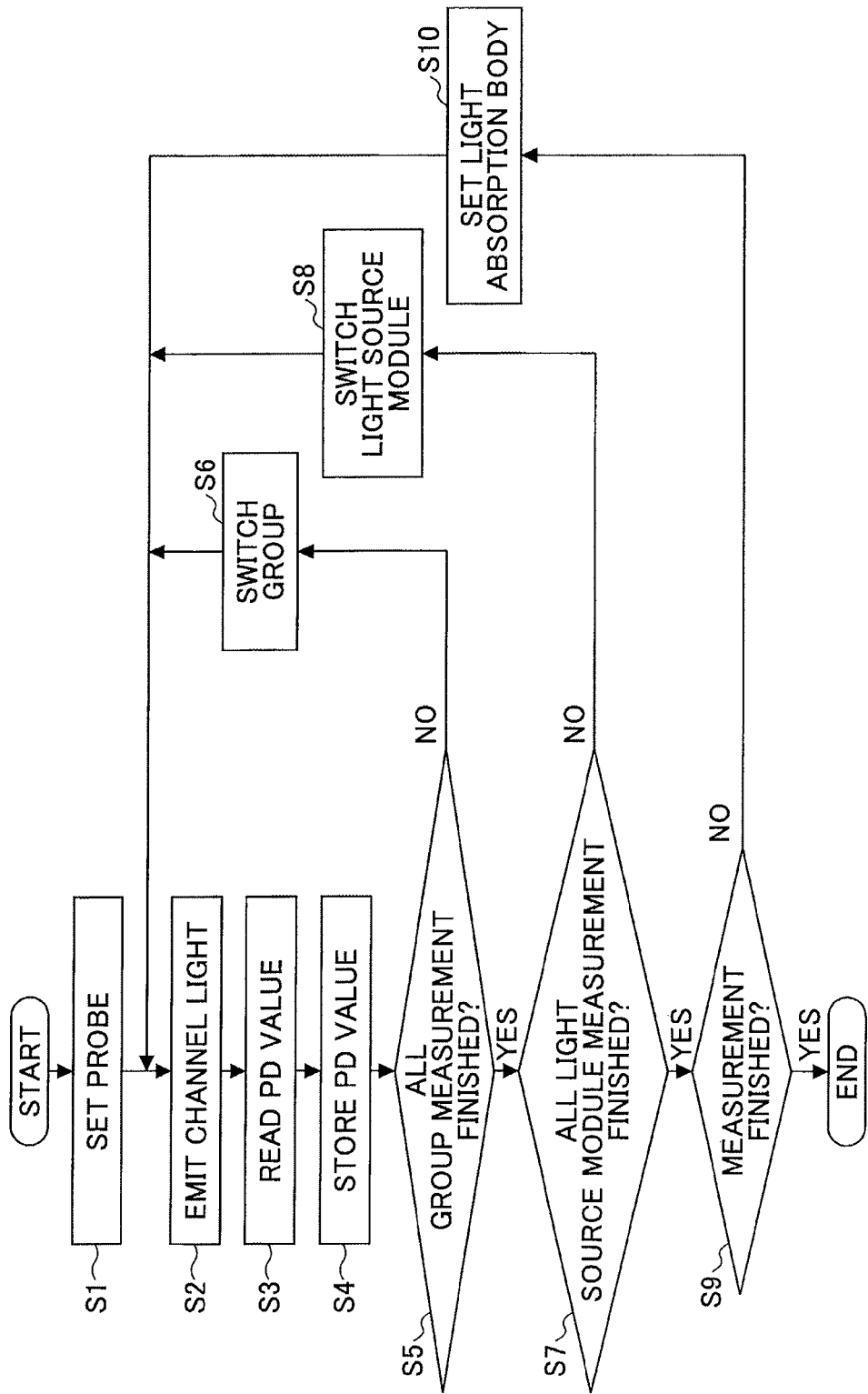

[Fig. 35]
| DEPTH (mm) | COMPARATIVE EXAMPLE | EXAMPLE 2 |
|---|---|---|
| 2 | × | ○ |
| 4 | × | ○ |
| 6 | × | ○ |
| 8 | × | ○ |
| 10 | × | ○ |
| 12 | × | ○ |
| 14 | × | ○ |
| 16 | × | ○ |
| 17 | × | × |
[Fig. 36]
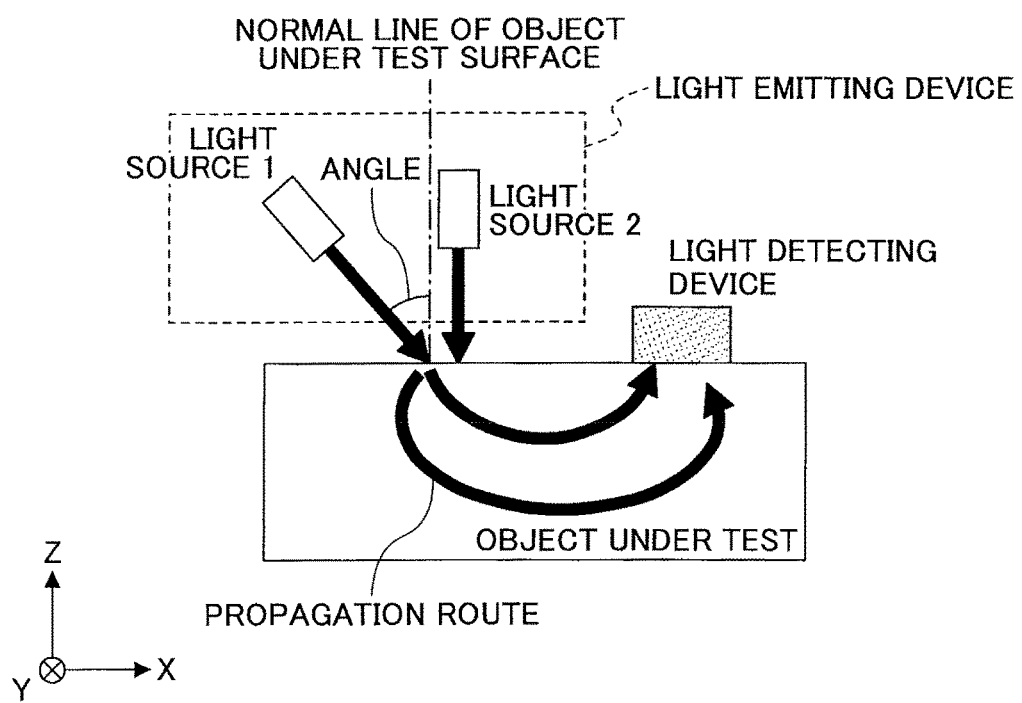

[Fig. 37]
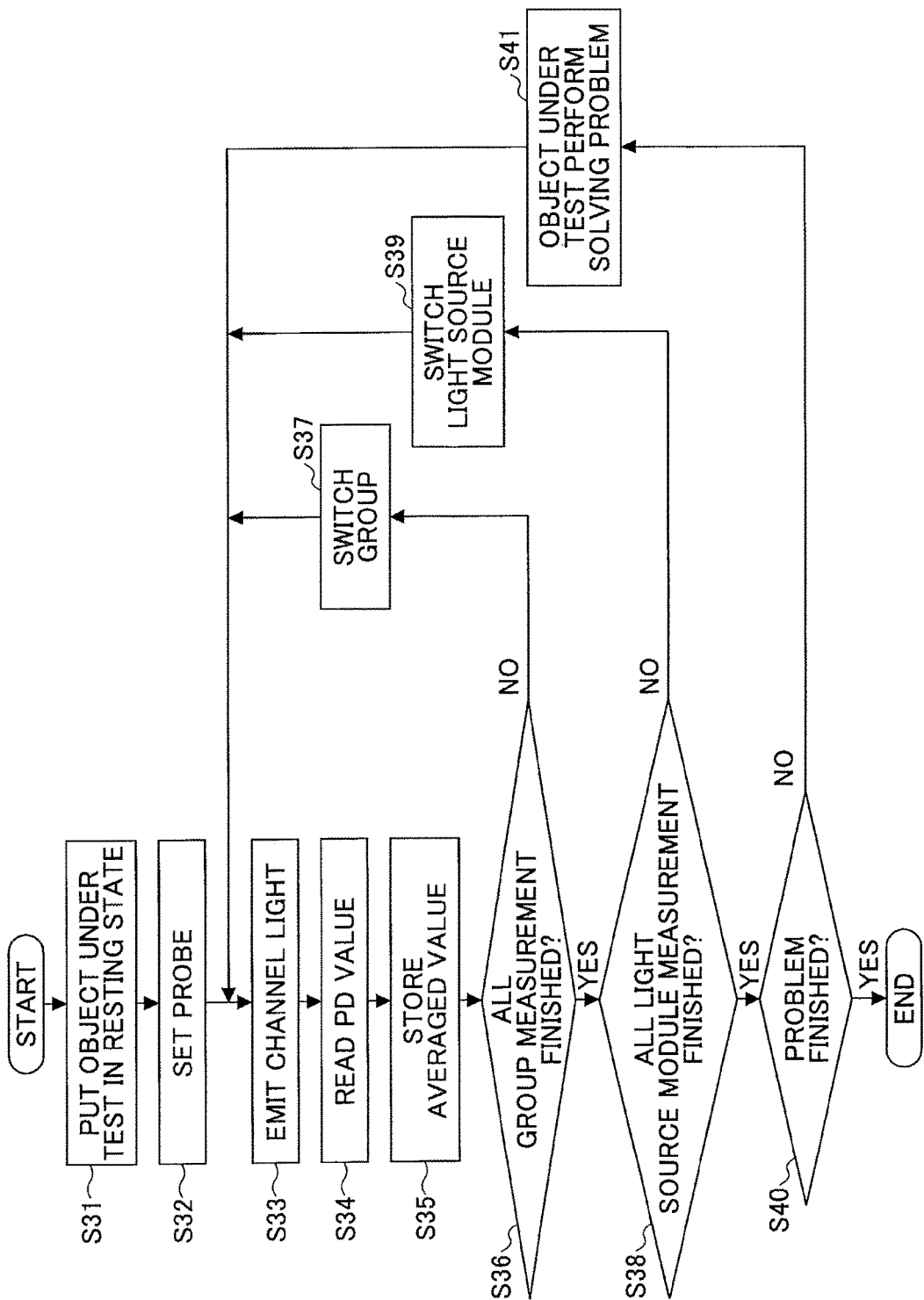

[Fig. 38]
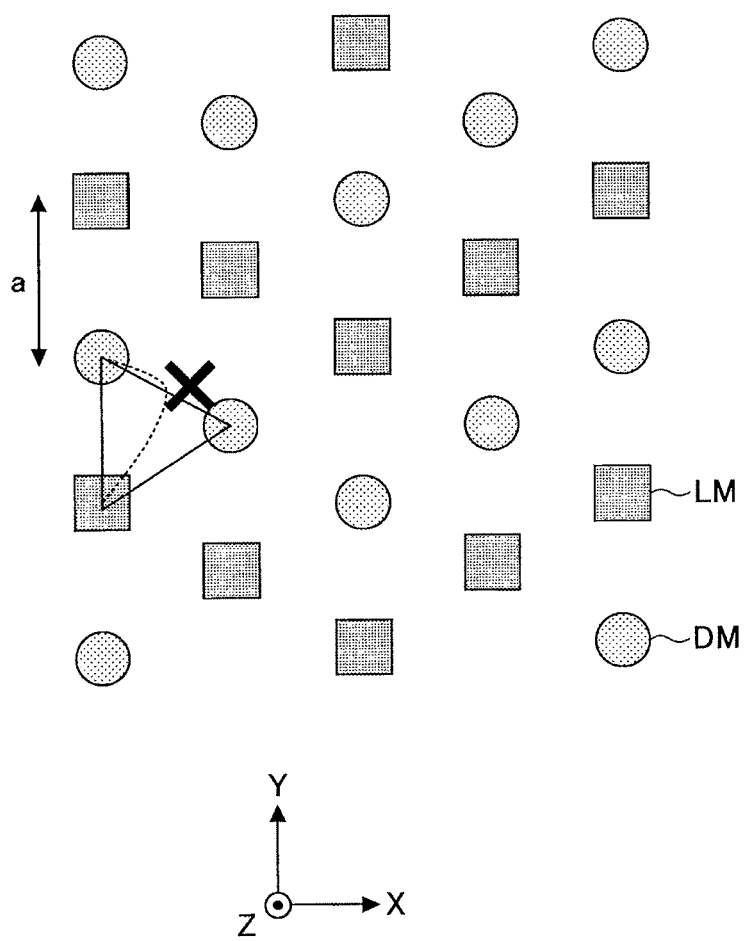

[Fig. 39]
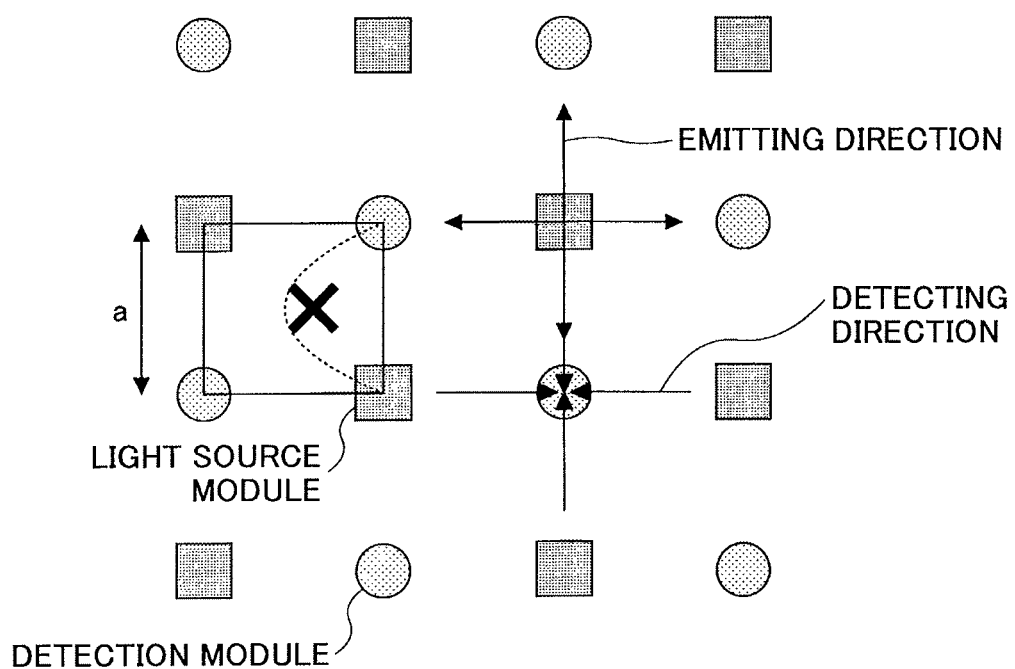

[Fig. 40A]
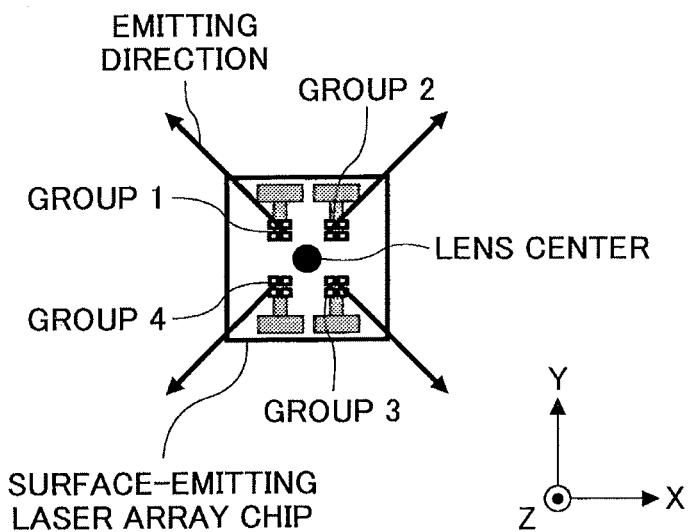
[Fig. 40B]
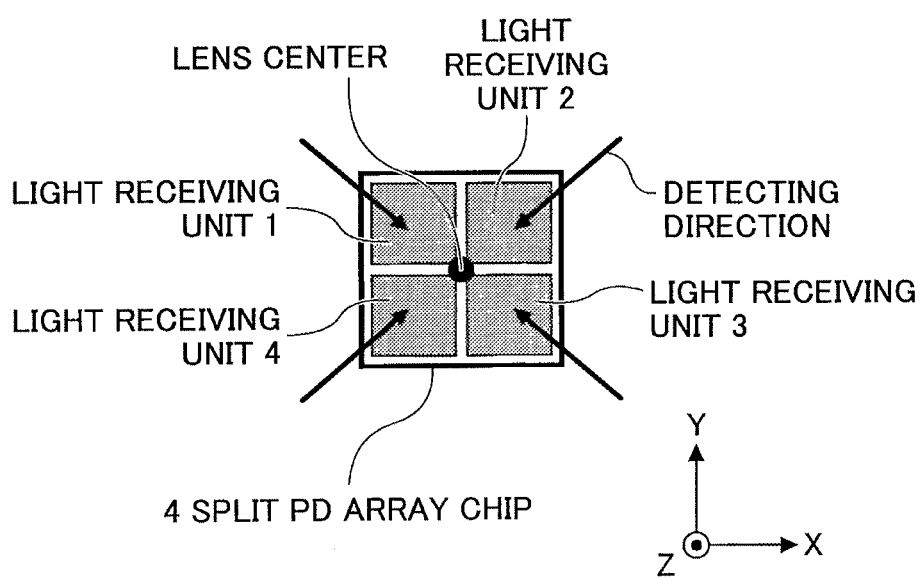

[Fig. 41]
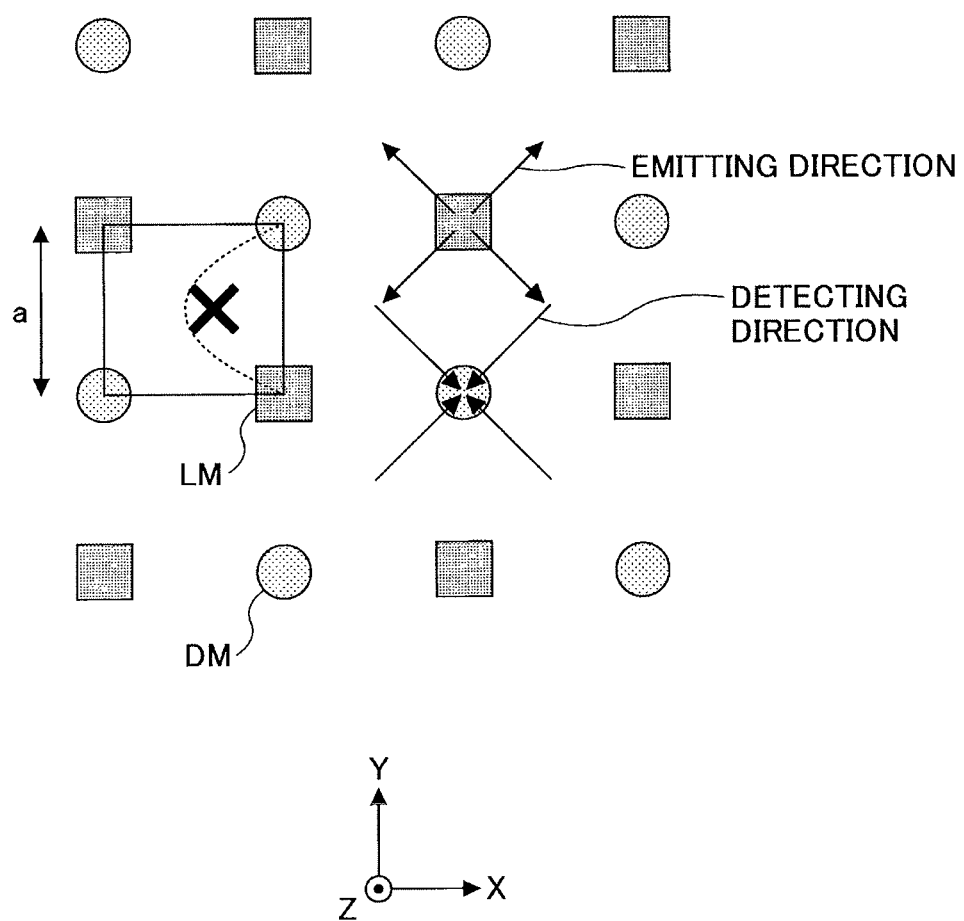

[Fig. 42]
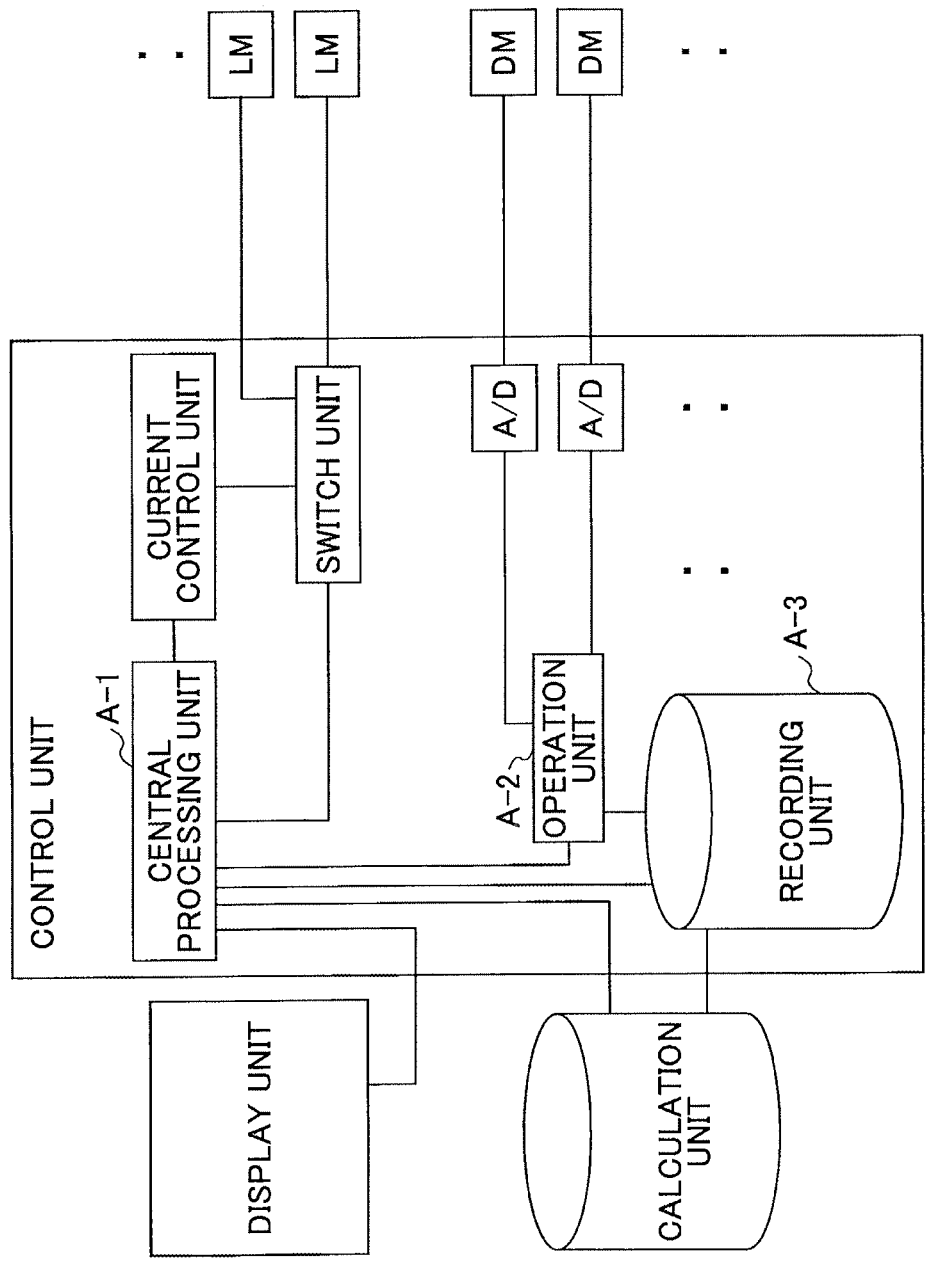

[Fig. 43]
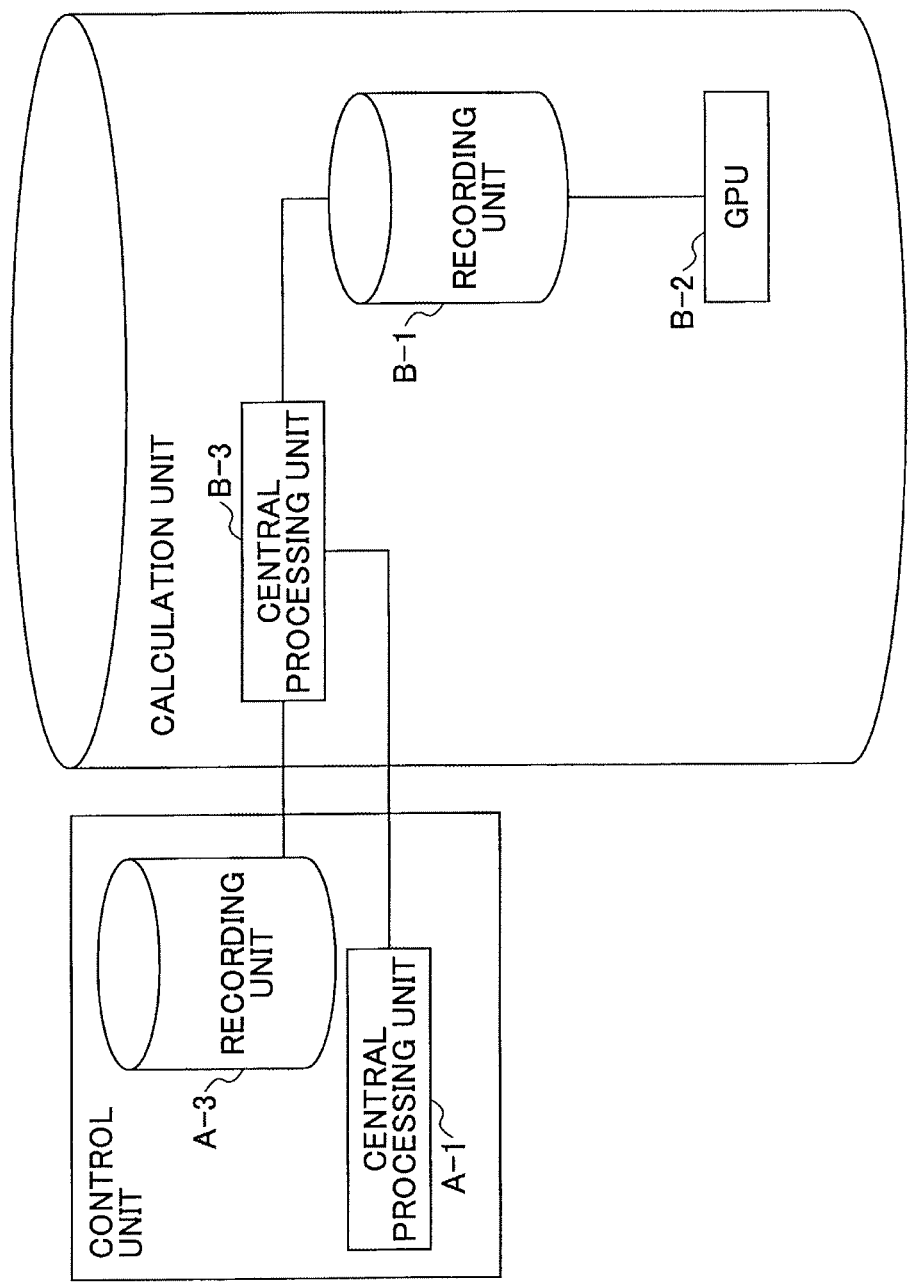

OPTICAL SENSOR, OPTICAL TESTING APPARATUS, AND OPTICAL CHARACTERISTICS DETECTION METHOD

TECHNICAL FIELD

The present invention relates to an optical sensor, an optical testing apparatus, and an optical characteristics detection method, and in particular, an optical sensor including an emitting system which emits light onto an object under test (object) and a detecting system which detects the light which is emitted by the emitting system, and which has propagated through the object under test, an optical testing apparatus including the optical sensor, and an optical characteristics detection method using the optical sensor.

BACKGROUND ART

Conventionally, an optical measurement apparatus for living body is known, which measures information in the object under test by emitting light onto an object under test (living body) and detecting the light which has propagated through the object under test (e.g., refer to Patent Document 1).

The optical measurement apparatus for living body disclosed in Patent Document 1 is not capable of measuring information in the object under test with high accuracy.

SUMMARY OF INVENTION

An embodiment of the present invention discloses an optical sensor which includes an emitting system including at least one light emitting device which emits light onto an object under test and a detecting system detecting the light which is emitted by the emitting system and which has propagated through the object under test, which light emitting device is capable of emitting a plurality of light beams with different wavelengths onto substantially the same position of the object under test.

According to the embodiment of the present invention, it is possible to measure information in an object under test with high accuracy.

BRIEF DESCRIPTION OF DRAWINGS

FIG. 1 is a drawing illustrating a schematic configuration of an optical testing apparatus according to a first embodiment of the present invention.

FIG. 2 is a drawing illustrating a water tank for a phantom.

FIG. 3 is a drawing illustrating a layout of transparent windows.

FIG. 4 is a first drawing illustrating a schematic configuration of a light source module according to an example 1.

FIG. 5 is a drawing illustrating a schematic configuration of a detection module according to an example 1.

FIG. 6 is a second drawing illustrating a schematic configuration of the light source module according to the example 1.

FIG. 7 is a drawing illustrating in-body propagation angles.

FIG. 8 is a flowchart illustrating a method for measuring information in an object under test.

FIG. 9 is a flowchart related to an inverse problem estimation algorithm.

FIG. 10 is a first drawing illustrating sensitivity distribution in a photo diode (PD).

FIG. 11 is a second drawing illustrating sensitivity distribution in a PD.

FIG. 12 is a drawing illustrating in-body propagation angles.

FIG. 13A is a drawing illustrating an actual position of a light absorption body.

FIG. 13B is a drawing illustrating an estimation result of the position of the light absorption body.

FIG. 13C is a drawing illustrating a detection result of the position of the light absorption body in a comparative example.

FIG. 14A is a drawing illustrating an actual position of the light absorption body after movement.

FIG. 14B is a drawing illustrating an estimation result of the position of the light absorption body after movement.

FIG. 14C is a drawing illustrating a detection result of the position of the light absorption body in a comparative example.

FIG. 15 is a drawing illustrating an arrangement of a plurality of light source modules and a plurality of detection modules in an optical sensor according to an example 2.

FIG. 16 is a drawing illustrating a light source module LM (type I) according to the example 2.

FIG. 17 is a drawing illustrating a surface emitting laser array chip of the light source module LM (Type I) according to the example 2.

FIG. 18A is a first drawing illustrating a light source module ML (Type II) according to the example 2.

FIG. 18B is a second drawing illustrating the light source module ML (Type II) according to the example 2.

FIG. 19 is a drawing illustrating a light source module LM (Type III) according to the example 2.

FIG. 20 is a drawing illustrating position relationships between lenses and surface emitting laser array chips in the light source module LM (Type III) according to the example 2.

FIG. 21 is a drawing illustrating position relationships among the lenses, the surface emitting laser array chips, and a prism in the light source module LM (Type III) according to the example 2.

FIG. 22 is a first drawing illustrating an additional configuration of a light source module according to the examples 1 and 2.

FIG. 23 is a second drawing illustrating the additional configuration of the light source module according to the examples 1 and 2.

FIG. 24 is a third drawing illustrating the additional configuration of the light source module according to the examples 1 and 2.

FIG. 25 is a light beam drawing optically designed by an optical simulator.

FIG. 26 is a drawing illustrating a result of an optical simulation according to a first embodiment.

FIG. 27 is a drawing illustrating a result of an optical simulation according to a comparative example.

FIG. 28A is a drawing illustrating an operation of an optical sensor according to a comparative example.

FIG. 28B is a drawing illustrating an operation of an optical sensor according to the first embodiment.

FIG. 29 is a graph illustrating a relationship between an incidence angle from air to a living body and an in-body propagation angle.

FIG. 30 is a graph illustrating a relationship between an incidence angle from a resin to a living body and an in-body propagation angle.

FIG. 31 is a first drawing illustrating a schematic configuration of a detection module according to the example 2.

FIG. 32 is a second drawing illustrating a schematic configuration of a detection module according to the example 2.

FIG. 33 is a third drawing illustrating a schematic configuration of a detection module according to the example 2.

FIG. 34 is a flowchart illustrating an optical characteristics detection method (position measurement method) according to the example 2.

FIG. 35 is a drawing illustrating an estimation result of an inverse problem estimation according to the example 2.

FIG. 36 is a drawing illustrating an operation of an optical sensor according to the first embodiment.

FIG. 37 is a flowchart illustrating an optical characteristics detection method (position measurement method) according to the second embodiment.

FIG. 38 is a drawing illustrating an arrangement of a plurality of light source modules and a plurality of detection modules in an optical sensor according to a third embodiment.

FIG. 39 is a drawing illustrating emitting directions of a light source module and detection directions of a detection module in an optical sensor according to a comparative example.

FIG. 40A is a drawing illustrating emitting directions of four surface emitting laser array chips according to a fourth embodiment.

FIG. 40B is a drawing illustrating detection directions of four PDs of a PD array according to the fourth embodiment.

FIG. 41 is a drawing illustrating emitting directions of a light source module and detection directions of a detection module in an optical sensor according to the fourth embodiment.

FIG. 42 is a block diagram of a control unit.

FIG. 43 is a block diagram of a calculation unit.

DESCRIPTION OF EMBODIMENTS

First Embodiment

In the following, a first embodiment of the present invention will be described referring to FIG. 1 through FIG. 36. FIG. 1 illustrates a schematic configuration of an optical testing apparatus 100 according to a first embodiment.

The optical testing apparatus 100 is used in, as an example, diffuse optical tomography (DOT). The DOT is a technique in which light is emitted onto an object under test (scattering body) such as a living body and the light that has propagated through the object under test is detected, so that optical characteristics in the object under test are estimated. Especially, it is expected to be used for assisting in differential diagnosis of depression, and used as auxiliary equipment for rehabilitation, by detecting blood flow in a brain. In the DOT, when the resolution is improved, it becomes possible to recognize brain functions in detail. Due to this reason, many research institutions have been actively conducting research for the improvement of the resolution.

As illustrated in FIG. 1, the optical testing device 100 includes an optical sensor 10, a control unit, a display unit, a calculation unit, etc. The optical sensor 10 includes a light source module LM and a detection module DM. The light source module LM includes a plurality of light emitting units. The control unit has a configuration as illustrated in a block diagram of FIG. 42. In the control unit, a switch unit is controlled by information from a central processing unit A-1, and the light source module LM which should emit light is selected. At this time, the current which is supplied to the light source module LM via the switch unit is controlled to be a desired value by a current control unit. A detection result (data) in the detection module DM is A/D converted, and operations such as an averaging process are performed by an operation unit (A-2). The operation results at the operation unit (A-2) are sequentially recorded in a recording unit (A-3).

In the present specification, a term "probe" may be used in the case where the light source module LM and the detection module DM are not distinguished from each other. Further, in the present specification, terms "pseudo living body", "living body", and "object under test" are used appropriately, but it should be noted that the "pseudo living body" and the "living body" are examples of the "object under test".

The optical sensor 10 can be generally used as a sensor for detecting a light absorption body in an object under test, but the object under test which has the highest utility value is a living body. However, it is not always easy to detect a position of blood flow (light absorption body) in a living body by using an optical sensor. Therefore, when a living body is used as an object under test, it is difficult to check the effect (detection accuracy) of the optical sensor.

Therefore, in the present embodiment, a pseudo living body (also referred to as "phantom") which is a cloudy (white turbid) liquid contained in a water tank is employed as an object under test which can ensure versatility, and it is easy to check the detection accuracy.

In the following, an example 1 according to the present embodiment will be described.

EXAMPLE 1

In the example 1, a method is employed in which light beams from light emitting units are deflected by a prism and angles of the light beams incident on an object under test are different from each other.

Here, as illustrated in FIG. 2, transparent windows made of transparent acrylic plates are arranged at eight positions on a side wall (+z side wall) of a water tank including walls made of black acrylic plates. The inside of the water tank is filled with an intralipid water solution (10% concentration intralipid diluted with water 10-fold). In other words, the pseudo living body used in the example 1 is the intralipid water solution.

Black ink is dropped in the intralipid water solution which the water tank is filled with in such a way that the black ink is approximately 20 ppm and the absorption coefficient and the scattering coefficient are substantially the same as those of a living body. Further, a light absorption body having black color which simulates blood flow is dipped into the cloudy intralipid water solution. Here, it is assumed that the light absorption body is a black spherical object having a diameter of approximately 5 mm such as black polyacetal. In order to control the position of the spherical object, the spherical object is fixed to a thin metal bar having a diameter of 1 mm connected to an automatic stage. The probes are attached to the transparent windows, and the positions of the probes are accurately determined.

Here, the volume (size) of the water tank is 140 mm×140 mm×60 mm. The thickness of the black acrylic plates is 4 mm. The eight transparent windows include two types of circular transparent windows A and B having different sizes from each other (refer to FIG. 3). There are four transparent windows A and four transparent windows B. The diameter of the transparent window A is 9 mm, and the diameter of the transparent window B is 12 mm. Both the thickness of the transparent window A and the thickness of the transparent window B are 1.5 mm.

FIG. 3 illustrates a layout of the eight transparent windows. The eight transparent windows are arranged in a grid pattern so that the transparent windows A and B are arranged next to each other at the same distances in X axis and Y axis directions. Here, the detection modules DM are attached to the transparent windows A and the light source modules LM are attached to the transparent windows B (B1 through B4). The distance between the centers of the adjacent transparent windows is 30 mm.

As illustrated in FIG. 4, the light source module LM includes a lens, a prism, a ceramic package (not shown) on which a surface emitting laser array chip is mounted, a flexible printed circuit board (not shown) on which the ceramic package and an analog electronic circuit are mounted, wirings and connector units (not shown) connected to the flexible printed circuit board, a housing containing the above elements, a window member made of a transparent resin which is used to be in contact with an object under test, etc. In the light source module LM, a power supply unit (not shown) controls a current value appropriately in such a way that a light amount of the light emitting unit can be maintained to be constant. The light source module LM is installed in a state where the window member is in contact with the object under test (transparent window B) from the +z side.

As illustrated in FIG. 5, the detection module DM includes a housing made of a black resin, a contact member attached to the head (the end of −z side) of the housing and made of an elastic body, a hemispherical lens (split lens) contained in the housing and having a diameter of 3 mm, a four-split PD array (four photodiodes (PD) are arranged in the form of an array), etc. Apertures (openings) are formed at the end of the housing and in the contact member. The detection module LM is installed in a state where the contact member is in contact with the object under test (transparent window A) from the +z side. It should be noted that in FIG. 5, only two of four PDs (light receiving unit) are illustrated.

The split lens is arranged near the +z side of the aperture. Here, the light, which is emitted from the light source module LM onto the object under test and which has propagated through the object under test, is incident on the split lens via the aperture, is reflected and transmitted in the direction according to the incidence position on the split lens and the incidence direction (refer to FIG. 5).

The four-split PD array is arranged on the +z side of the split lens. Here, the light passing through the split lens is incident on any one of the four light receiving units (PD) of the four-split PD array according to the traveling direction (emitting direction from the split lens). In this way, in the detection module DM, it becomes possible to classify the incidence angle of the light coming from the object under test into four angle ranges.

The control unit detects light receiving amounts of the four PDs (light receiving units) of the detection modules DM installed in the transparent windows A (light receiving amounts of the total 16 PDs). The data are detected at a sampling rate of 1 ms, and the values measured during 20 s are averaged. In a single measurement, the data of 16 PDs are obtained.

Next, the light source module LM will be described in detail. A 40 ch surface emitting laser array chip is employed as a light source of the light source module LM. The surface emitting laser array chip has 40 VCSELs (vertical cavity surface emitting lasers) as light emitting units.

On the optical path of the light from the surface emitting laser array chip, a lens having a diameter of 3 mm is arranged in such a way that the light becomes substantially parallel light (refer to FIG. 6).

The distance between the emitting surface (light emitting surface) of the surface emitting laser array chip and the main point of the lens (the optical center of the lens) is set to be equal to the focal length f (e.g., 9 mm) of the lens. In other words, the surface emitting laser array chip is arranged in such a way that the emitting surface is positioned at the position of the focal point of the lens. It should be noted that the "focal length of a lens" is a distance between the main point and the focal point of the lens.

Here, the 40 ch of the VCSELs simultaneously emit light and the total output is approximately 50 mW. The parallel light beams emitted from the VCSELs are deflected by the prism as illustrated in FIG. 6.

As the prism, an acrylic prism having the refractive index substantially equal to that of the acrylic water tank is employed. The reflecting surface of the prism is designed according to the diameter of the prism, and the angle of the reflecting surface is set in such a way that the light that passes through the lens is incident on the acrylic water tank with the incidence angle of approximately 50 degrees.

A difference in refractive index between the acrylic of the water tank and the prism and the phantom (i.e., the intralipid water solution) is set in such a way that the propagation angle in the phantom is approximately 60 degrees ($\theta 1$ in FIG. 6) according to Snell's law. The prism is installed in a rotatable stage (not shown) which is arranged on an inner wall of the water tank and is rotatable around a rotational axis extending in the Z axis direction.

By rotating the rotatable stage together with the prism, it becomes possible to change the incidence angle of the light on the prism and the orientation of the incidence light. Here, as illustrated in FIG. 7, measurement is performed sequentially for four orientations (i.e., +X, −X, +Y, and −Y orientations). In other words, 16 measurements are performed including four positions (four from B1 to B4) of the light source module LM times four directions. Between the prism and the water tank, a gel resin (not shown) having the refractive index substantially equal to that of the prism and the water tank is supplied. By having the above gel resin, refraction and reflection can be prevented between the prism and the water tank.

Next, a method for measuring information in the object under test will be described referring to a flowchart illustrated in FIG. 8.

First, probes are set (step T1). The probe means, as described above, the detection module DM or the light source module LM. The probes to be set here are four detection modules DM and one light source module LM. The four detection modules DM are attached to four transparent windows A having the diameter of 9 mm as illustrated in FIG. 3, respectively. The one light source module LM is attached to the transparent window B1 as illustrated in FIG. 3.

Next, the 40 channels (light emitting units) of the light source module LM are caused to emit light (step T2). The current value is determined in such a way that the total emission intensity is approximately 50 mW. The light emitting duration is approximately 20 s, during which the PD detection values of the four detection modules DM are read (step T3), and several points of the data (detection values) detected every 1 ms interval are averaged. Further, the averaged detection values (i.e., average values of the detection values) are stored in the recording unit (step T4).

Next, a wavelength of the emitting light is switched and steps T2 through T4 are performed again (steps T5 and T6). Here, the wavelengths of 780 nm and 900 nm can be selected. Specifically, by preparing two types of light source modules LM with different oscillation wavelengths (780 nm band and 900 nm band) in advance and by switching the light source modules LM, the wavelength switching of the emitting light can be performed.

Here, the measurements are performed for four orientations including +X direction, +Y direction, −X direction, and −Y direction (steps T7 and T8). Specifically, steps T2 through T6 right after step T1 are performed in a state where the prism is arranged in +X direction. Next, by rotating the prism, the prism is arranged in +Y direction. Steps T2 through T6 are performed while the prism is in this state. Next, by rotating the prism, the prism is arranged in −X direction. Steps T2 through T6 are performed while the prism is in this state. Next, by rotating the prism, the prism is arranged in −Y direction. Steps T2 through T6 are performed while the prism is in this state.

Next, the attaching position of the light source module LM is sequentially changed from the transparent window B1 to the transparent windows B2, B3, and B4 in this order, and four orientation measurements are performed for each of the positions (steps T9 and T10). After that, the position of the light absorption body is moved and the four orientation measurements are performed for each of the four attaching positions of the light source module LM (steps T11 and T12).

In the stored data, the data when there is the light absorption body and the data when there is no light absorption body are given as r(s, i, n) (i=1, 2, 3, . . . , M, n=1, 2, 3, . . . , K), r(0, i, n) (i=1, 2, 3, . . . , M, n=1, 2, 3, . . . , K). Here, i denotes a number assigned to each of the detection modules DM, and n denotes a number assigned to each of groups. Next, respective differences Δr(i, n) are calculated.

In the following, a method of calculating the position of the light absorption body (optical characteristics of the pseudo living body) according to the measurement results obtained by the above-described measurement method based on the flowchart of FIG. 8 will be described. Here, an inverse problem estimation algorithm is used. In order to solve the inverse problem, first, measurement and simulation are performed, and a sensitivity distribution is generated by solving a forward problem. Further, data obtained from the next measurement are read, and using values of the data, the inverse problem estimation is performed (refer to steps S21 through S25 in FIG. 9). FIG. 43 illustrates a block diagram of the calculation unit. Information, which should be used in the Monte Carlo simulation, indicating the positions of the modules (probes), the refractive index and the shape of the living body and the like is recorded in a recording unit (B-1). Based on the information, solving the forward problem is performed. In the calculation, a multi-graphics processing unit (GPU) capable of parallel computing is used. By using the GPU, the computing speed is much higher than the conventional calculation speed. The sensitivity distribution obtained by the calculation is stored in the recording unit (B-1) again. The calculation results and the measurement results stored in the recording unit (A-3) are input to a central processing unit (B-3), and the central processing unit (B-3) performs inverse problem estimation. The estimation result is displayed on the display unit via the central processing unit (A-1) (refer to FIG. 42).

On the other hand, conventionally, when calculating the forward problem, it has been thought that in a scattering body such as a living body, light is scattered substantially in an isotropic manner. As a result, a simulation has been used in which a diffusion equation with small calculation amount is utilized. However, even according to a recent scientific meeting and the like, it is reported that in a microscopic area in the order of millimeters, the light propagation in a living body is anisotropic. In order to perform simulation reflecting the anisotropy, it is necessary to use a transfer equation or perform Monte Carlo simulation.

Because, in the present embodiment, the emitted light from the light source is deflected and incident on the object under test, it is not possible for a generally used diffusion equation to reflect the information of the incidence angle. Therefore, it is proposed to use a transfer equation. But it is known that the transfer equation calculation requires an enormous amount of time.

Therefore, the Monte Carlo simulation is employed in the present embodiment. The Monte Carlo simulation is a method in which photons scattered in a scattering medium are stochastically expressed by using a random variable and the macroscopic behavior thereof is observed. Specifically, the behavior is modeled in such a way that every time the photons move a predetermined distance in a medium, the photons collide with each other and the orientations (directions) thereof are changed. Here, the average value of the predetermined distance is a mean free path defined by the scattering coefficient, and the change of the direction is defined by the anisotropy "g". How the collisions are repeated and how the photons propagate in a defined area are recorded. By calculating a very large number of photons that are modeled as described above, it becomes possible to simulate the light behavior in the scattering medium. By using the Monte Carlo simulation, what kind of path a single photon scatters along is recorded.

In the Monte Carlo simulation according to the present embodiment, it is assumed that the number of the photons is $10^9$ and a voxel is a 1 mm cube, and the calculation for the three-dimensional area of 120 mm×120 mm×60 mm is performed. Here, the scattering coefficient, the absorption coefficient, the anisotropy, and the refractive index of the scattering medium are set to 7.8 mm$^{-1}$, 0.019 mm$^{-1}$, 0.89, and 1.37, respectively, which are substantially the same as those of human scalp. The above-described phantom (i.e., the intralipid water solution) is prepared to have the above values. The simulation is performed under the same conditions of all the light source modules LM, the propagation angle, the positions of the detection modules DM and the like as those in the phantom, and the sensitivity distribution is calculated.

At this time, the number of photons that pass a voxel position "r" is defined as $\varphi_0(r)$. In particular, when the position of the light source module LM is defined as "rs", the number of photons that pass a voxel position "r" is defined as $\varphi_0(rs, r)$. Next, the light source module LM is arranged at the position where the detection module DM was originally arranged and the number of the photons is calculated again. In the case where the detection module DM is arranged at "rd", the number of photons that pass a voxel position "r" is defined as $\varphi_0(r, rd)$.

Because the optical path is invertible, the product thereof is proportional to the number of the photons that had been emitted from the light source module LM, passed the voxel position r, and have entered into the detection module DM. The product thereof which is standardized by all the number of photons $\varphi_0(rs, rd)$ that enter into the detection module DM is the following sensitivity distribution A(r).

$$A(r) = \frac{\phi_0(rs, r)\phi_0(r, rd)}{\phi_0(rs, rd)} \quad \text{[Math. 1]}$$

The sensitivity distribution $A(r)$ indicates an influence degree on a detection amount at the position r. That is, the sensitivity distribution $A(r)$ indicates how much the detection amount is changed by an occurrence of the light absorption body at the voxel position r.

FIG. 10 illustrates an example of the sensitivity distribution calculated as described above. Here, the light source module LM and the detection module DM are arranged at (X, Y, Z)=(45, 60, 0) and (X, Y, Z)=(75, 60, 0), respectively. The voxel is a 1 mm cube. Therefore, the voxel is equivalent to the unit (mm) of the values. The sensitivity of a voxel at a position is expressed in the logarithms with a base of 10 (i.e., common logarithms).

Next, FIG. 11 is a graph of a result of plotting the sensitivity (vertical axis) at the position x (horizontal axis) on the line where Y=60 and Z=10 in the voxel (x, y, z). At this time, the results of the cases where the angles relative to the X axis as the propagation angle on the plane when the Y axis is regarded as the normal line are +60 degrees and −60 degrees are indicated in FIG. 12.

As illustrated in FIG. 11, there is a difference in the sensitivity distributions between the angles of +60 degrees and −60 degrees. This difference can be used as the index of whether it is possible to improve the resolution. In other words, the difference that occurs in the sensitivity distributions indicates that the light propagation paths from two light sources are different. If the light propagation paths from two light sources are the same, substantially the same sensitivity distributions should be obtained even when the propagation angle is changed. Because of the different light propagation paths from the two light sources, it is a fact that the light from the one of the two light sources collects information different from the information collected by the light from the other one of the two light sources.

The above fact creates great value for the inverse problem estimation described below. As described above, light does not scatter in a simple isotropic manner but does indicate slight anisotropy in several mm order. Due to the difference in such a several mm order, it becomes possible to realize the inverse problem estimation having a resolution in a several mm order. The sensitivity distribution is performed under all the propagation angle/detection angle conditions for all the combinations between the light source module LM and the detection module DM provided for the phantom.

Next, by using the sensitivity distribution, the inverse problem estimation is performed.

When it is assumed that the change of the absorption coefficient $\delta\mu_a(r)$ caused by the existence of the light absorption body is sufficiently small, the following formula is obtained based on Retov approximation.

$$\log\frac{\phi_0(rs, rd)}{\phi(rs, rd)} = \frac{v}{S}\frac{\int \overrightarrow{dr}\phi_0(rs, r)\delta\mu_a(r)\phi_0(r, rd)}{\phi_0(rs, rd)} \quad \text{[Math. 2]}$$

Here, the symbol v denotes light speed in the medium, S denotes an amount of light emitted from the light source module LM per unit time, rs denotes the position of the light source module LM, rd denotes the position of the detection module DM, $\varphi(rs, rd)$ denotes an amount of light emitted from the light source module LM and delivered to the detection module DM, and $\varphi_0$ denotes the light intensity in a state where there exists no light absorption body. This formula teaches that when the light intensity $\varphi_0$ in a state where there exists no light absorption body is given, it is possible to relate the change of the absorption coefficient $\delta\mu_a(r)$ caused by the existence of the light absorption body to the observation value log $\varphi(rs, rd)$ by a linear relationship.

When the above teaching is simply described, the following formula can be used.

$$Y=A(r)X$$

Here, Y denotes the change of the observation value due to existence and non-existence of the light absorption body, and X denotes the change of the absorption coefficient at the voxel position r. $A(r)$ denotes the sensitivity distribution. The above formula teaches how the observation value changes when the position and the amount of the light absorption body, which are expressed by X, are changed.

In the inverse problem estimation, the reverse process is performed. In other words, the position X of the light absorption body is estimated by using the observation value Y. As described in the above position measurement method, the measurement is performed by assuming that the change due to existence and non-existence of the light absorption body is expressed as Δr(i, n). This Δr(i, n) corresponds to the observation value Y, and the position X is calculated based on the observation value Y.

Generally, an estimation method for an inverse problem called L2-norm normalization is used. In this method, the X that minimizes the following cost function C is calculated.

$$C=|Y-AX|^2+\lambda|X|^2 \quad \text{[Math.3]}$$

Here, Y denotes the observation value, A denotes the sensitivity distribution, and λ denotes a normalization coefficient. In an inverse problem estimation, these methods are generally used, but in the present embodiment, the inverse problem estimation is performed by using a Bayesian estimation in which detection in the depth direction is possible. Details of the inverse problem estimation using the Bayesian estimation are described in the following non-patent document: T. Shimokawa, T. Kosaka, O. Yamashita, N. Hiroe, T. Amita, Y. Inoue, and M. Sato, "Hierarchical Bayesian estimation improves depth accuracy and spatial resolution of diffuse optical tomography," Opt. Express *20*, 20427-20446 (2012).

As a result, it becomes possible to obtain the estimation result as illustrated in FIG. 13B. FIG. 13A illustrates the position of the light absorption body. The grid in FIG. 13B is 3 mm, and it is understood that the estimation result corresponds to the actual position under the accuracy of 3 mm.

As a comparative example, FIG. 13C illustrates a result when only one direction among the four directions is used for the detection. The configuration in this comparative example is substantially the same as that in a conventional NIRS (DOT) device. In this comparative example, the detection in the depth direction is not possible, and the detection result is extremely expanded.

In the example 1, due to the Bayesian estimation, it becomes possible to detect the position and the depth of the light absorption body.

Further, FIG. 14B illustrates a result of estimation (estimation result) after the position of the light absorption body is changed (refer to FIG. 14A). In this case as well, it is understood that the actual position of the light absorption body can be accurately estimated. By using the method of the example 1, it becomes possible to detect the position of the light absorption body with high resolution. On the other hand, in the comparative example, as illustrated in FIG. 14C, the detection result of the light absorption body is expanded greatly, and it is not possible to accurately detect the position of the light absorption body.

In the following, an example 2 according to the present embodiment will be described. It should be noted that, in the description of the example 1, matters related also to the example 1 are described accordingly.

Example 2

Black ink is dropped in the intralipid water solution (10% concentration intralipid diluted with water 10-fold) which the water tank is filled with in such a way that the black ink is approximately 200 ppm and the absorption coefficient and the scattering coefficient are substantially the same as those of a living body. A light absorption body having black color which simulates blood flow is dipped into the cloudy intralipid water solution. It is assumed that the light absorption body is a black spherical object having a diameter of approximately 5 mm such as black polyacetal. In order to control the position of the spherical object, the spherical object is fixed to a thin metal bar having a diameter of 1 mm connected to an automatic stage. The probes which will be described below are arranged on (attached to) a side of the water tank. The positions of the probes on the side of the water tank are accurately determined. Here, the acrylic water tank has a cuboid figure. The volume (size) of the acrylic water tank is 140 mm×140 mm×60 mm and the thickness of the wall of the acrylic water tank is 1 mm.

The optical sensor 10 includes an emitting system having a plurality of (e.g., eight) light source modules LM and a detecting system having a plurality of (e.g., eight) detection modules DM. The light source modules LM and the detection modules DM are connected to the control unit via electric wiring, respectively.

The control unit controls emitting-light timings of light sources in the light source modules LM and detection timings in the detection modules DM, and transfers obtained detection results to the recording unit. Further, the control unit reads data recorded in the recording unit, performs calculations using the values in the data, and displays the calculation results on the display unit.

As illustrated in FIG. 15, the eight light source modules LM and the eight detection modules DM are arranged in, as an example, a matrix form (two-dimensional lattice form) in which the light source modules LM and the detection modules DM are arranged next to each other at a constant pitch "a" in both X direction and Y direction, which are orthogonal to each other, relative to the pseudo living body (not shown). In FIG. 15, the light source modules LM are indicated by using a square mark and the detection modules DM are indicated by using a circular mark.

As illustrated in FIG. 16, the light source module LM (Type I) includes an optical element such as a lens, a prism, or the like, a ceramic package (not shown) on which a plurality of surface emitting laser array chips are mounted, a flexible printed circuit board (not shown) on which the ceramic package and an analog electronic circuit are mounted, wirings and connector units (not shown) connected to the flexible printed circuit board, a housing containing the above elements, a window member made of a transparent resin which is used to be in contact with an object under test, etc.

The light beams from the surface emitting laser array chips are refracted by the respective lenses and deflected to the desired angle (reflected to the desired direction) by the prisms, as reflection members, which are formed inside of the window member, and the light beams are emitted to the outside of the housing.

As illustrated in FIG. 17, the surface emitting laser array chip has a square shape having a side of approximately 1 mm, and includes a plurality of (e.g., 20) surface emitting lasers which are two-dimensionally arranged.

In more detail, each surface emitting laser array chip has five groups (channel groups), each group having four surface emitting lasers. Here, the centers of four groups among the five groups are arranged at respective corners of a square and the center of the remaining one group is arranged at the center of the square.

The four channels in each group are mounted on the ceramic package as described above and are connected to the same electrode pad (one of electrode pads 1 through 4) via a bonding wiring (a wired line).

The ceramic package is mounted on a wiring pattern of the flexible printed circuit board by soldering. On the flexible printed circuit board, a semiconductor circuit for switching and a semiconductor circuit for stabilizing current are arranged. The semi-conductor circuit for switching controls the surface emitting laser array chip the channels of which emit light. The semiconductor circuit for switching causes the selected channel to emit light according to an external serial signal. One end of the signal line for the serial signal and one end of a power supply line are connected to the flexible printed circuit board, and the other end of the signal line for the serial signal and the other end of the power supply line are connected to the control unit.

The amount of emitted light of each channel is periodically set to be constant by calibration. In a usual use method, the five groups are sequentially caused to emit light using short pulses. In such a pulsed light emission, it is possible to prevent a temperature increase due to the heat generation and accordingly it is adapted to stabilize the amount of emitted light. The detection values, which are obtained by the detection module every time when the light is emitted based on the short pulses, are accumulated and averaged, and thus, the influence of noise can be reduced.

The oscillation wavelength of the surface emitting lasers (VCSEL) of each surface emitting laser array chip is, for example, 780 nm or 900 nm. By using a plurality of surface emitting lasers having oscillation wavelengths different from each other, it becomes possible to obtain a plurality of emitted light beams having different wavelengths. Further, by emitting the light beams having different wavelengths onto substantially the same position of the object under test (e.g., living body), it becomes possible to recognize, for example, a state of a hemoglobin (deoxygenated state or oxygen state). These wavelengths are selected because the absorption coefficients thereof change significantly according to the oxygen concentration in the blood.

In the light source module LM (Type II) according to the example 2 as illustrated in FIG. 18A, a surface emitting laser array chip 1 having an oscillation wavelength of 900 nm and a surface emitting laser array chip 2 having an oscillation wavelength of 780 nm are arranged, a lens 1 (individual optical element) is arranged near the emitting end of the surface emitting laser array chip 1, a lens 2 (individual optical element) is arranged near the emitting end of the surface emitting laser array chip 2, and a prism (common optical element) is arranged on the optical paths of the light beams via the lenses 1 and 2. The surface emitting laser array chips 1 and 2, whose light-emitting directions are Z axis direction, are arranged parallel to each other in Y direction on the X-Y plane. The surface emitting laser array chips 1 and 2 have substantially the same configuration (including the number and the arrangement of light emitting units) except for oscillation wavelengths different from each other. The lenses 1 and 2 are substantially the same lens.

In the following, the surface emitting laser array chips 1 and 2 are also referred to as "ch1" and "ch2", and are also referred to as "ch" in the case where they are not distinguished from each other.

In the light source module LM (Type II), between the two channels, the position relationships between the light emitting units and the optical axis of the corresponding lens are the same. Specifically, the center of each channel (array center) is on the optical axis of the corresponding lens.

Here, attention is paid to three light emitting units of each channel which are lined up at regular intervals in Y direction. Three light emitting units of channel 1 lined up at regular intervals "M" in Y direction are referred to as a light emitting unit "1a", a light emitting unit "1b", and a light emitting unit "1c" in this order from +Y side to −Y side, and three light emitting units of channel 2 lined up at regular intervals M in Y direction are referred to as a light emitting unit "2a", a light emitting unit "2b", and a light emitting unit "2c" in this order from +Y side to −Y side. It is assumed that the light emitting unit 1b and the light emitting unit 2b are arranged on the optical axis of the corresponding lens 1 and 2, respectively.

As illustrated in FIG. 18A, the prism has a symmetrical shape with respect to the central axis (axially symmetric shape), and includes an incidence surface "IS" orthogonal to the central axis, a total reflection surfaces "R1" and "R2" tilted with respect to the central axis, and an emitting (outputting) surface "OS" orthogonal to the central axis.

The incidence surface "IS" is positioned on the optical paths of the light beams from the three light emitting units 1a, 1b, and 1c of the channel 1 and on the optical paths of the light beams from the three light emitting units 2a, 2b, and 2c of the channel 2.

The total reflection surface R1 is positioned on the optical path of the light beam (light beam 1) emitted from the light emitting unit 1a passing through the lens 1 and the incidence surface IS and on the optical path of the light beam (light beam 2) emitted from the light emitting unit 2a passing through the lens 2 and the incidence surface IS. The incidence angles of the light beams 1 and 2 on the total reflection surface R1 are equal to or greater than the critical angle.

The total reflection surface R2 is positioned on the optical path of the light beam (light beam 3) emitted from the light emitting unit 1c passing through the lens 1 and the incidence surface IS and on the optical path of the light beam (light beam 4) emitted from the light emitting unit 2c passing through the lens 2 and the incidence surface IS. The incidence angles of the light beams 3 and 4 on the total reflection surface R2 are equal to or greater than the critical angle.

The emitting surface OS is positioned on the optical paths of the light beams reflected by the total reflection surface R1 (light beams 1 and 2), the light beams reflected by the total reflection surface R2 (light beams 3 and 4), the light beam emitted from the light emitting unit 1b of the channel 1 and passing through (straight) the lens 1 and the incidence surface IS (light beam 5), and the light beam emitted from the light emitting unit 2b of the channel 2 and passing through (straight) the lens 2 and the incidence surface IS (light beam 6), and the light beams 1 through 6 are emitted from (pass through) the OS. Here, the emitting surface OS is a contact surface which is used to be in contact with the surface of the object under test. Therefore, it is preferable that a transparent gel is interposed between the emitting surface OS and the surface of the object under test.

In this case, the light beams having different wavelengths which are emitted substantially in parallel from the two light emitting units 1a and 2a, and incident on the lenses 1 and 2, respectively, are refracted by the lenses 1 and 2, respectively, incident on the incidence surface IS substantially in parallel, refracted by the incidence surface IS, and incident on the total reflection surface R1. The two light beams having different wavelengths reflected by the total reflection surface R1 are incident on substantially the same position of the object under test substantially in parallel. In this case, the incidence positions of the two light beams having different wavelengths on the object under test are slightly (approximately a space between the light emitting unit 1a and the light emitting unit 2a) different.

Similarly, the light beams having different wavelengths which are emitted substantially in parallel from the two light emitting units 1c and 2c, and incident on the lenses 1 and 2, respectively, are refracted by the lenses 1 and 2, respectively, incident on the incidence surface IS substantially in parallel, refracted by the incidence surface IS, and incident on the total reflection surface R2. The two light beams having different wavelengths reflected by the total reflection surface R2 are incident on substantially the same position of the object under test substantially in parallel. In this case, the incidence positions of the two light beams having different wavelengths on the object under test are slightly (approximately a space between the light emitting unit 1c and the light emitting unit 2c) different.

In order to further improve the detection accuracy, it is desirable to make the incidence positions of the two light beams having different wavelengths on the object under test the same (close as much as possible). As a method for the purpose described above, an idea is provided in which the optical paths of the two light beams having different wavelengths reflected by the total reflection surface of the prism are made substantially the same.

Here, an idea may be provided in which two reflection surfaces are arranged respectively on the optical paths of the two light beams having different wavelengths from the two channels (refer to FIG. 16), but it is still difficult to make the optical paths of the two light beams having different wavelengths substantially the same.

In particular, while it is possible to make the emitting directions of the two light beams having different wavelengths from the two channels the same, it is impossible to make the emitting points (positions of the light emitting units) of the two channels the same.

In the following, a light source module LM (Type III) according to the example 2 illustrated in FIG. 19 will be described. The light source module LM (Type III) differs from the light source module LM (Type II) illustrated in FIG. 18 in that the position relationship between the light emitting units and the optical axis of the corresponding lens is different, and other configurations are the same as the light source module LM (Type II).

In the light source module LM (Type III), it is assumed that the center-to-center spacing between the two channels (space between the array centers) is approximately 1.4 mm. This position relationship between the two channels is a result of arranging the two channels as close as possible taking into account the padding portion when wire bonding is performed.

Further, the shape of each channel is a square having a side of 1 mm, and the two channels are very closely mounted, the space between the two channels being several 100 μm. Here, this proximity mounting is realized by good use of a collet of a die bonder device.

Further, the light emitting units (surface emitting lasers) of the two channels are produced by a semiconductor process using the same mask, and the positions of the light emitting units can be controlled with accuracy of 0.5 μm or less.

The light source module LM (Type III) has the same layout of the surface emitting laser array chip 1 (900 nm) and the surface emitting laser array chip 2 (780 nm) as the light source module LM (Type II) with the same level of accuracy.

The two light beams having different wavelengths emitted from the two channels whose centers are separated approximately 1.4 mm, passing through the corresponding lenses, are reflected by the same total reflection surface of the prism and incident on the object under test (e.g., living body).

At this time, with the configuration of the light source module LM (Type II), because the corresponding light beams from channel 1 and channel 2 are incident on the object under test (e.g., living body) while keeping the substantially constant spacing (approximately 1.4 mm) and keeping the state parallel to each other, the incidence positions thereof are also separated by approximately 1.4 mm. When the spacing between the incidence positions is large as described above, the resolution in fNIRS which detects brain blood flow by using the inverse problem estimation is lowered.

Here, by investigating a method for making the optical paths of the two light beams having different wavelengths substantially the same and making the incidence positions the same without increasing mounting cost, the present inventors have developed an idea of dislocating the centers of the channels (array centers) with respect to the optical axis of the corresponding lens by several μm to several 100 μm (preferably several 10 μm) and have applied the idea to the light source module LM (Type III).

In the following, the details of implementing the idea will be described referring to FIG. 20. Here, the centers of the channels are dislocated from the optical axis of the corresponding lens by approximately 20 μm. The dislocating amount is not limited to 20 μm, but may be changed appropriately.

Here, without changing the center-to-center spacing between the two channels, the lenses are dislocated with respect to the corresponding channels. The dislocating directions of the lenses with respect to the corresponding channels can be axially symmetrical (rotationally symmetrical) with respect to the center axis of the prism as a common optical element (refer to FIG. 21).

In other words, as long as the two channels 1 and 2 and the two lenses 1 and 2 are arranged axially symmetrical with respect to the center axis of the prism (common optical element), the arrangement is not limited to the one illustrated in FIG. 21.

Here, as an example, two channels are arranged in such a way that the centers thereof are axially symmetrical (point symmetrical) with respect to the center axis of the prism while the center axis is sandwiched in Y direction by the two channels. Each channel includes five light emitting units (VCSEL), and the five light emitting units are arranged at a center (array center) of a square, one of whose diagonals is parallel to Y direction, and at four vertexes of the square, respectively.

As an example, the center-to-center spacing between the two channels is 1.4 mm, effective diameters of the lenses are 0.8 mm, and focal lengths of the lenses f=600 μm. Here, the direction in which the lenses 1 and 2 are dislocated with respect to the two channels 1 and 2 is a direction such that the lenses 1 and 2 are closer to each other as illustrated in FIG. 21. Here, the lens 1 is dislocated from a position where the optical axis of the lens 1 is located at the center of the channel 1 by approximately 20 μm in −Y direction, and the lens 2 is dislocated from a position where the optical axis of the lens 2 is located at the center of the channel 2 by approximately 20 μm in +Y direction. As a result, the center of the channel 1 is dislocated from the optical axis of the lens 1 by approximately 20 μm, and the center of the channel 2 is dislocated from the optical axis of the lens 2 by approximately 20 μm.

In this case, the optical path from the lens 1 to the total reflection surface R1 of the light beam (light beam 1') which is emitted from the light emitting unit 1a of the channel 1 and incident on the total reflection surface R1 via the lens 1 and the incidence surface IS, is not parallel to the optical path from the lens 2 to the total reflection surface R1 of the light beam (light beam 2') which is emitted from the light emitting unit 2a of the channel 2 and incident on the total reflection surface R1 via the lens 2 and the incidence surface IS. Therefore the two optical paths get closer to each other as they get closer to the total reflection surface R1 (refer to FIG. 19). It should be noted that, in the case where incidence angles of light with respect to a lens are the same, the more the incidence position is separated from the optical axis of the lens, the larger becomes the refractive angle of light.

Also, the optical path from the lens 1 to the total reflection surface R2 of the light beam (light beam 3') which is emitted from the light emitting unit 1c of the channel 1 and incident on the total reflection surface R2 via the lens 1 and the incidence surface IS, is not parallel to the optical path from the lens 2 to the total reflection surface R2 of the light beam (light beam 4') which is emitted from the light emitting unit 2c of the channel 2 and incident on the total reflection surface R2 via the lens 2 and the incidence surface IS. Therefore the two optical paths get closer to each other as they get closer to the total reflection surface R2 (refer to FIG. 19).

Also, the optical path from the lens 1 to the emitting surface OS of the light beam (light beam 5') which is emitted from the light emitting unit 1b of the channel 1 and incident on the emitting surface OS via the lens 1 and the incidence surface IS and the optical path from the lens 2 to the emitting surface OS of the light beam (light beam 6') which is emitted from the light emitting unit 2b of the channel 2 and incident on the emitting surface OS via the lens 2 and the incidence surface IS get closer to each other as the two light beams get closer to the emitting surface OS (refer to FIG. 19).

Further, the optical paths of the two light beams (light beams 1' and 2') having different wavelengths and being not parallel to each other which are reflected by the total reflection surface R1 intersect near the emitting surface OS which is in contact with the object under test. Further, the optical paths of the two light beams (light beams 3' and 4') having different wavelengths and being not parallel to each other which are reflected by the total reflection surface R2 intersect near the emitting surface OS which is in contact with the object under test (refer to FIG. 19).

As a result, as illustrated in FIG. 19, the optical paths of the two light beams (light beams 1' and 2') having different wavelengths which are reflected by the total reflection surface R1 become substantially the same and the incidence positions of the two light beams on the object under test become the same. Further, the optical paths of the two light beams (light beams 3' and 4') having different wavelengths which are reflected by the total reflection surface R2 become substantially the same and the incidence positions of the two light beams on the object under test become the same. Further, the incidence positions, on the object under test, of the two light beams (light beams 5' and 6') having different wavelengths which are directed from the incidence surface IS to the emitting surface OS without being involved with the total reflection surfaces become substantially the same.

Further, light flux including the light beams 1' and 2', light flux including the light beams 3' and 4', and light flux including the light beams 5' and 6' are not parallel to each other and are incident on the object under test at substantially the same position.

It should be noted that the light beams from light emitting units other than the light emitting units 1a, 1b, and 1c of the channel 1 as illustrated in FIG. 21 and the light beams from light emitting units other than the light emitting units 2a, 2b, and 2c of the channel 2 pass through the incidence surface IS, and are emitted from the emitting surface OS and incident on substantially the same position of the object under test as the above light flux.

In the above-described light source module LM (Type III), by using a simple method in which the lenses are shifted (dislocated) with respect to the channels, it is possible to make the optical paths of the light beams having different wavelengths substantially the same and make the incidence positions of the two light beams the same. By making the incidence positions of the two light beams having different wavelengths the same, it becomes possible for a NIRS device which performs an inverse problem estimation to measure brain blood flow positions with higher accuracy.

On the other hand, in order to obtain the similar effect as the light source module LM (Type III), if members such as half mirrors are used instead of the lens shift, the mounting cost would increase due to the increased optical parts requiring additional position determination with high accuracy.

It should be noted that, in the light source module LM (Type III), the optical axes of the lenses 1 and 2 are dislocated (shifted) from a position in line with the center of the corresponding channels 1 and 2, but the arrangement is not limited to this.

For example, the optical axis of one of the lenses 1 and 2 may be dislocated from the position in line with the center of the corresponding channel and the optical axis of the other of the lenses 1 and 2 may be positioned in line with the center of the corresponding channel.

Also, in place of or in addition to shifting the lenses with respect to the corresponding channels, the channels may be shifted with respect to the corresponding lenses.

Also, the directions in which the lenses are shifted with respect to the corresponding channels 1 and 2 may be changed appropriately. For example, the lenses 1 and 2 may be shifted in the same direction or in the opposite direction (a direction in which the lenses get closer to each other or a direction the lenses get separated from each other).

Also, the shift amounts (dislocation amounts) of the lenses 1 and 2 with respect to the corresponding channels 1 and 2 may be the same or may be different.

To summarize the above, the bottom line is, it is only necessary that, in order to make the optical paths of the light beams having different wavelengths the same, the position relationships between the light emitting units and the optical axis of the corresponding lens are made different between the channels.

In detail, it is desirable that the position relationships between the light emitting units and the optical axis of the corresponding lens are made different between the channels in such a way that the optical paths of the light beams having different wavelengths emitted from the channels 1 and 2 via the lenses 1 and 2 get closer to each other and the optical paths of the two light beams intersect near the contact surface of the light source module LM (Type III) which surface is in contact with the object under test (i.e., near the emitting end of the light source module LM (Type III)).

In the following, the reason why the surface emitting laser array chip is employed as the light source of the optical sensor 10 will be described. In the surface emitting laser array chip, a plurality of channels can be arranged at positions close to each other in a two-dimensional form and each channel can be controlled independently. Further, by arranging tiny lenses near the channels, traveling directions of the emitted light beams can be changed.

Further, in the optical sensor used for DOT, it is required to control incidence angles on the object under test as accurately as possible. An LED (light-emitting diode) has a wide emitting angle. As a result, in order to provide parallel light with high accuracy, it is necessary for a lens to have an aspheric surface. Further, because the emission angle of an LD (laser diode, edge emitting laser) is asymmetric, in order to provide parallel light with high accuracy using a lens, it is necessary to combine a lens having the curvature in the vertical direction different from the curvature in the horizontal direction, and a cylindrical lens. As a result, the configuration becomes complicated and a highly-accurate mounting technique is required.

On the other hand, the surface emitting laser has a substantially exact circular shaped far field pattern, and parallel light can be obtained by arranging one spherical lens. Further, in the case where coherent light emitted from the LD is used, a speckle pattern, in which scattered light beams interfere with each other, occurs in an object under test (scattering body). The speckle pattern negatively affects the measurement as noise.

In the case where blood flow in a brain is observed as in the DOT, the scattering number is extremely large. As a result, the negative influence is limited. However, there is an influence of returned light in which the light reflected by a skin surface directly returns to the light source. The returned light makes the oscillation state in the LD unstable and a stable operation cannot be performed. In the case of an optical disk, in order to stably use the coherent light, a wave plate is used to prevent the regular reflection light from becoming the returned light. However, it is difficult to remove the returned light related to the scattering body.

In the case of the surface emitting laser array chip, it is possible to simultaneously emit a plurality of light beams onto a fine area, and it is also possible to reduce the interference caused by the returned light (refer to, for example, Japanese Laid-open Patent Publication No. 2012-127937).

In the present embodiment (examples 1 and 2), a convex lens (hereinafter, simply referred to as "lens") is arranged on an optical path of the light from the surface emitting laser array chip (refer to FIG. 22).

The diameter of the convex lens is 1 mm, and the effective diameter "ε" of the convex lens is 600 μm. The focal length "f" of the convex lens is 600 μm. The surface emitting laser array chip is 1 mm×1 mm, and a distance "dmax" between the centers of the two channels which are separated most in the surface emitting laser array chip is 600 μm. By setting the effective diameter c and the distance dmax to be equal to each other, it becomes possible to minimize the diameter of the convex lens.

Here, the positions of the convex lens and the surface emitting laser array chip are determined in such a way that the distance "L" between the main point (optical center) of the convex lens and the light emitting surface (emitting surface) of the surface emitting laser array chip in the optical axis direction of the convex lens is, for example, 300 μm. In other words, f≠L.

In this case, the light emitted from the surface emitting laser array chip and having passed through the convex lens is regularly reflected by the prism or the like, and it becomes possible to avoid the occurrence of a phenomenon that the light is collected on the surface emitting laser array chip by the convex lens (returned light phenomenon). As described above, because the returned light phenomenon does not occur, it becomes possible to stabilize the amount of light emitted by each of the channels in the surface emitting laser array chip.

However, in the case where the influence of the returned light is not considered (higher resolution is not necessary in the NIRS), it may be set f=L.

Further, as illustrated in FIG. 23, a transparent resin fills in between the convex lens and the surface emitting laser array chip, and thus, no air layer is formed therebetween. As the transparent resin, a resin having the refractive index similar to that of the convex lens (e.g., thermosetting epoxy-based resin) is used. In other words, the refractive index does not change at the boundary surfaces between the convex lens and the surface emitting laser array chip. The transparent resin may be formed by metallic molding before fixing the convex lens or may be injected after fixing the convex lens.

As described above, by supplying the transparent resin to fill in between the convex lens and the surface emitting laser array chip, it becomes possible to prevent the light, which is emitted from the surface emitting laser array chip, from being reflected by the surface of the convex lens on the side of the surface emitting laser array chip. In other words, it becomes possible to prevent the occurrence of the returned light. Because the returned light phenomenon does not occur, it becomes possible to stabilize the amount of light emitted by each of the channels in the surface emitting laser array chip. When the amount of light from each of the channels is stabilized, it becomes possible to increase the signal/noise (S/N) ratio of the measurement system, and thus, the highly accurate NIRS measurement and the higher resolution can be realized.

As illustrated in FIG. 24, the convex lens is fixed to a package, on which the surface emitting laser array chip is mounted, via a sub mount. An electrode on the surface emitting laser array chip (chip electrode) is electrically connected to a PKG electrode on the package via a wire. The height of the wire is several tens μm, therefore, the wire is designed so as not to be interfered with by the sub mount. The fixed position "L" of the convex lens (the distance between the light emitting surface of the surface emitting laser array chip and the main point of the convex lens) is limited by the height of the wire. In other words, in the case where the wire is used, it is necessary to avoid the sub mount and set the height of the wire equal to or less than 100 μm. That is, it is preferable that the relationship −100 μm<f−L<0 is satisfied. It should be noted that the transparent resin in FIG. 23 is omitted in FIG. 24.

The light emitted from the emitting surface of the surface emitting laser has a substantially circular shape, and the divergence angle is 5 degrees by the half value width. Generally, because the beam of an LD has an elliptical shape, it is necessary to consider a setting error in the rotational direction; but it is not necessary to consider the setting error in the surface emitting laser, which is an advantage of the surface emitting laser. Further, due to the circular shape, when an inverse problem is resolved using optical simulation, it becomes easier to use an approximation based on the symmetric property, which is another advantage.

The beam emitted from the surface emitting laser is refracted by the convex lens arranged near the surface emitting laser. The refraction angle is determined based on the relative position between the surface emitting laser and the lens center (optical axis of the lens). Therefore, by setting the positions of the channel groups of the surface emitting laser array chip and the position of the lens appropriately, it becomes possible to obtain a desired refraction angle.

In example 2, the relative position between the channels and the optical axis of the convex lens is determined in such a way that the refraction angle becomes approximately 20 degrees. In the surface emitting laser array chip, it is possible to independently control the emissions of the channels. Therefore, by selecting the channel for the emission, it becomes possible to change the direction of light emitted from the light source module LM.

FIG. 25 illustrates an example of a light beam drawing optically designed by an optical simulator. Here, three channels (light sources), which simulate the surface emitting laser array chip, and a lens near the channels, whose diameter is 1 mm and whose f=600 μm, are arranged. One of the three channels is arranged on the optical axis of the lens, one of the other two channels is arranged on one side of the optical axis of the lens, and the other of the other two channels is arranged on the other side of the optical axis of the lens. The light from the channels other than the channel on the optical axis is refracted and the propagation direction (path) is bent. In other words, the two light beams, which are emitted from the channels other than the channel on the optical axis, are emitted in the directions opposite to each other and at the angle of approximately 20 degrees relative to the optical axis of the lens.

Here, the light source module LM is designed in such a way that the incidence angle of the light on the object under test is approximately 55 degrees. Specifically, as illustrated in FIG. 16, the light source module LM is designed in such a way that, by causing the light beams which are emitted from the convex lens in the directions inclined by approximately 20 degrees relative to the optical axis of the convex lens to be individually reflected, the angle of the light beams relative to the optical axis of the lens is converted from approximately 20 degrees to approximately 55 degrees and the deflected light beams inclined by approximately 55 degrees can be incident on the surface of the object under test.

It should be noted that the prism may be anything as long as it can reflect light, and a glass substrate on which a metal membrane is formed may be used as the prism. Further, for example, a prism using a total reflection phenomenon caused by a difference between refractive indexes may be employed. As an example of the prism, FIG. 26 illustrates a result of optical simulation. The light beams emitted from the VCSEL are refracted by the convex lens and incident on the prism.

Here, it is assumed that the material of the prism is BK7, but a general-purpose optical material may be used. The light beams incident on the prism are totally reflected by the prism side surface (reflection surface) and the reflected light beams are incident on the object under test with the incidence angle of approximately 55 degrees. In other words, the light beams having passed through the convex lens are deflected by the prism in such a way that the incidence angle of the light beams on the object under test becomes approximately 55 degrees. In this case, in order to prevent the light from being scattered in the boundary surface between the prism and the object under test, a transparent gel is interposed between the prism and the object under test. Here, the light beams from the surface emitting laser array chip are also refracted into non-parallel light beams by the convex lens, and the non-parallel light beams are reflected by the prism to be incident on the object under test. As a result, non-parallel but substantially parallel light beams are incident on the same position of the object under test (refer to FIG. 26).

By Snell's law based on a difference in refractive index between the prism and the object under test, the propagation angle of the light beams in the object under test is changed from approximately 55 degrees to approximately 60 degrees.

In the optical system including the convex lens and the prism, by using a fact that the positions of the channels in the surface emitting laser array chip are different from each other, it becomes possible to set the propagation angle of the light beams in the object under test. Here, by dislocating the centers of the channels (VCSEL) from the optical axis of the convex lens by approximately 200 μm, it becomes possible to set the propagation angle of the light beams emitted from the channels to be approximately 60 degrees in the object under test. In this case, the light beams emitted from the different channels are emitted from the different positions of the emission surface of the convex lens as non-parallel but substantially parallel light beams.

As a comparative example, FIG. 27 illustrates an optical simulation result when the focal length f=600 μm and the fixed position L=1.6 mm. When the difference between f and L is equal to or greater than 1 mm, the light beams widely expand as illustrated in FIG. 27. When the light beams expand like this, it is necessary to enlarge the incidence surface of the object under test. However, as the practical size of the incidence surface in actual NIRS, the diameter φ of approximately 2 mm is the limit. This limitation relates to a fact that the distance between adjacent human hair roots is approximately 2 mm, and if the size of the incidence surface is equal to or greater than 2 mm, then a high resolution NIRS cannot be realized because the hairs serve as optical obstacles. In other words, it is desired that the difference between f and L is less than 1 mm.

The lenses 1 and 2 in FIG. 16 are directly fixed to the ceramic package on which the surface emitting laser array chip is mounted in such a way that the lenses 1 and 2 are accurately and stably arranged at the designed positions.

In FIG. 25, a case is described where the convex surface of the lens faces the surface emitting laser side, but the convex surface of the lens may face the side opposite to the surface emitting laser side. As illustrated in FIG. 25, by arranging the convex lens in such a way that the convex surface of the convex lens faces the surface emitting laser side and the plane surface of the convex lens faces the object under test side, the distance between the surface emitting laser array chip and the convex lens can be longer. In a process of mounting the chip, in order to avoid interference among parts and an arm for picking up the parts, it is preferable that the distance is longer to some extent.

Regarding the lens, any optical part may be used as long as it refracts light, and, a gradient index (GRIN) lens using the refraction index distribution of an optical fiber, etc., may be used. By using the GRIN lens, compared to using a spherical lens, it becomes possible to select a lens having a generally smaller spherical aberration and a smaller f value with lower cost.

In example 2, in order to allow the light to be incident on an end part of the lens rather than the center part of the lens alone, it is preferable that the spherical aberration is smaller.

It can be understood from the above description that a plurality of light fluxes that are not parallel to each other are emitted from the light source modules LM (Type I, Type II, and Type III) according to the example 2 (refer to FIG. 16, FIG. 18, and FIG. 19). Further, from the light source modules LM (Type I and Type II), two light beams having different wavelengths are emitted in a state where the optical paths of the light beams are substantially parallel and close to each other (refer to FIG. 16 and FIG. 18). Further, from the light source module LM (Type II), two light beams having different wavelengths are emitted in a state where the optical paths of the light beams are not parallel to each other but substantially the same (refer to FIG. 19).

Further, the light fluxes from the light source modules LM (Type I, Type II, and Type III) whose optical paths are not parallel to each other are incident on substantially the same position of the object under test (refer to FIG. 16, FIG. 18, and FIG. 19). Further, the light beams from the light source module LM (Type III), which have different wavelengths and whose optical paths are substantially the same, are incident on the same position of the object under test (refer to FIG. 19).

The above "substantially the same position" means that, for example, in the case where the light source modules LM are arranged at approximately 60 mm intervals, the positions are substantially the same with respect to the 60 mm, and a plurality of positions which are separated from each other by approximately several mm may be referred to as "approximately the same position".

Further, although the above "the same position" means that the degree of the sameness is higher than the "substantially the same position", "the same position" may include not only the case where the positions are strictly the same but also the case where the positions are separated from each other by 1 mm or less.

Further, the above "optical paths are substantially the same" means that the angle between the optical paths of the two non-parallel light beams is equal to or less than 10 degrees. It should be noted that, when the two optical paths are substantially the same, it is preferable that the angle between the optical paths of the two non-parallel light beams is equal to or less than 1 degree.

An algorithm for resolving the inverse problem will be described bellow. When resolving the inverse problem, an optical simulation setting the position of the light source module LM is performed. When the optical simulation is performed, by accurately setting the dislocation of the incidence position on the object under test, no error occurs in the inverse problem estimation.

However, as described in, for example, Patent Document 1, in order to arrange the probes in a high-density manner while the positions of the probes are separated from each other by 10 mm or more, it is necessary to independently arrange the light source modules. The operation of arranging the light source modules is complicated and requires the operation of putting hair aside one by one, and the more the number of the light source modules increases, the more the number of operations increase.

In the present embodiment, as described below, by arranging only one light source module LM, it is possible to obtain an information amount the same as that obtained when a plurality of light modules are arranged and it is possible to detect with higher resolution than is realized in the high-density probe as described in Patent Document 1 without increasing the complicated operations.

Further, in a light source module according to a comparative example in which a plurality of light beams which are parallel to each other are incident on a living body as illustrated in FIG. 28A, in the case where there is an altered part near the surface of the living body, a detection error may occur. The "altered part" refers to a part whose optical characteristics are particular, and the altered part includes, for example, hair and artificially-colored skin. When there is such an altered part, in the comparative example, the light from the light source 1 is incident on a position different from the position where the light from the light source 2 is incident, and as a result, there may be a case where, for example, only the light from the light source 2 passes through the altered part. When the difference between the light source 1 and the light source 2 is calculated, the altered part becomes noise.

On the other hand, in the present embodiment, as illustrated in FIG. 28B, the light from the light source 1 and the light from the light source 2 pass through "substantially the same position" on the surface of the skin, and when the light from one of the light source 1 and the light source 2 passes through an altered part, the light from the other of the light source 1 and the light source 2 also passes through the altered part. Further, when the light from one of the light source 1 and the light source 2 does not pass through an altered part, the light from the other of the light source 1 and the light source 2 does not pass through the altered part, either. More specifically, both the light from the light source 1 and the light from the light source 2 take the same optical path near the skin surface, and take the different optical paths in the depth direction. In other words, it is not very sensitive to detect a difference near a skin surface, but it is sensitive to detect a difference near brain tissue. By reducing the noise near the skin surface, the resolution is improved. As described above, the meaning of the term "substantially the same position" permits the dislocation of several mm.

Further, in example 2, a transparent gel is dropped on the window member formed in the housing, and the transparent gel is interposed between the window member and the surface of the object under test to prevent air being introduced therebetween.

In a conventional light source module, the light, which is first emitted into the air, is incident on and propagates in a body via the skin surface. At this time, a difference in refractive index exists between the air having the refractive index of 1.0 and the living body having the refractive index of 1.37. Due to the difference in the refractive indexes, reflection and scattering occur. Further, because the refractive index of the living body where light propagates is less than that of air outside the living body, the propagation angle (also referred to as in-body propagation angle) relative to the incidence angle becomes smaller. The light refraction at a boundary surface can be understood when Snell's formula is used. Snell's formula can be expressed by using the refractive indexes only.

FIG. 29 is a graph illustrating the relationship (refraction of light) between the incidence angle and the in-body propagation angle at the boundary surface between the air (incidence side: the refractive index is 1.0) and the living body (propagation side: the refractive index is 1.37). As understood from FIG. 29, even when the incidence angle of the light incident on the living body is 60 degrees, the propagation angle of the light in the living body becomes 40 degrees which is smaller than the incidence angle. Therefore, it is understood that, even if it is necessary to achieve the propagation angle of the light in the living body equal to or greater than 60 degrees, it is not possible to achieve such propagation angle when the light is incident from air. In other words, it is difficult to achieve a large propagation angle of light in the living body if the light is first emitted in air.

To resolve the problem, in example 2, the refractive index of the transparent resin which is the material of the window member of the light source module LM is set to be greater (e.g., 1.5 or greater) than the refractive index (1.37) of the living body (refer to FIG. 30). In this case, the propagation angle in the living body of the light, which is directly incident on the living body from the light source module LM at the incidence angle of 60 degrees, exceeds 70 degrees. In designing the light source module LM, when the angle is reduced, it becomes possible to obtain advantages such as reducing the size of the light source module LM.

In the light source module LM (Type I) in example 2, as illustrated in FIG. 16, the light, which is emitted from the surface emitting laser in the direction parallel to the optical axis of the lens, is refracted by the lens and travels in the direction inclined by approximately 20 degrees relative to the optical axis of the lens to be incident on the window member. Here, the refractive index of the window member is set to be approximately 1.5. The light having passed through the lens is refracted when the light is incident on the window member, but because the incident angle is deep, the refraction is not great. The light, which is incident on the window member, is deflected by the reflection surface of the prism and travels inclined by approximately 55 degrees relative to the optical axis of the lens. This angle of 55 degrees is the angle in the window member having the refractive index of 1.5, and, as illustrated in FIG. 30, the propagation angle in the living body (refractive index: 1.37) becomes approximately 60 degrees.

In order for the light from the light source module LM to be directly incident to propagate in a pseudo living body, it is necessary to remove an air layer in the boundary surface between the pseudo living body and the light source module LM. Here, a transparent gel is used for removing the air layer. The transparent gel used here is a glycerin solution that is compatible with the pseudo living body. Further, the volatile characteristics of the transparent gel are adjusted in such a way that the transparent gel does not evaporate during testing (i.e., while the light source module LM is capped) and the transparent gel does evaporate at an appropriate timing after testing or being absorbed into the pseudo living body. The optical characteristics of the transparent gel are adjusted in such a way that the transparent gel is transparent when the wavelength is approximately 780 nm and the refractive index of the transparent gel is similar to that of a pseudo living body surface. Here, the refractive index of the transparent gel is prepared to have the value of approximately 1.37. By the above preparation, even when the pseudo living body surface is uneven, a difference in the refractive index due to the uneven surface is not generated and it becomes possible to produce a state where no reflection occurs. Accordingly, it becomes possible to remove most reflections at the pseudo living body surface. Further, even when the boundary surface with the pseudo living body is physically uneven, it is not optically uneven, and no scattering occurs. As a result, it becomes possible for the light to accurately propagate in the pseudo living body in an appropriate propagation direction in accordance with the emission angle of the light from the light source module LM. Generally, scattering is strongly produced during the propagation in the pseudo living body, but scattering at the skin surface is also not weak. As a result, it becomes possible to secure high anisotropy of the light. Because high anisotropy can be obtained, it becomes possible to greatly change the incidence angle of the light beams from the light source module LM onto the pseudo living body, and, as described below, it becomes possible to greatly change the incidence angle of the light beams received by the detection module DM.

As illustrated in FIG. 31, the detection module DM includes a housing, an optical element, a flexible printed circuit board (not shown) including light receiving units and an analog electronic circuit, wirings and connector units (not shown) connected to the flexible printed circuit board, etc.

As illustrated in FIG. 32, in the light detection module DM, the light, which is emitted from the light source onto the object under test and propagates in the object under test, is divided into a plurality of light beams to be guided into a plurality of light receiving units.

In a related art technology (refer to Japanese Laid-open Patent Publication No. 2011-179903), in a DOT using fluorescent light, the light receiving units are arranged corresponding to the light beams emitted from the object under test at a plurality of angles. However, when the light receiving units are arranged in this way, the light incident on the light receiving units corresponds to all the emission angles from the object under test.

On the other hand, the detection module DM in the present embodiment divides the light from "substantially the same position" of the object under test and separately detects the divided light. Here, as described above in the light source module LM, because it is possible to design the accuracy of "substantially the same position" in the optical simulation, it does not matter when the position differs in several mm order.

In the following, details of the detection module DM will be described. As illustrated in FIG. 33, the detection module DM includes a housing made of a black resin, a contact member attached to the top end of the housing and made of an elastic member, and a transparent division lens and four light receiving units contained in the housing. Apertures (openings) are formed at the end of the housing and in the contact member.

As the contact member, a member made of black rubber is used to enhance the light-blocking effect. From the aperture of the contact member, the center part (having a diameter of approximately 1 mm) of the division lens protrudes by several hundreds μm outside beyond the housing. Because this protruded part is in contact with the living body surface, there is optically no air, and thus, Fresnel refraction, scattering and the like are reduced.

Further, in the detection module DM as well, the above-described transparent gel is used and the stability can be further improved. The division lens is made of a transparent resin and has a refractive index of approximately 1.8. The division lens is fixed to the housing.

The aperture is a circular hole having a diameter of approximately 1 mm and penetrating through the top end of the housing and the contact member, and the aperture has a function to limit positions where the light, which has propagated in the object under test, is output from the object under test. The light output from the aperture is directed in different directions. It is possible to limit the incidence position of the light by the aperture. Then, the incidence light is divided into a plurality of light beams with the division lens and the light beams can be individually detected.

The above-described feature that the light from the object under test is incident onto the light receiving unit from "substantially the same position" of the object under test is realized by the aperture.

Because the light having passed through the aperture is refracted by the division lens to different directions corresponding to the propagation directions of the light, the incidence positions on the light receiving units are different.

The division lens is a spherical lens having a diameter of approximately 3 mm and a focal length f of approximately 3 mm.

In example 2, the number of the light beams produced by the division lens is four, and a photodiode array (PD array) having four light receiving units (photodiodes: PDs) arranged in two dimensional manner is used. In FIG. 33, only two light receiving units 1 and 2 of the four light receiving units (PDs) are illustrated.

Here, the PD array has a square shape whose side length is approximately 3 mm, and each PD has a square shape whose side length is 1.4 mm. The angle θ2 is defined as illustrated in FIG. 33, and the distance between the PD array and the aperture is approximately 5 mm.

One surface of the lens is plane surface, and the other surface is a spherical surface. The plane surface side of the lens is in contact with the pseudo living body. Because the position of the aperture is dislocated from the focus position of the lens, the aperture does not create parallel light. However, the aperture has a function to limit the light to be incident on the PD array.

According to an optical simulation performed on this optical system, it is found that the light having the angle θ2 in a range of approximately −10 degrees to 50 degrees is incident on the light receiving unit 2 and the light having the angle θ2 in a range of approximately −50 degrees to 10 degrees is incident on the light receiving unit 1. In other words, the light, which has propagated in the pseudo living body and has been emitted from the aperture, is divided into a plurality of light beams depending on the emission angles and each of the light beams is incident on one of the four light receiving units.

In example 2, a spherical lens is used as the division lens, but an aspherical lens may be used and larger angles may be detected. The division accuracy and the number of light beams have a correlation with the estimation accuracy of the inverse problem described below and a necessary optical system is determined based on the desired estimation accuracy. In the present embodiment, the spherical lens and 4 light beams are employed.

Each of the PDs is electrically wired to be connected to an operational amplifier. As the operational amplifier, a semiconductor operational amplifier is used to supply power at 5 V. Because the amount of the detected light is very small, the gain of the operational amplifier is high and a two-stage amplifier configuration is used. In the first stage, magnifications of approximately hundreds of thousands times are performed, and in the second stage, magnifications of approximately thousands times are performed.

In example 2, a position measurement method of measuring the position of the light absorption body in the pseudo living body (an optical characteristics detection method for the object under test) will be described referring to a flowchart in FIG. 34.

First, the probes (the light source modules LM and the detection modules DM) are set on (attached to) the pseudo living body (step S1). At this time, a transparent gel is placed between the acrylic water tank and the probes and the probes are carefully set at the positions determined by the fixing members one by one in such a way that no air bubbles are generated in the transparent gel.

The probes are eight light source modules LM and eight detection modules DM (total 16 probes) and the light source modules LM and the detection modules DM are arranged alternately next to each other at a constant pitch in a lattice pattern (refer to FIG. 15). The lattice pitch (between lattice points) is 30 mm, and the distance between the light source module LM and the detection module DM is 30 mm.

In this state, light is emitted from channels of an arbitrarily selected light source module LM (step S2). The emission is performed on a group (4 channels) basis, and the current value is determined in such a way that the emission intensity is approximately 4 mW. The light emitting duration is approximately 10 ms, during which detection values are read by all PDs, and several points of the data (detection values) detected every 1 ms interval are averaged (step S3). Then, the averaged values are stored in the recording unit (step S4). Similarly, in the next group, the emission for 10 ms, the measurement, and the data storage are repeated (steps S5, S6, and S2 through S4). It should be noted that the emission of the four channels of the surface emitting laser array chip having an oscillation wavelength of 780 nm and the emission of the four channels of the surface emitting laser array chip having an oscillation wavelength of 900 nm are sequentially and similarly performed.

However, it can be said that, in the following data process, the two wavelengths are substantially similarly treated and the measurement at the same position is performed two times in the same manner. Originally, in order to detect the change of blood flow, by using a difference obtained by using those two wavelengths, it is possible to individually detect oxygenated hemoglobin and reduced hemoglobin. However, in the present embodiment, by using two surface emitting laser array chips having different oscillation wavelengths for measuring respective data, it is possible to reduce the noise caused by the differences between the chips.

After the emissions and the measurement of all the groups of the light source module LM are completed, the emission of the next light source module LM is performed (steps S7, S8, and S2 through S6). Similar to the above, the emissions are sequentially performed on a group (4 channels) basis. After emissions and the measurement of all the light source modules LM are completed, the light absorption body is set (steps S9 and S10). The light absorption body is set by using an optical stage so that the setting of the light absorption body can be accurately performed in a position-reproducible manner. In the state where the light absorption body is set, the emissions of the channels through the recording of the PD values are repeated (steps S2 through S9).

In the stored data, the data when there is the light absorption body and the data when there is no light absorption body are given as $r(s, i, n)$ ($i=1, 2, 3, \ldots, M$, $n=1, 2, 3, \ldots, K$), $r(0, i, n)$ ($i=1, 2, 3, \ldots, M$, $n=1, 2, 3, \ldots, K$). Here, "i" denotes a number assigned to each of the detection modules DM, and "n" denotes a number assigned to each of groups. Next, respective differences $\Delta r(i, n)$ are calculated.

Because the method of calculating the position of the light absorption body (optical characteristics of the pseudo living body) based on the measurement results obtained by the above position measurement method is similar to the method of calculating the position of the light absorption body (optical characteristics of the pseudo living body) based on the measurement results obtained by the measurement method based on the flowchart of FIG. 8, the repeated description thereof is herein omitted.

As a result, it becomes possible to obtain the estimation result as illustrated in FIG. 35. FIG. 35 further illustrates a result of a comparative example where light is emitted from only one group at the center of the surface emitting laser array chip (refer to FIG. 17) and the detection is performed using the detection values of only one PD among the four PDs in the PD array. Other than this limitation, the numerical processing similar to that in the present embodiment is performed. The configuration in this comparative example is substantially the same as that in a conventional NIRS (DOT) device.

In the present embodiment, due to the Bayesian estimation, it is possible to detect the position and the depth of the light absorption body. In the result illustrated in FIG. 35, a mark "○" (circle) is marked when the position of the light absorption body can be detected. In the present embodiment, when the distance in the depth direction (here, Z axis direction in FIG. 10) becomes greater, the distance from the light source module LM is increased and an amount of light that can propagate is reduced. As a result, the deeper the position of the light absorption body becomes, the more difficult the detection becomes. In the present embodiment, it is possible to detect up to 16 mm depth. In the comparative example, which is an example of a general NIRS (DOT) device, it is not possible to detect in the depth direction even when the Bayesian estimation is used. In general, in order to highly-accurately detect a three-dimensional position of the light absorption body including the depth direction, it is necessary for the probes to be arranged in high density, but in the present embodiment, such highly-accurate detection can be performed by arranging the probes in low density.

The optical sensor 10 according to the present embodiment (examples 1 and 2) described above includes the emitting system having a plurality of light source modules LM (light emitting devices) for emitting light onto the object under test (pseudo living body) and the detecting system for detecting the light which has been emitted from the emitting system and which has propagated in the object under test. Further, each of the light source modules LM emits non-parallel light fluxes onto substantially the same position on the object under test.

In this case, the incidence angles of the light fluxes on the object under test, which light fluxes are non-parallel to each other and emitted onto substantially the same position of the object under test (scattering body), are different from each other, and the light fluxes propagate in different propagation paths (refer to FIG. 36).

As a result, an amount of the obtained information related to the inside of the object under test is increased, and higher resolution can be achieved. Further, due to the improved resolution, it becomes possible to achieve the same resolution with the reduced probe density (i.e., the number of probes per unit area), which makes it possible to improve the installability (attachmentability).

As a result, it becomes possible for the optical sensor 10 to achieve a higher resolution without lowering the attachmentability to the object under test.

It should be noted that a fact that the light fluxes, which are incident on substantially the same position of the object under test, are non-parallel to each other means that the light fluxes form angles relative to each other. In other words, because there exist angles formed by the light fluxes, it becomes possible to form different propagation paths of the light fluxes. On the other hand, if it is assumed that the light fluxes incident on substantially the same position of the object under test are parallel to each other (e.g., if the light fluxes are parallel to the line normal to the surface of the object under test), the propagation paths of the light fluxes in the object under test must be the same.

Further, the light source module LM according to the present embodiment includes the surface emitting laser array having a plurality of surface emitting lasers (light emitting units) and the convex lens which is arranged on the optical paths of the light beams from the surface emitting lasers. The convex lens is used for causing the light beams to be non-parallel to each other, and the distance between the main point of the convex lens and the surface emitting laser array does not correspond to the focal length of the convex lens.

In this case, it is possible to prevent the concentration of the returned light beams on the surface emitting lasers and it is possible to prevent the output change of the surface emitting lasers. As a result, it is possible to stabilize the amount of light emitted from the surface emitting lasers, improve the detection accuracy in the optical sensor 10, and accordingly improve the resolution of the NIRS.

On the other hand, in the case where the surface emitting laser array is arranged at the position of the focal point of the convex lens, the light beams reflected by the external reflection surface are concentrated on the surface emitting lasers by the convex lens, and the laser oscillation becomes unstable. This phenomenon is called a returned light or a self-mixing phenomenon. In the case where the surface emitting laser array is used as a light source of the optical sensor, if this phenomenon occurs, the amount of the emitted light becomes unstable, which is a problem (for more detail, refer to Japanese Laid-open Patent Publication No. 2011-114228 and No. 2012-132740).

Further, a transparent resin having a refractive index substantially equal to that of the convex lens fills in between the convex lens and the surface emitting laser array.

In this case, because the refractive index does not change at the boundary surface between the convex lens and the surface emitting laser array, the returned light can be reduced. As a result, it becomes possible to stabilize the amount of light emitted from the surface emitting laser array, and accordingly improve the resolution of the NIRS.

Further, the detecting system includes a plurality of detection modules DM, each having a plurality of light receiving units (PDs) that respectively receive the light beams which have been emitted from the light source module LM onto the object under test and which have propagated in the object under test.

In this case, it is possible to individually obtain two sets of information corresponding to two different propagation paths in the object under test.

Further, the detection module DM includes the contact member and the housing which have the aperture arranged between the object under test and the light receiving units (PDs) for allowing a part of each of the light beams that have propagated in the object under test to pass.

In this case, it is possible to take the light into the housing through substantially the same position of the object under test. In other words, it is possible to allow only the light whose incidence angle is limited to some extent to be incident on the housing from the object under test, and it is easier for the light to be incident on the light receiving units.

Further, the detection module DM includes the division lens (light receiving lens) that individually guides the part of the light beams, which have passed through the aperture, onto the light receiving units.

In this case, it is possible to allow a part of the light beams having passed through the aperture to be individually incident on the respective light receiving units with a stable light amount.

Further, because the light source module LM includes the window member which is used to be in contact with the object under test and made of a material (transparent resin) having a refractive index greater than that of the object under test, it is possible to set the propagation angle (refracting angle) in the object under test to be greater relative to the incidence angle on the object under test. As a result, when compared with a case where the light is incident from air onto the object under test, the propagation angle becomes greater even when the incidence angle is the same. Therefore, when compared with the difference in the incidence angle between two light beams incident on substantially the same position of the object under test with different incidence angles, the difference in the propagation angle between the two light beams in the object under test becomes greater, and it is possible to cause the propagation paths to differ more greatly. As a result, it is possible to achieve higher resolution.

Further, the light source module LM includes the surface emitting lasers arranged in a two-dimensional manner and an emitting lens (lens) arranged on optical paths of the light beams from the surface emitting lasers.

In this case, it is possible to change the traveling directions of the light beams from the surface emitting lasers into desired directions (directions in which corresponding prisms are arranged).

Further, the light source module LM is arranged on the optical paths of the light beams via the emitting lens and includes the prism (reflection member) for reflecting the light beams in desired directions.

In this case, it is possible to further change the traveling direction of the light beams from the emitting lens into desired directions. In other words, it is possible to set the incidence angle on the object under test to be a desired angle.

As described above, the optical sensor 10 is capable of achieving higher resolution by effectively using the light propagation anisotropy with a simple configuration, and it is expected that the optical sensor 10 will be used in various fields such as in the DOT.

Further, the optical testing apparatus 100 includes the optical sensor 10 and the control unit (optical characteristics calculation unit) for calculating the optical characteristics of the object under test based on the detection results obtained by the optical sensor 10.

In this case, because of the higher detection accuracy of the optical sensor 10, it is possible to highly-accurately calculate the optical characteristics of the object under test.

Further, the optical sensor 10 according to the present embodiment (examples 1 and 2) includes an emitting system having a plurality of light source modules LM (light emitting devices) which emit light onto the object under test (e.g., living body) and a detecting system which detects the light which has been emitted from the emitting system onto the object under test and which has propagated in the object under test, where the light source modules LM are capable of emitting light beams having different wavelengths onto substantially the same position of the object under test.

In this case, it is possible to measure information in an object under test with high accuracy.

Specifically, it becomes also possible for a NIRS device which performs an inverse problem estimation to measure brain blood flow positions with higher accuracy.

Further, the light source module LM (Type III) includes two channels (whose emitted light beams have wavelengths different from each other) capable of emitting the two light beams having different wavelengths, two lenses 1 and 2 which are individually arranged on the optical paths of the corresponding light beams having different wavelengths emitted from the two channels, and a prism commonly arranged on the optical paths of the two light beams having different wavelengths via the corresponding two lenses, and the optical paths having different wavelengths via the prism are substantially the same. It should be noted that "the optical paths are substantially the same" means that the angle formed by the optical paths of the two light beams arbitrarily selected from the light beams having different wavelengths via the prism is equal to or less than 10 degrees.

In this case, it is possible to emit the light beams having different wavelengths onto the same position of the object under test by using a simple configuration.

Further, in the light source module LM (Type III), the prism includes reflection surfaces (total reflection surfaces R1 and R2) which reflect two light beams having different wavelengths via the lenses 1 and 2, respectively, and the optical paths of the two light beams having different wavelengths are not parallel from the two lenses 1 and 2 to the reflection surfaces.

In this case, compared with a configuration in which two refection surfaces are used for individually reflecting the two light beams having different wavelengths, it is possible to simplify the configuration while achieving reduced cost.

Further, in the light source module LM (Type III), compared with a case where a plurality of optical elements are used instead of the prism, it is possible to reduce the number of parts which should be mounted, and thus, the mounting cost is reduced.

Further, in the light source module LM (Type III), because the optical paths of the two light beams having different wavelengths from the two lenses 1 and 2 to the reflection surface of the prism become closer to each other as the optical paths get closer to the reflection surface of the prism, it is possible for the two light beams to be reflected on the reflection surface into the direction toward the object under test in a state where the optical paths are close to each other.

Further, in the light source module LM (Type III), because the two light beams having different wavelengths reflected by the reflection surface of the prism intersect near the emitting end of the light source module LM (Type III), it is possible to cause the two light beams to be incident accurately on the same position of the object under test.

Further, in the light source module LM (Type III), because each of the two channels includes a plurality of light emitting units arranged in an array manner and positional relations between the light emitting units and the optical axes of the corresponding lenses differ between the light sources, it is possible to emit the two light beams, which have different wavelengths and are emitted from the two light emitting units corresponding to the two channels, from the lenses 1 and 2 in a non-parallel state.

Further, in the light source module LM (Type III), because the centers of the channels (array centers) are dislocated from the optical axes of the corresponding lenses, when two light emitting units corresponding to the two channels are referred to as a pair, it is possible to cause the positional relations of all pairs relative to the optical axis of the lens to be different from each other.

Further, a transparent resin whose refractive index is equal to that of the lenses 1 and 2 may fill in between the lenses 1 and 2 and the two channels (refer to FIG. 23).

Further, the lenses 1 and 2 may have a shape with a convex surface facing the corresponding channel side (refer to FIG. 25).

Further, a common optical element of the light source module LM (Type II) and the light source module LM (Type III) is not limited to a prism, but may be any member as long as the member includes at least one reflection surface which reflects a plurality of light beams having different wavelengths.

Second Embodiment

Next, a second embodiment of the present invention will be described. In the present embodiment, a method of adapting the probes, which are described in the first embodiment, to an actual human body will be described. Here, it is assumed that the object under test is changed from the phantom (the water tank filled with white water) to a head part of a human body, and the light absorption body is brain blood flow.

In the present embodiment, an object is to accurately estimate the distribution of blood flow in brain. In the present embodiment, a person under test (body under test) is measured, and the figure is modeled based on the measured data and the Monte Carlo simulation is performed. The head shape of the person under test is measured by using magnetic resonance imaging (hereinafter, referred to as MRI) method. Base on the images, the shapes of the four parts, namely the scalp, the skull bone, the cerebral fluid, and the brain cortex, are calculated.

The three-dimensional data may become necessary for highly-accurate detections, but standard shape data of a brain model may alternatively be used. Because those parts have the respective values of a scattering coefficient, anisotropy, and an absorption coefficient which are generally known, those values are used. The probes are accurately fixed to the head with a fixing tool, and the setting position is accurately measured as well. The probes, etc., are the same as those in the first embodiment, and the repeated descriptions thereof are herein omitted. Here, optical simulation is performed based on the accurate shapes, positions, and values of the parts.

In the following, a method for measuring the blood flow in a brain will be described referring to a flowchart illustrated in FIG. 37. First, the person under test is relaxed (step S31), and the probes (detection modules DM and light source modules LM) are attached to the head (step S32). At this time, the probes are carefully set (installed) one by one on the respective predetermined positions using a fixing member in such a way that no hair and the like is sandwiched between the probes and the scalp. Under the set condition, channels are emitted (step S33). The emission (pulse emission) is performed on a group basis, and the current value is determined in such a way that the emission intensity is approximately 4 mW. The emission period is about several ms, during which the detection values of all the PDs are read and averaged (step S34). The averaged values are stored in a recording medium (step S35).

In the next group, the emission for several ms, the measurement, and the data storage are similarly repeated (steps S36, S37, and S33 through S35). After emissions and the measurement of all the light source modules LM are completed, the person under test is requested to perform a task (steps S38 through S41). Here, a general verbal fluency task is performed. Details of the verbal fluency task are described in Japanese Laid-open Patent Publication No. 2012-080975.

By performing the task, the brain is activated, and brain blood flow occurs only at the activated parts. The blood flow includes oxygenated hemoglobin and reduced hemoglobin and light absorption occurs due to the blood flow. The inverse problem estimation, etc., by the Bayesian estimation is in accordance with the method described in the above first embodiment, and the repeated description is herein omitted. The accuracy of the blood flow positions obtained in this measurement can be checked by functional magnetic resonance imaging (fMRI). "fMRI" is a method for visualizing a hemodynamic reaction related to the activity of the brain and the spinal cord of a human or an animal using the MRI. Based on the checking and the measurement, it is understood that the measurement with the optical sensor of the present embodiment has a higher resolution.

Third Embodiment

Next, a third embodiment of the present invention will be described. In the third embodiment, the light source modules LM and the detection modules DM similar to those in the first embodiment are used, but the layout thereof includes ideas of the present inventors. The descriptions other than the layout are the same as those in the first embodiment and the descriptions thereof are herein omitted.

In example 2 of the first embodiment, as illustrated in FIG. 15, two detection modules DM and the two light source modules LM are arranged at the respective corners of a substantial square. However, in this arrangement, at the point indicated by the X mark in FIG. 15, the optical path between the light source module LM and the detection module DM is elongated. As a result, sufficient light amount may not be obtained by the detection module DM, the noise at this point may become greater, and the detection accuracy may be lowered.

To resolve the above problem, the present inventors have actively researched to determine an appropriate probe layout and have found that the layout illustrated in FIG. 38 is most suitable. In the layout in FIG. 38, the light source modules LM and the detection modules DM are arranged in a manner such that two of either the light source modules LM or the detection modules DM are arranged at two respective corners of a regular triangle relative to the object under test and the other of the light source modules LM and the detection modules DM is arranged at the third corner of the regular triangle.

Here, as a simple example, the positions at which distances between the light source module LM and the detection module DM are the longest are studied. Here, it is assumed that the distance (pitch) between the light source module LM and the detection module DM is "a" in both cases. In the case of the position X in FIG. 15, the distance of the dotted line is calculated as ($\sqrt{2}$)a (about 1.414a). On the other hand, in the case of the position X in FIG. 38, the distance of the dotted line is calculated as $(1+\sqrt{3})a/2$ (about 1.366a)<($\sqrt{2}$)a. In other words, when the longest distances are compared between the layouts in FIG. 15 and FIG. 38, the longest distance in FIG. 38 is shorter, and it is understood that the layout in FIG. 38 is more preferable.

By using the probe layout in FIG. 38, it is understood that the detection area becomes wider as a result of inverse problem estimation which is performed in the same manner as that in the first embodiment.

Fourth Embodiment

Next, a fourth embodiment of the present invention will be described. In the fourth embodiment, although the same layout of the light source modules LM and the detection modules DM as in the first embodiment is used, the layout of the channels of the light source module LM and the PDs of the detection module DM includes ideas of the present inventors. The descriptions other than the layout of channels and PDs are the same as those in the first embodiment and the descriptions thereof are herein omitted.

In example 2 of the first embodiment, as illustrated in FIG. 15, the light source modules LM and the detection modules DM are arranged in such a way that the light source modules LM and the detection modules DM are adjacent to each other in both X and Y directions, which directions are orthogonal to each other, relative to the object under test.

However, as described above, with this layout, at the point indicated by the X mark in FIG. 15, the optical path between the light source module LM and the detection module DM is elongated. As a result, sufficient light amount may not be obtained by the detection module DM, the noise at this point may become greater, and the detection accuracy may be lowered.

In a comparative example illustrated in FIG. 39, the light source modules LM and the detection modules DM are arranged in such a way that the light source modules LM and the detection modules DM are adjacent to each other in both X and Y directions, which directions are orthogonal to each other, relative to the object under test, and both the emitting directions and the detection directions (incidence directions of light on the light receiving units) are parallel to the X direction or the Y direction. Because the lenses installed near the surface emitting lasers have point-symmetric optical characteristics, the emitting directions are determined based on the positions of the surface emitting lasers and the positions of the groups. Similarly, because of the point-symmetric optical characteristics of the lenses, the detection directions are determined based on the division layout of the PD arrays.

Here, when the surface emitting laser array chip is arranged as illustrated in FIG. 40A, the emitting directions are inclined relative to both the X direction and the Y direction in a planer view (when viewed from the +Z direction). This inclination is caused by a fact that the center positions of the groups are inclined relative to the lens center. Similarly, in the detection module DM, by arranging the center of the lens at the chip center of the four divided PD array chip (photodiode array chip), the detection directions (the incidence directions of light onto the light receiving units) are directions as illustrated in FIG. 40B. The above detection directions and the emitting directions are illustrated together with the layout of the probes in FIG. 41 It is understood that the emitting directions and the detection directions are inclined relative to the X direction and the Y direction in a planer view (when viewed from the +Z direction).

In this case, similar to the sensitivity distribution described above, because of anisotropy of light, it is expected that more sensitivity may be obtained at the X marked position in FIG. 41.

As a result of the inverse problem estimation performed similar to the first embodiment using the layouts of FIG. 40A and FIG. 40B, it is understood that the detectable area becomes larger (wider).

It should be noted that in the above embodiments, the number of the light source modules LM in the emitting system and the number of the detection modules DM in the detection system may be appropriately changed. The point is that the emitting system may include at least one light source module LM, and the detection system may include at least one detection module DM.

Further, in the above embodiments, the configuration of the light source module LM (light emitting device) may be appropriately changed. For example, the number and the layout of the surface emitting laser array chips of the light emitting unit may be changed. Further, the type, the shape, the size, the number, etc., of the lenses may be appropriately changed.

Further, in the above embodiments, as the light sources of the light emitting device, the surface emitting lasers are used, but, for example, edge-emitting lasers (LDs), light-emitting diodes (LEDs), organic EL elements, and lasers other than the semiconductor laser may be used.

Further, in the above embodiments, prisms are used as the reflection members of the light emitting device, but other mirrors or the like may be used.

Further, in the surface emitting laser array chip in example 2, the number and the layout of the groups and the number and the layout of the channels of the groups may be appropriately changed.

Further, the configuration of the detection module DM (light detecting device) may be appropriately changed. For example, the aperture may not be arranged. Further, for example, the division lens may not be arranged.

It is needless to say that the figure (shape), the size, the material, the number, the dimensions, the value of the members and parts as described above are just examples, and may be appropriately changed.

It should be noted that at least a part of the optical sensor described in the above embodiments may be exchangeably used among the embodiments and the examples.

The present application is based on and claims the benefit of priority of Japanese Priority Application No. 2014-230745 filed on Nov. 13, 2014, the entire contents of which are hereby incorporated by reference.

REFERENCE SIGNS LIST

10 Optical sensor,
100 Optical testing apparatus,
LM Light source module (light emitting device),
DM Detection module (light detecting device)

CITATION LIST

Patent Literature

PTL 1: Patent document 1: Japanese Patent No. 3779134

The invention claimed is:
1. An optical sensor comprising:
an emitting system including at least one light emitting device which emits light onto an object; and
a detecting system detecting the light which has been emitted by the emitting system and which has propagated through the object,
wherein the light emitting device is capable of emitting a plurality of light beams with different wavelengths onto substantially the same position of the object,
wherein the light emitting device includes (i) a plurality of light sources to emit light beams, respectively, with different wavelengths, (ii) a plurality of individual optical elements corresponding to the plurality of light sources, respectively, each individual optical element arranged on an optical path of a light beam, which is amongst the light beams with different wavelengths and is emitted by the corresponding light source, and (iii) a common optical element which is arranged in common on the optical paths of the respective light beams emitted by the plurality of light sources to the common optical element via the plurality of individual optical elements corresponding to the plurality of light sources, respectively,
wherein the optical paths of the respective light beams, as the plurality of light beams emitted onto the object via the light emitting device, are substantially the same,
wherein each light source amongst the plurality of light sources includes a plurality of light emitting units arranged in an array manner, and
wherein for each light source amongst the plurality of light sources, a position relationship between the plurality of light emitting units of the light source and an optical axis of the individual optical element corresponding to the light source is different than that of other light source amongst the plurality of light sources.
2. The optical sensor according to claim 1,
wherein the common optical element includes a reflection surface which reflects the plurality of light beams with different wavelengths via the plurality of individual optical elements corresponding to the plurality of light sources, respectively, and
wherein the optical paths of the plurality of light beams, respectively, with different wavelengths are not parallel to each other from the plurality of individual optical elements to the reflection surface.
3. The optical sensor according to claim 2,
wherein the optical paths of the plurality of light beams with different wavelengths from the plurality of individual optical elements, respectively, to the reflection surface become closer to each other as the optical paths become closer to the reflection surface.
4. The optical sensor according to claim 2,
wherein the plurality of light beams with different wavelengths reflected by the reflection surface intersect near an emitting end of the light emitting device.
5. The optical sensor according to claim 2,
wherein an angle formed by two optical paths of any two light beams selected from the plurality of light beams with different wavelengths reflected by the reflection surface is equal to or less than 10 degrees.
6. The optical sensor according to claim 5,
wherein the angle is equal to or less than 1 degree.
7. The optical sensor according to claim 1,
wherein a center of at least one of the plurality of light sources is dislocated from a position on an optical axis of the corresponding individual optical element.
8. The optical sensor according to claim 1,
wherein the light source is a surface emitting laser array.
9. The optical sensor according to claim 1,
wherein a transparent resin having a refractive index substantially equal to that of the individual optical element fills in between at least one individual optical element and the corresponding light source.

10. The optical sensor according to claim 1, wherein at least one individual optical element has a shape with a convex surface facing the corresponding light source.

11. An optical testing apparatus comprising:
the optical sensor according to claim 1; and
an optical characteristics calculating unit configured to calculate optical characteristics of the object based on detection results in the optical sensor.

12. An optical characteristics detection method for detecting optical characteristics of the object by using the optical sensor according to claim 1, the method comprising:
a step of calculating sensitivity distribution of the object for light; and
a step of calculating optical characteristics of the object based on at least the sensitivity distribution.

* * * * *